(12) United States Patent  (10) Patent No.:  US 8,181,994 B1
Valenti, Jr. et al.  (45) Date of Patent:  May 22, 2012

(54) SHEET WITH WRISTBAND

(75) Inventors: F. Paul Valenti, Jr., Barrington, IL (US); Carl Opel, Carol Stream, IL (US); Daniel Hedger, Grayslake, IL (US)

(73) Assignee: Chicago Tag & Label, Inc., Libertyville, IL (US)

( * ) Notice: Subject to any disclaimer, the term of this patent is extended or adjusted under 35 U.S.C. 154(b) by 0 days.

(21) Appl. No.: 12/892,513

(22) Filed: Sep. 28, 2010

Related U.S. Application Data

(63) Continuation-in-part of application No. 12/175,736, filed on Jul. 18, 2008, now Pat. No. 7,828,333.

(51) Int. Cl.
*B42D 15/00* (2006.01)
*A44C 5/00* (2006.01)
*A61B 5/103* (2006.01)
*A61B 5/117* (2006.01)
*G09F 3/10* (2006.01)

(52) U.S. Cl. ............ 283/108; 283/81; 283/101; 40/633; 40/675

(58) Field of Classification Search ............... 283/81, 283/101, 107–111; 40/360, 633, 675; 428/40.1, 428/42.2, 42.3
See application file for complete search history.

(56) References Cited

U.S. PATENT DOCUMENTS

| | | | |
|---|---|---|---|
| 4,854,610 A | 8/1989 | Kwiatek | |
| 5,653,472 A * | 8/1997 | Huddleston et al. | ............ 283/75 |
| 5,933,993 A | 8/1999 | Riley | |
| 6,000,160 A | 12/1999 | Riley | |
| 6,016,618 A | 1/2000 | Attia et al. | |
| 6,067,739 A | 5/2000 | Riley | |
| 6,438,881 B1 | 8/2002 | Riley | |
| 6,510,634 B1 | 1/2003 | Riley | |
| 6,748,687 B2 | 6/2004 | Riley | |
| 6,788,687 B2 | 9/2004 | Bao et al. | |
| 6,836,215 B1 | 12/2004 | Laurash et al. | |
| 6,971,200 B2 | 12/2005 | Valenti | |
| 7,000,951 B2 * | 2/2006 | Valenti, Jr. | ...................... 283/81 |
| 7,017,293 B2 | 3/2006 | Riley | |
| 7,017,294 B2 | 3/2006 | Riley | |
| 7,047,682 B2 | 5/2006 | Riley | |
| 7,222,448 B2 | 5/2007 | Riley | |
| 7,244,748 B2 | 7/2007 | Borgens et al. | |
| 7,316,358 B2 | 1/2008 | Kotik et al. | |
| 7,320,194 B2 | 1/2008 | Ali et al. | |

(Continued)

FOREIGN PATENT DOCUMENTS

WO    WO 99/25565    5/1999

(Continued)

OTHER PUBLICATIONS

Aug. 2005, Issue 3, Precision Dynamics Corporation Insider, Anderson Hospital Reduces Costs Improves Patent Safety with PDC Sentry Bar Code LabelBand Wristbands, www.pdcorp.com.

(Continued)

*Primary Examiner* — Edward Tolan
*Assistant Examiner* — Kyle Grabowski
(74) *Attorney, Agent, or Firm* — Ice Miller LLP

(57) ABSTRACT

A printable form comprising a printable face surface and a wristband releasably bonded to f the printable face surface. In at least one embodiment the wristband may be detached from the printable face surface and secured to around a body part for use in identification. In at least one embodiment the wristband comprises one or more labels that may be detached therefrom.

17 Claims, 61 Drawing Sheets

U.S. PATENT DOCUMENTS

| | | | |
|---|---|---|---|
| 7,322,613 B2 * | 1/2008 | Penuela et al. | 283/81 |
| 7,386,949 B2 | 6/2008 | Riley | |
| 7,417,541 B2 | 8/2008 | Lerch et al. | |
| 7,454,854 B2 | 11/2008 | Riley | |
| 7,454,855 B2 | 11/2008 | Kotik et al. | |
| 7,461,473 B2 | 12/2008 | Riley | |
| 2004/0113421 A1 * | 6/2004 | Penuela et al. | 283/81 |
| 2004/0261644 A1 | 12/2004 | Stewart et al. | |
| 2005/0181165 A1 | 8/2005 | Franko, Sr. | |
| 2005/0285385 A1 | 12/2005 | Bova et al. | |
| 2006/0113788 A1 | 6/2006 | Riley | |
| 2006/0218837 A1 | 10/2006 | Riley | |
| 2006/0236578 A1 | 10/2006 | Saint et al. | |
| 2007/0120358 A1 * | 5/2007 | Waggoner et al. | 283/81 |
| 2007/0283607 A1 | 12/2007 | Sloot | |
| 2008/0067802 A1 | 3/2008 | Bell et al. | |
| 2008/0098635 A1 | 5/2008 | Jain et al. | |
| 2008/0109937 A1 | 5/2008 | Greer | |
| 2008/0309065 A1 | 12/2008 | Ali et al. | |
| 2009/0277061 A1 * | 11/2009 | Jain et al. | 40/633 |

FOREIGN PATENT DOCUMENTS

| | | |
|---|---|---|
| WO | WO 2005/081928 | 9/2005 |

OTHER PUBLICATIONS

Self-Laminating Laser Wristbands, Institute of Medicine. To Err is Human: Building a Safer Health System. Washington: National Academy Press: 1999: Bates DW. Spell N. Cullen DI. et al. The costs of adverse drug events in hopitalized patients, JAMA 1997:277.

Healthcare: A Solution for Positive Patient Identification, Self-Laminating Laser Wristbands, Russell F. Lewis, HIMSS Summer Conference 2002, Leape 1995 and California Healthcare Foundation 2001.

* cited by examiner

SHEET WITH WRISTBAND

This patent application is a continuation-in-part of U.S. application Ser. No. 12/175,736, filed Jul. 18, 2008, now U.S. Pat. No. 7,828,333 the disclosure of which is hereby incorporated by reference in its entirety.

BACKGROUND

Identification wristbands are commonly used in a hospital or other setting to promote the easy identification of patients or other wearers. In the instance of a hospital use, a patient is generally provided with an identification wristband that is secured about the wrist of the patient upon admission to the hospital. In addition, a number of labels for use in identifying fluid samples, medications, charts, folders, papers and other common hospital objects specific to an admitted patient are often printed when a patient is admitted.

Often, the labels and wristbands are printed separately. The wristband is placed on the patient, while the labels are put into a patient chart, or otherwise saved for later use. However, in an effort to streamline patient admission procedures, and in light of the widespread use and low cost of computer driven printers such as laser printers, it has become desirable to print the labels and wristbands in a single step.

Accordingly, it is desired to provide an improved form of a combined wristband and printable sheet.

SUMMARY

The present disclosure includes disclosure of a combined wristband and printable sheet form.

At least one embodiment of the present disclosure comprises a sheet-like material, comprising a leading edge, a trailing edge, first and second side edges, a face surface, and a second surface opposing the face surface; and a wristband comprising a top side and an opposing underside, the underside comprising an underside surface, where the wristband is bounded by a leading margin, a trailing margin, and first and second side margins. In at least one such embodiment a first adhesive stripe is adhered to the underside surface and releasably bonded to the face surface; and a dry lift adhesive material is interposed between the underside surface and the face surface, causing the underside surface to be removably adhered to the face surface.

In at least one aspect of an embodiment of a printable form according to the present disclosure, a wristband comprises a tamper resistant feature formed in the wristband. In at least one such embodiment, the tamper resistant feature is formed in the wristband within an area of the wristband to which the first adhesive stripe is adhered. In at least one aspect of an embodiment of a printable form according to the present disclosure, the tamper resistant feature comprises at least one line of weakness formed in the wristband, and the at least one line of weakness is inboard of the leading margin, the trailing margin, and the first and second side margins. In at least one aspect of an embodiment of a printable form according to the present disclosure, the at least one line of weakness is closer to the leading margin than to the trailing margin.

In at least one aspect of an embodiment of a printable form according to the present disclosure, the printable form further comprises a first and a second adhesive stripe adhered to the underside surface. In at least one such embodiment the second adhesive stripe is releasably bonded to the face surface, wherein the first adhesive stripe is positioned closer to the leading margin than to the trailing margin, and the second adhesive stripe is positioned closer to the trailing margin than to the leading margin. In at least one aspect of an embodiment of a printable form according to the present disclosure, when the wristband is removable from the face surface, and following removal from the face surface the first adhesive stripe and the second adhesive stripe remain adhered to the underside surface.

In at least one aspect of an embodiment of a printable form according to the present disclosure, a dry lift adhesive material is positioned between a first adhesive stripe and a second adhesive stripe. In at least one aspect of an embodiment of a printable form according to the present disclosure, the dry lift adhesive material comprises properties such that when the wristband is removed from the face surface the underside surface is substantially free of tackiness except where the first and second adhesive stripes are adhered.

In at least one aspect of an embodiment of a printable form according to the present disclosure, the leading edge of the wristband is narrower than the trailing edge of the wristband.

In at least one aspect of an embodiment of a printable form according to the present disclosure, the printable form comprises at least one release patch on the face surface, wherein the at least one release patch is interposed between a first adhesive stripe and the face surface.

In at least one aspect of an embodiment of a printable form according to the present disclosure, a wristband comprises an upper ply and a lower ply, and a boundary of at least one detachable label is defined in the upper ply.

At least one embodiment of the present disclosure comprises a sheet-like material, comprising a first surface and a second surface opposite the first surface, a leading edge, a trailing edge, and first and second side edges; and a wristband comprising a leading margin, a trailing margin, first and second side margins, a stub portion, a removeable portion, and a line of weakness between the stub portion and the removeable portion, a top side, and an underside comprising an underside surface bounded by the leading margin, the trailing margin, and the first and second side margins. In at least one such embodiment, at least one adhesive stripe is interposed between at least a portion of the underside surface and the face ply surface. In such an embodiment, the at least one adhesive stripe forms a first adhesive bond between at least a portion of the removeable portion and the face ply surface and a second adhesive bond between at least a portion of the stub portion and the face ply surface, wherein the first adhesive bond can be broken using less force than the second adhesive bond.

In at least one aspect of an embodiment of a printable form according to the present disclosure, a wristband comprises a tamper resistant feature, and the tamper resistant feature comprises at least one deformation in the wristband. In at lest one such embodiment, the at least one deformation is inboard of the leading margin, the trailing margin, and the first and second side margins. In at least one aspect of an embodiment of a printable form according to the present disclosure, the at least one deformation is closer to the leading margin than to the trailing margin.

In at least one aspect of an embodiment of a printable form according to the present disclosure, the printable form comprises a first adhesive stripe is between the stub portion and the first surface, a second adhesive stripe between the removeable portion and the first surface, and a third adhesive stripe between the removeable portion and the first surface. In at least one such embodiment, the second adhesive stripe is positioned closer to the leading margin than to the trailing margin, and the third adhesive stripe is positioned closer to the trailing margin than to the leading margin. In at least one aspect of an embodiment of a printable form according to the present disclosure, the wristband is removable from the face surface, and wherein following removal from the face surface the second adhesive stripe and the third adhesive stripe remain adhered to the underside surface.

In at least one aspect of an embodiment of a printable form according to the present disclosure, the printable form comprises a substrate material comprising a leading edge, a trailing edge, and first and second side edges, the substrate material comprising a face ply and a liner ply, the face ply comprising a face ply surface and a second surface opposite the face ply surface, the liner ply removably adhered to the second surface of the face ply; and a wristband, the wristband comprising a leading margin, a trailing margin, first and second side margins, a stub portion, a removeable portion, and a line of weakness between the stub portion and the removeable portion, a top side, and an underside, the underside comprising an underside surface bounded by the leading margin, the trailing margin, and the first and second side margins. In at least one such embodiment, at least one adhesive stripe is interposed between at least a portion of the underside surface and the face ply surface. In at least one such embodiment, the at least one adhesive stripe forms a first adhesive bond between at least a portion of the removeable portion and the face ply surface and a second adhesive bond between at least a portion of the stub portion and the face ply surface, wherein the first adhesive bond can be broken using less force than the second adhesive bond. In at least one aspect of an embodiment of a printable form according to the present disclosure, a wristband comprises a tamper resistant feature formed in the wristband. In at least one aspect of an embodiment of a printable form according to the present disclosure, the tamper resistant feature comprises at least one line of weakness formed in the wristband, the at least one line of weakness being inboard of the leading margin, the trailing margin, and the first and second side margins.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

Figure 1A:
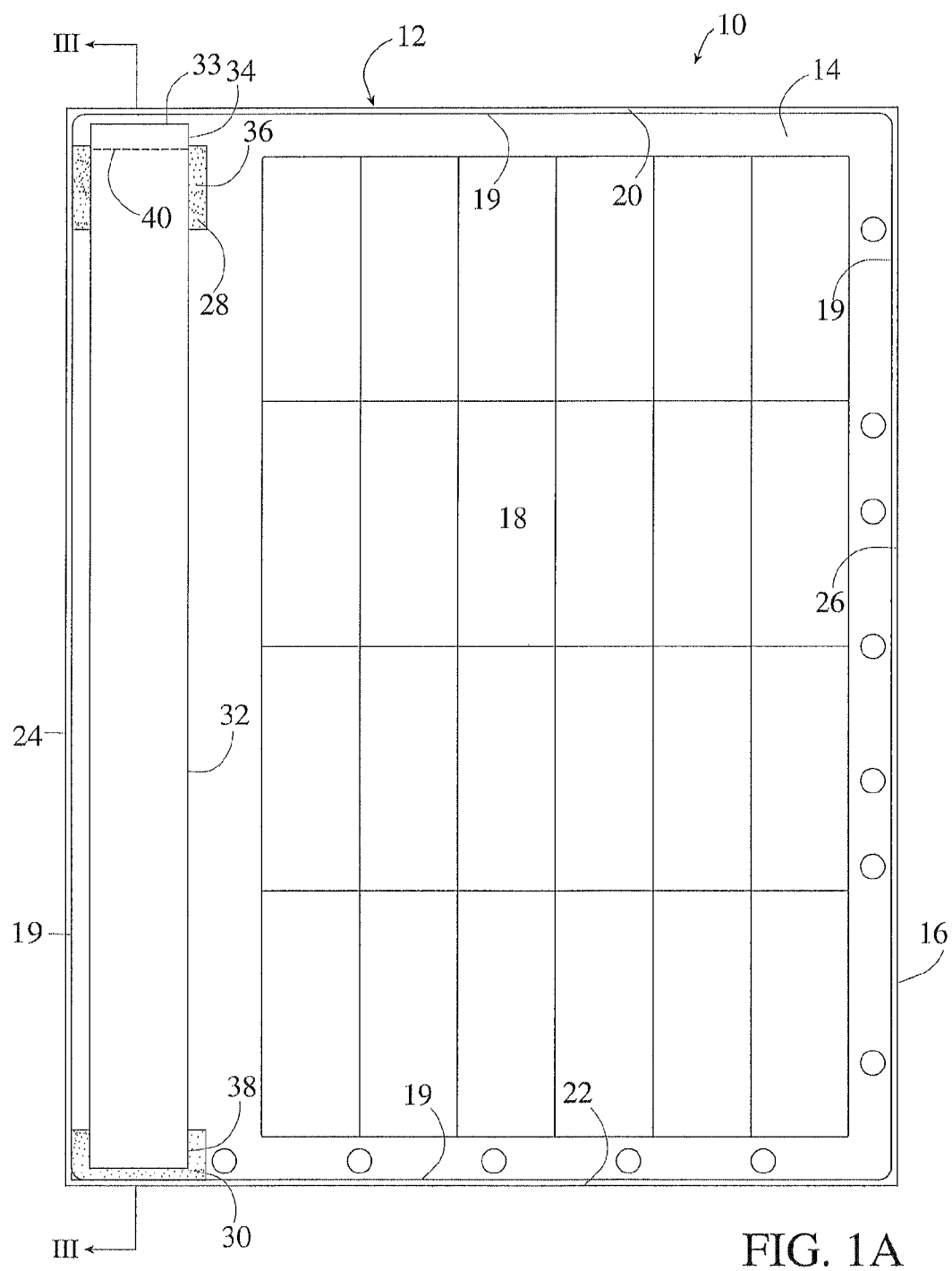
FIG. 1A shows a top view of a wristband label sheet according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1A shows a top view of wristband label sheet 10 according to at least one embodiment of the present disclosure. Shown in FIG. 1A are label sheet 12, comprising label material 14 and liner material 16. Adhesive 15 (not shown in FIG. 1A) is interposed between label material 14 and liner material 16 and removably adheres label material 14 to liner material 16. In at least one embodiment of the present disclosure, liner material 16 comprises a silicone coating on the surface facing adhesive 15. In the embodiment of wristband label sheet 10 shown in FIG. 1A, liner material 16 is bounded by leading edge 20, trailing edge 22, side edge 24, and side edge 26. Label sheet 12 may be of any size. In at least one embodiment of label sheet 12 according to the present disclosure, the outer dimensions of label sheet 12 are selected to enable label sheet 12 to fit in a commercially available printing device. For example, in such an embodiment, the outer dimensions of label sheet 12 may be 8½"×11", 8½"×14", or 210 mm×297 mm.

In at least one embodiment of the present disclosure, label material 14 comprises perimeter 19 defining a boundary of label material 14. In at least one embodiment of the present disclosure, at least a portion of perimeter 19 is inboard of the boundary formed by leading edge 20, trailing edge 22, side edge 24, and side edge 26. In at least one embodiment of the present disclosure, perimeter 19 is coextensive with the boundary formed by leading edge 20, trailing edge 22, side edge 24, and side edge 26.

In at least one embodiment of the present disclosure, label material 14 comprises a material suitable for the printing of indicia thereon, such as, for example, paper, polyester, or another polymer material. Indicia may be marked or printed on the top side of label material 14. For example, the top side of label material 14 may be exposed to an ink jet printer, a laser print, or another type of printing device capable of applying indicia to the top side of label material 14. The inks, toners, and/or other printing materials used in the application of indicia to the top side of label material 14 are selected to be compatible with the printing device used to apply such indicia, the material used for label material 14, and the intended use of wristband label sheet 10.

In the embodiment of wristband label sheet 10 shown in FIG. 1A, label material 14 comprises a plurality of labels 18. In at least one embodiment, labels 18 are die cut in label material 14. In at least one embodiment of the present disclosure, label material 14 comprises twenty-four labels 18, each having dimensions of about 1"×2.5". Other sizes and quantities of labels 18 are possible.

In the embodiment of wristband label sheet 10 shown in FIG. 1A, label material 14 comprises release patch 28 and release patch 30. Release patches 28, 30 comprise areas of a release coating (such as, for example, a silicone) applied to the surface of label material 14, to allow the removable adherence of wristband 32 to label sheet 14, as discussed herein. In at least one embodiment of the present disclosure, release patches 28, 30 comprise free radical ultraviolet cured silicone. In at least one embodiment of the present disclosure, release patches 28, 30 comprise a cationic ultraviolet cured release coating. Alternatively, any type of coating (including no-silicone coatings) that permits the removable adherence of wristband 32 to label sheet 14 may be used.

Also shown in the embodiment of wristband label sheet 10 shown in FIG. 1A is wristband 32 comprising stub 33 and line of weakness 40. In at least one embodiment of the present disclosure, line of weakness 40 comprises a series of perforations. In at least one embodiment of the present disclosure, wristband 32 (including stub 33) is constructed of a polyester material, although other materials suitable for the intended use of wristband 32 may be used. In at least one embodiment of the present disclosure, wristband 32 has dimensions of about 1"×10.75", however wristband 32 may be of any size that fits on label sheet 12.

Figure 1B:
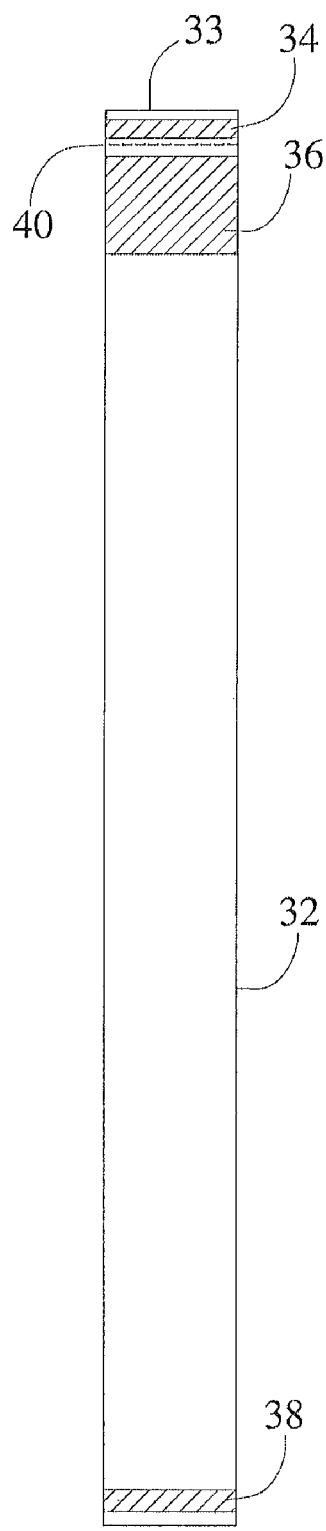
FIG. 1B shows the underside of a wristband according to at least one embodiment of the present disclosure.

FIG. 1B shows the underside of wristband 32 before attachment to label sheet 12, according to at least one embodiment of the present disclosure. Shown in FIG. 1B are wristband 32 comprising stub 33, adhesive stripe 34, adhesive stripe 36, adhesive stripe 38, and line of weakness 40. In at least one embodiment of the present disclosure, adhesive stripes 34, 36, 38 comprise a layer of a hot melt adhesive.

Referring back to FIG. 1A, shown therein are the locations of adhesive stripes 34, 36, 38 on the underside of wristband 32. Adhesive stripe 34 is interposed between label material 14 and stub 33, and adheres label material 14 to stub 33. In at least one embodiment of the present disclosure, adhesive stripe 34 is oriented toward leading edge 20 of label sheet 12. Adhesive stripe 36 is interposed between wristband 32 and release patch 28 and removably adheres wristband 32 to release patch 28. Adhesive stripe 38 is interposed between wristband 32 and release patch 30 and removably adheres wristband 32 to release patch 30. As discussed herein, adhesive stripes 36, 38 are operable to secure wristband 32 around a subject's wrist after wristband 32 is removed from label sheet 12.

In at least one alternative embodiment of the present disclosure, release patch 28 and adhesive stripe 36 may be omitted from wristband label sheet 10. In such an embodiment adhesive stripe 34 remains and is interposed between label material 14 and stub 33 to adhere label material 14 to stub 33. In such an embodiment adhesive stripe 38 remains and is interposed between wristband 32 and release patch 30 to removably adhere wristband 32 to release patch 30.

In at least one alternative embodiment of the present disclosure, adhesive stripes 36, 38 comprise a repositionable adhesive. In such an embodiment release patches 28, 30 may be omitted from wristband label sheet 10. In at least one other alternative embodiment of the present disclosure, a wristband label sheet comprises a stub at each end of the wristband.

Indicia may be marked or printed on the top side of wristband 32. For example, the top side of wristband 32 may be exposed to an ink jet printer, a laser print, or another type of printing device capable of applying indicia to the top side of wristband 32. Indicia may be printed on wristband 32 before, after, or concurrently with the printing of indicia on label material 14. The inks, toners, and/or other printing materials used in the application of indicia to the top side of wristband 32 are selected to be compatible with the printing device used to apply such indicia, the material used for wristband 32, and the intended use of wristband 32.

Figure 1C:
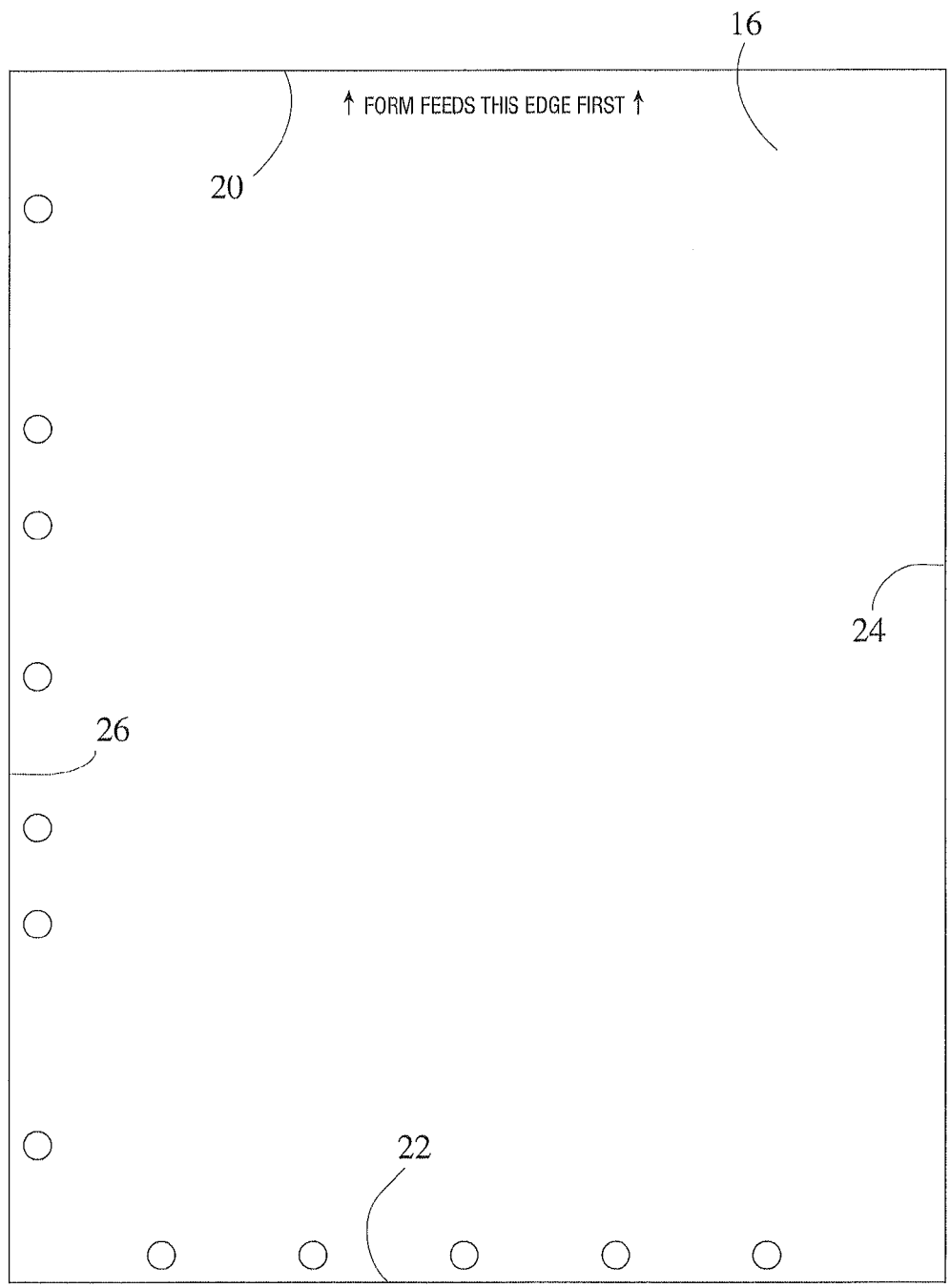
FIG. 1C shows a bottom view of wristband label sheet according to at least one embodiment of the present disclosure.

FIG. 1C shows a bottom view of wristband label sheet 10 of FIG. 1A. Shown in FIG. 1C is liner 16, bounded by leading edge 20, trailing edge 22, side edge 24, and side edge 26.

Figure 2A:
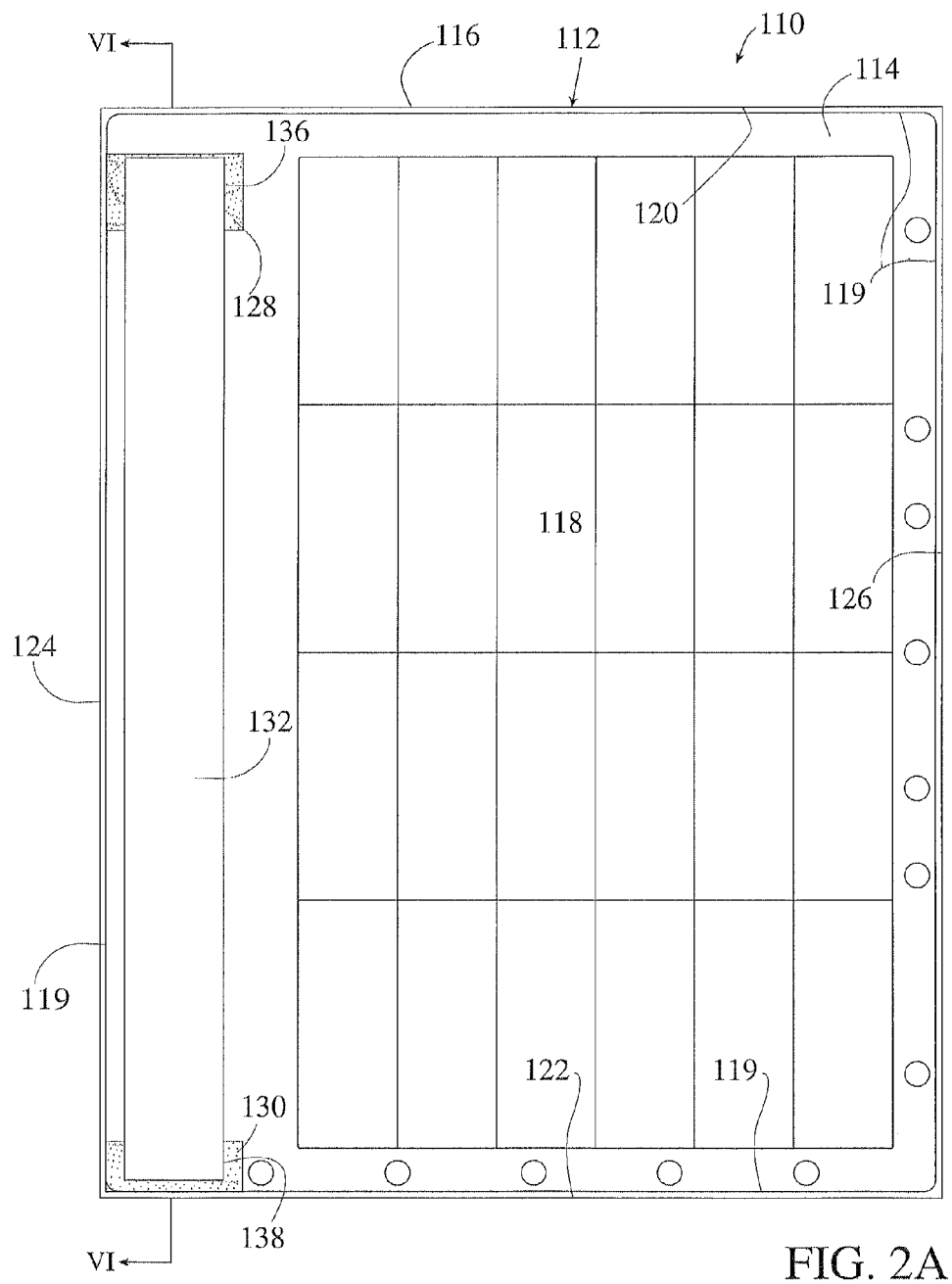
FIG. 2A shows a top view of a wristband label sheet according to at least one embodiment of the present disclosure.

FIG. 2A shows a top view of wristband label sheet 110 according to at least one embodiment of the present disclosure. Shown in FIG. 2A are label sheet 112, comprising label material 114 and liner material 116. Adhesive 115 (not shown in FIG. 2A) is interposed between label material 114 and liner material 116 and removably adheres label material 114 to liner material 116. In at least one embodiment of the present disclosure, liner material 116 comprises a silicone coating on the surface facing adhesive 115. In the embodiment of wristband label sheet 110 shown in FIG. 2A, liner material 116 is bounded by leading edge 120, trailing edge 122, side edge 124, and side edge 126. Label sheet 112 may be of any size. In at least one embodiment of label sheet 112 according to the present disclosure, the outer dimensions of label sheet 112 are selected to enable label sheet 112 to fit in a commercially available printing device. For example, in such an embodiment, the outer dimensions of label sheet 112 may be 8½"×11", 8½"×14", or 210 mm×297 mm.

In at least one embodiment of the present disclosure, label material 114 comprises perimeter 119 defining a boundary of label material 114. In at least one embodiment of the present disclosure, at least a portion of perimeter 119 is inboard of the boundary formed by leading edge 120, trailing edge 122, side edge 124, and side edge 126. In at least one embodiment of the present disclosure, perimeter 119 is coextensive with the boundary formed by leading edge 120, trailing edge 122, side edge 124, and side edge 126.

In at least one embodiment of the present disclosure, label material 114 comprises a material suitable for the printing of indicia thereon, such as, for example, paper, polyester, or another polymer material. Indicia may be marked or printed on the top side of label material 114. For example, the top side of label material 114 may be exposed to an ink jet printer, a laser print, or another type of printing device capable of applying indicia to the top side of label material 114. The inks, toners, and/or other printing materials used in the application of indicia to the top side of label material 114 are selected to be compatible with the printing device used to apply such indicia, the material used for label material 114, and the intended use of wristband label sheet 110.

In the embodiment of wristband label sheet 110 shown in FIG. 2A, label material 114 comprises a plurality of labels 118. In at least one embodiment, labels 118 are die cut in label material 114. In at least one embodiment of the present disclosure, label material 114 comprises twenty-four labels 118, each having dimensions of about 1"×2.5". Other sizes and quantities of labels 118 are possible.

In the embodiment of wristband label sheet 110 shown in FIG. 2A, label material 114 comprises release patch 128 and release patch 130. Release patches 128, 130 comprise areas of a release coating (such as, for example, a silicone) applied to the surface of label material 114, to allow the removable adherence of wristband 132 to label sheet 114, as discussed herein. In at least one embodiment of the present disclosure, release patches 128, 130 comprise free radical ultraviolet cured silicone. In at least one embodiment of the present disclosure, release patches 128, 130 comprise a cationic ultraviolet cured release coating. Alternatively, any type of coating (including no-silicone coatings) that permits the removable adherence of wristband 132 to label sheet 114 may be used.

Also shown in the embodiment of wristband label sheet 110 shown in FIG. 2A is wristband 132. In at least one embodiment of the present disclosure, wristband 132 is constructed of a polyester material, although other materials suitable for the intended use of wristband 132 may be used. In at least one embodiment of the present disclosure, wristband 132 has dimensions of about 1"×10.75", however wristband 132 may be of any size that fits on label sheet 112.

Figure 2B:
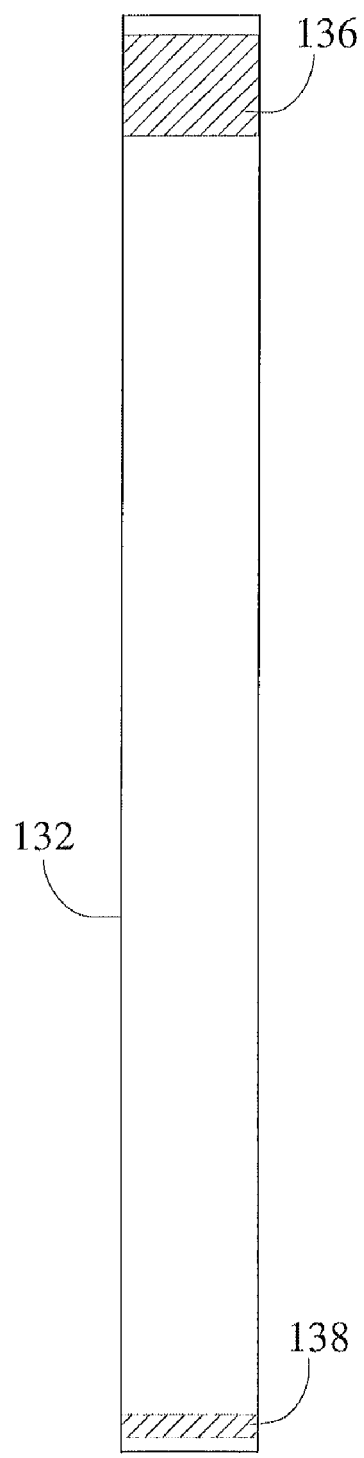
FIG. 2B shows the underside of a wristband according to at least one embodiment of the present disclosure.

FIG. 2B shows the underside of wristband 132 before attachment to label sheet 112, according to at least one embodiment of the present disclosure. Shown in FIG. 2B are wristband 132 comprising adhesive stripe 136 and adhesive stripe 138. In at least one embodiment of the present disclosure, adhesive stripes 136, 138 comprise a layer of a hot melt adhesive.

Referring back to FIG. 2A, shown therein are the locations of adhesive stripes 136, 138 on the underside of wristband 132. Adhesive stripe 136 is interposed between wristband 132 and release patch 128 and removably adheres wristband 132 to release patch 128. Adhesive stripe 138 is interposed between wristband 132 and release patch 130 and removably adheres wristband 132 to release patch 130. As discussed herein, adhesive stripes 136, 138 are operable to secure wristband 132 around a subject's wrist after wristband 132 is removed from label sheet 112.

In at least one alternative embodiment of the present disclosure, adhesive stripes 136, 138 comprise a repositionable adhesive. In such an embodiment release patches 128, 130 may be omitted from wristband label sheet 110.

Indicia may be marked or printed on the top side of wristband 132. For example, the top side of wristband 132 may be exposed to an ink jet printer, a laser print, or another type of printing device capable of applying indicia to the top side of wristband 132. Indicia may be printed on wristband 132 before, after, or concurrently with the printing of indicia on label material 114. The inks, toners, and/or other printing materials used in the application of indicia to the top side of wristband 132 are selected to be compatible with the printing device used to apply such indicia, the material used for wristband 132, and the intended use of wristband 132.

Figure 2C:
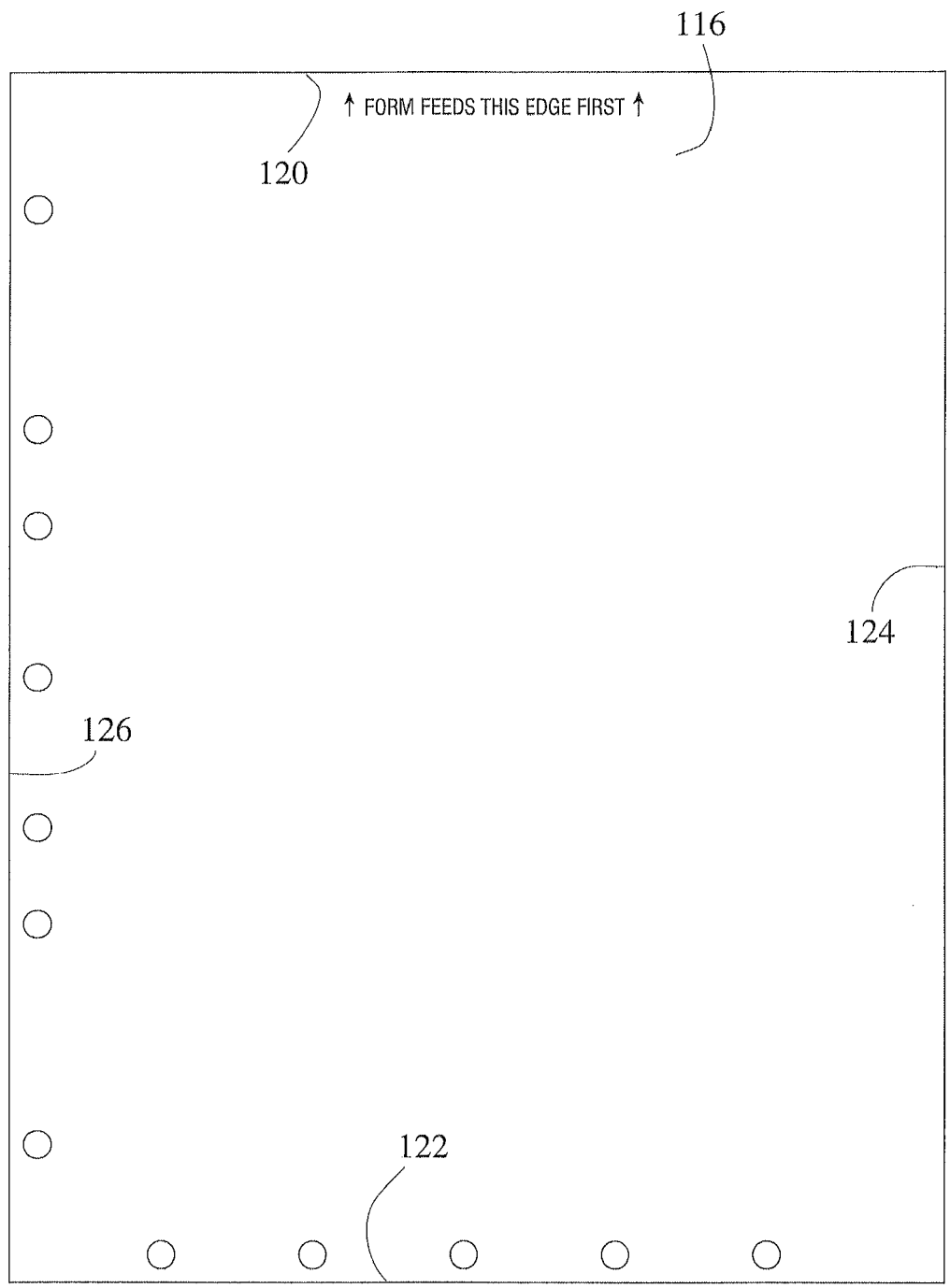
FIG. 2C shows a bottom view of wristband label sheet according to at least one embodiment of the present disclosure.

FIG. 2C shows a bottom view of wristband label sheet 110 of FIG. 2A. Shown in FIG. 2C is liner 116, bounded by leading edge 120, trailing edge 122, side edge 124, and side edge 126.

Figure 3:
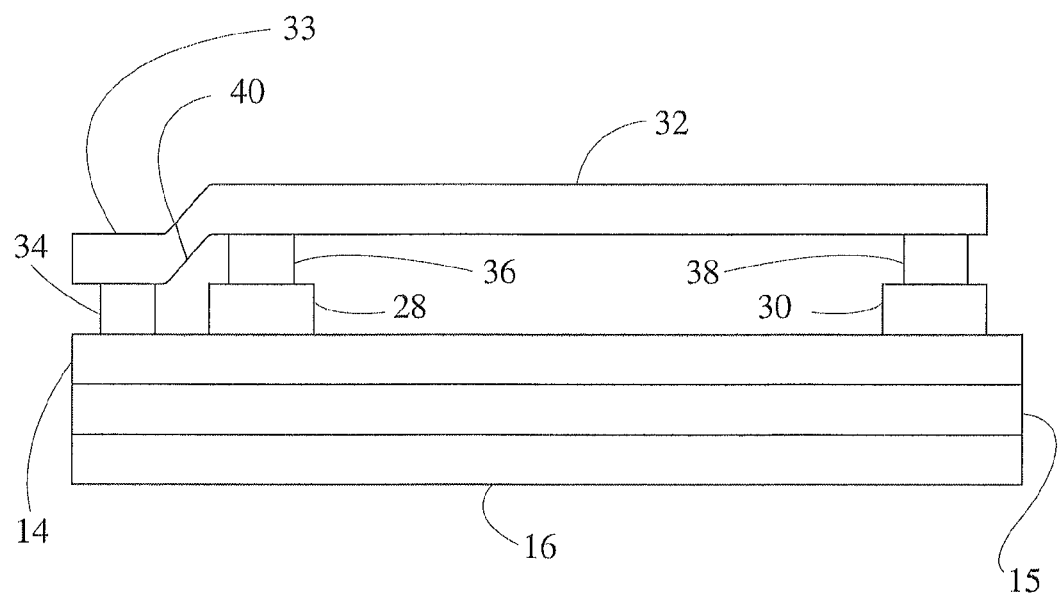
FIG. 3 shows a cross-sectional view of an embodiment of a wristband label sheet according to at least one embodiment of the present disclosure.

FIG. 3 shows a cross-sectional view of the embodiment of wristband label sheet 10 of FIG. 1A taken on line of FIG. 1A, with the proportions enhanced for purposes of clarity. Shown in FIG. 3 are label material 14, adhesive layer 15, liner material 16, release patch 28, release patch 30, wristband 32, stub 33, adhesive stripe 34, adhesive stripe 36, adhesive stripe 38, and line of weakness 40.

Figure 4:
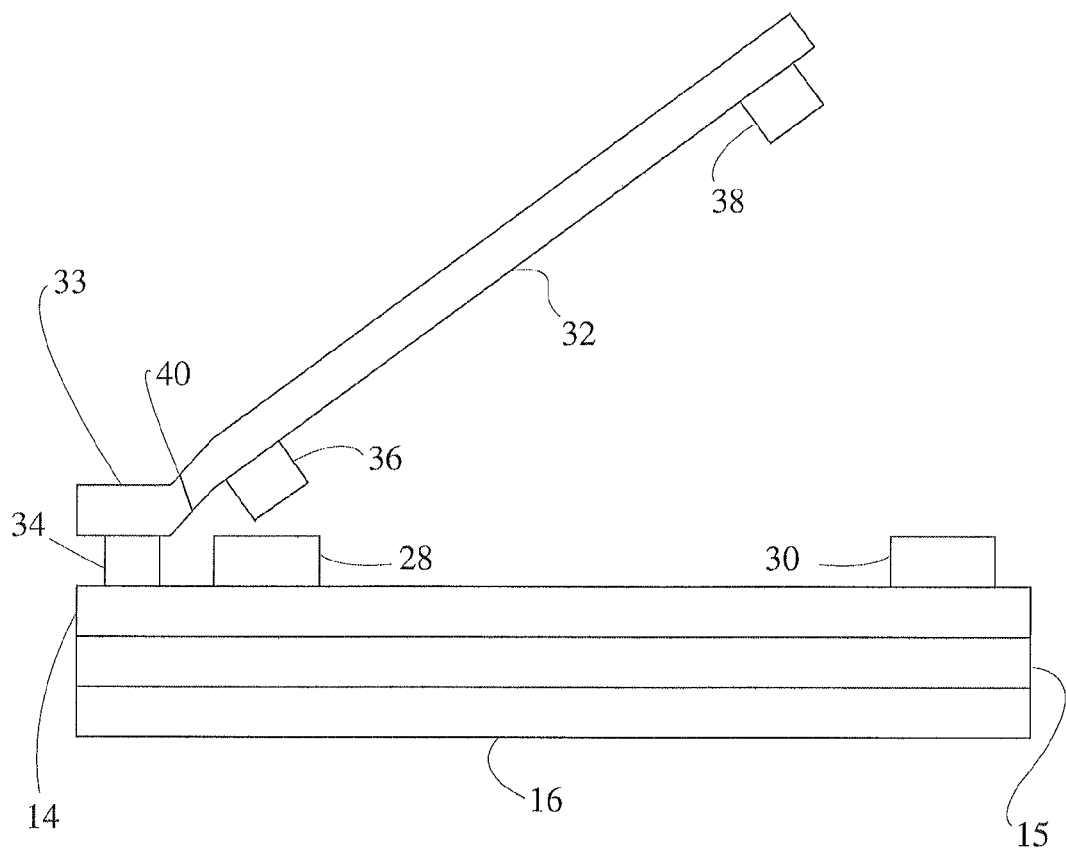
FIG. 4 shows a cross-sectional view of an embodiment of a wristband label sheet according to at least one embodiment of the present disclosure.

According to at least one embodiment of the present disclosure, wristband 32 is removable from label sheet 12 by grasping wristband 32 between adhesive stripe 36 and adhesive stripe 38 and pulling wristband 32 away from label sheet 12. FIG. 4 shows a cross-sectional view of an embodiment of wristband label sheet 10 according to at least one embodiment of the present disclosure, with the proportions enhanced for purposes of clarity. As shown in FIG. 4, wristband 32 is partially separated from label sheet 12. As shown in FIG. 4, adhesive stripe 36 and adhesive stripe 38 have separated from release patch 28 and release patch 30, respectively. Release patch 28 and release patch 30 remain on the top surface of label material 14. Adhesive stripe 36 and adhesive stripe 38 remain adhered to the underside of wristband 32. Stub 33 remains adhered to the top surface of label material 14 by adhesive stripe 34. Wristband 32 remains attach to stub 33 at line of weakness 40.

Figure 5:
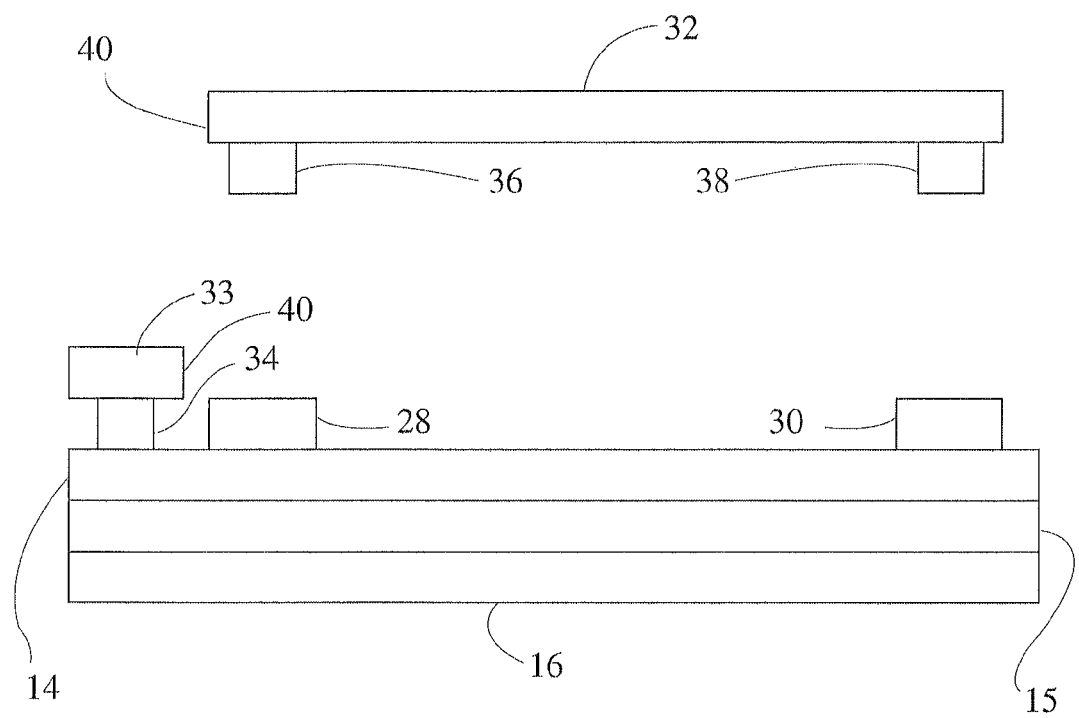
FIG. 5 shows a cross-sectional view of an embodiment of a wristband label sheet according to at least one embodiment of the present disclosure.

FIG. 5 shows a cross-sectional view of an embodiment of wristband label sheet 10 according to at least one embodiment of the present disclosure, with the proportions enhanced for purposes of clarity. As shown in FIG. 5, wristband 32 is fully separated from label sheet 12, and wristband 32 is separated from stub 33 at line of weakness 40. Stub 33 remains adhered to the top surface of label material 14 by adhesive stripe 34. As shown in FIG. 5, adhesive stripes 36, 38 remain adhered to the underside of wristband 32, and release patch 28 and release patch 30 remain adhered to label material 14.

Figure 6:
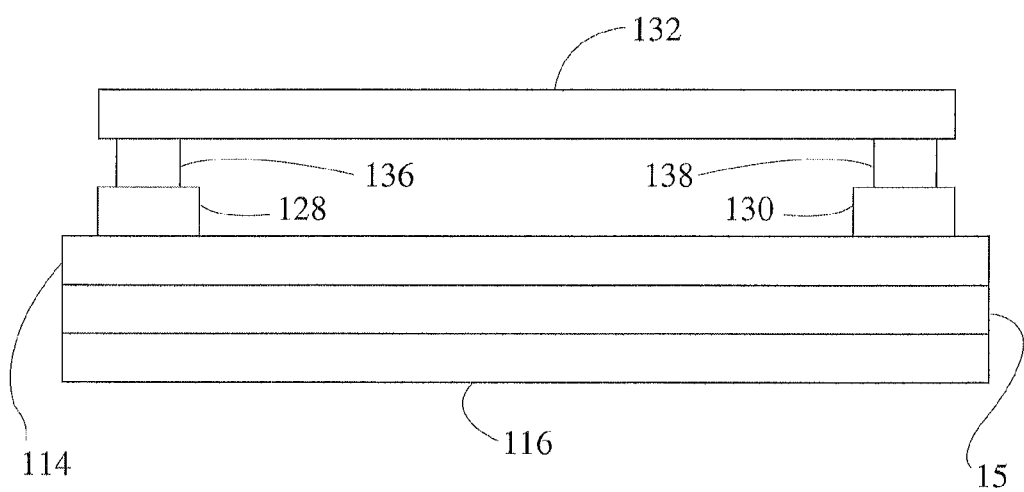
FIG. 6 shows a cross-sectional view of an embodiment of a wristband label sheet according to at least one embodiment of the present disclosure.

FIG. 6 shows a cross-sectional view of the embodiment of wristband label sheet 110 of FIG. 2A taken on line VI-VI of FIG. 2A, with the proportions enhanced for purposes of clarity. Shown in FIG. 6 are label material 114, adhesive layer 115, liner material 116, release patch 128, release patch 130, wristband 132, adhesive stripe 136, and adhesive stripe 138.

Figure 7:
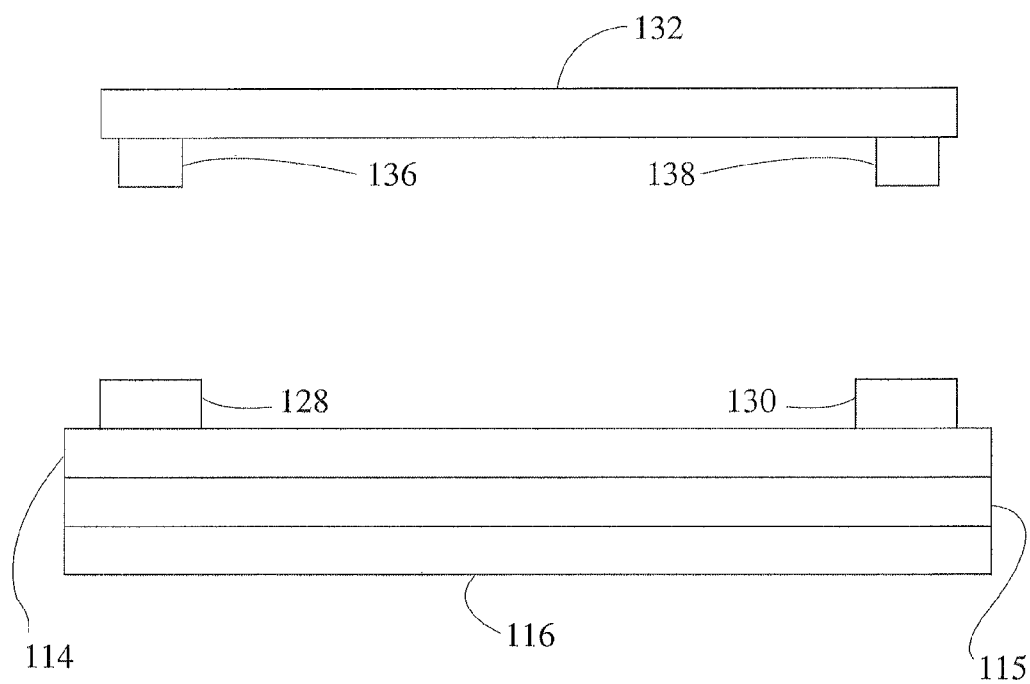
FIG. 7 shows a cross-sectional of an embodiment of a wristband label sheet according to at least one embodiment of the present disclosure.

According to at least one embodiment of the present disclosure, wristband 132 is removable from label sheet 112 by grasping wristband 132 between adhesive stripe 136 and adhesive stripe 138 and pulling wristband 132 away from label sheet 112. FIG. 7 shows a cross-sectional view of an embodiment of wristband label sheet 110 according to at least one embodiment of the present disclosure, with the proportions enhanced for purposes of clarity. As shown in FIG. 7, wristband 132 is separated from label sheet 112. As shown in FIG. 7, adhesive stripe 136 and adhesive stripe 138 have separated from release patch 128 and release patch 130, respectively. Release patch 128 and release patch 130 remain on the top surface of label material 114. Adhesive stripe 136 and adhesive stripe 138 remain adhered to the underside of wristband 132.

Figure 8A:
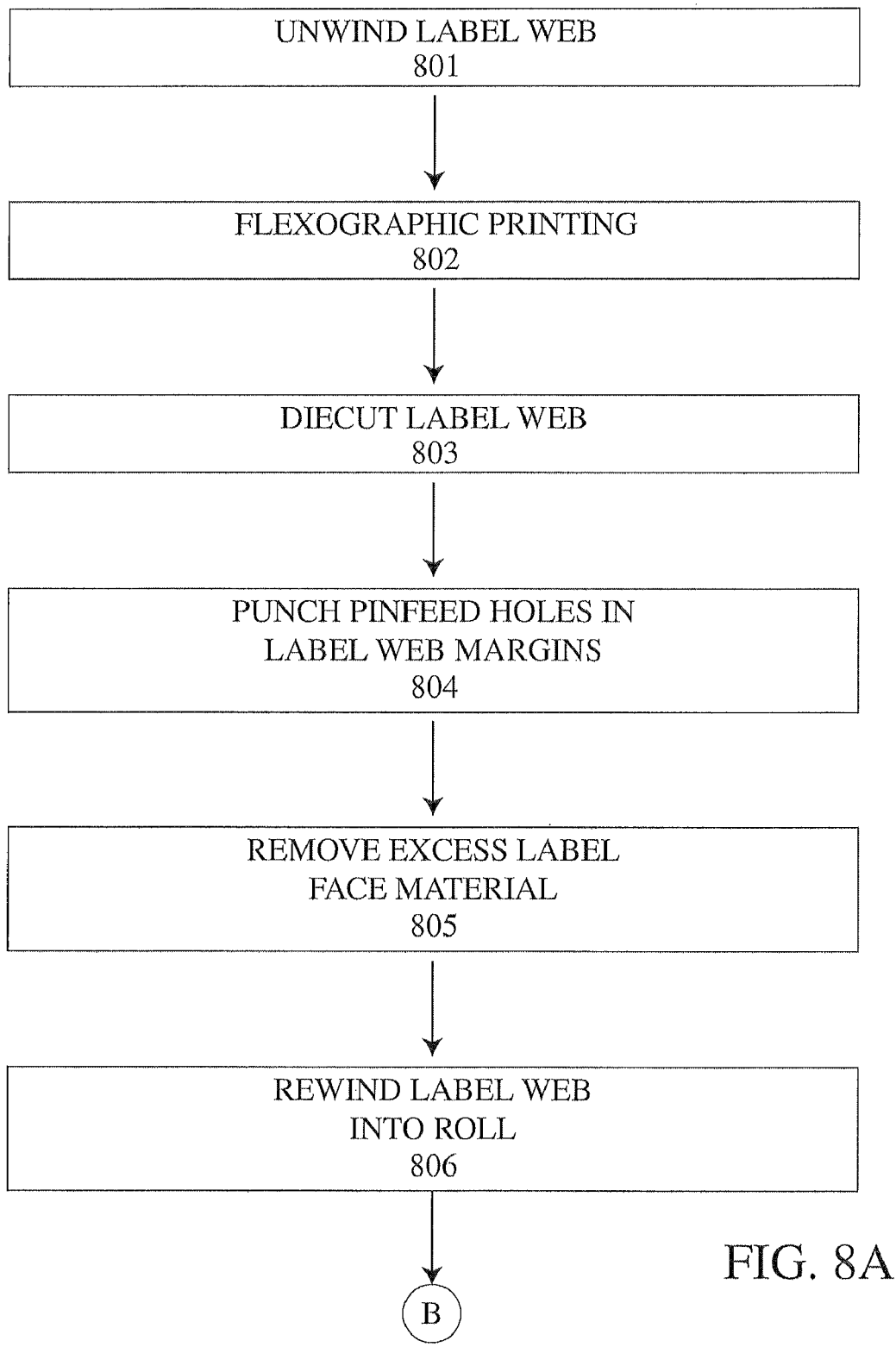
FIGS. 8A-C shows a flowchart for a process for manufacturing a wristband label sheet according to at least one embodiment of the present disclosure.
Figure 8B:
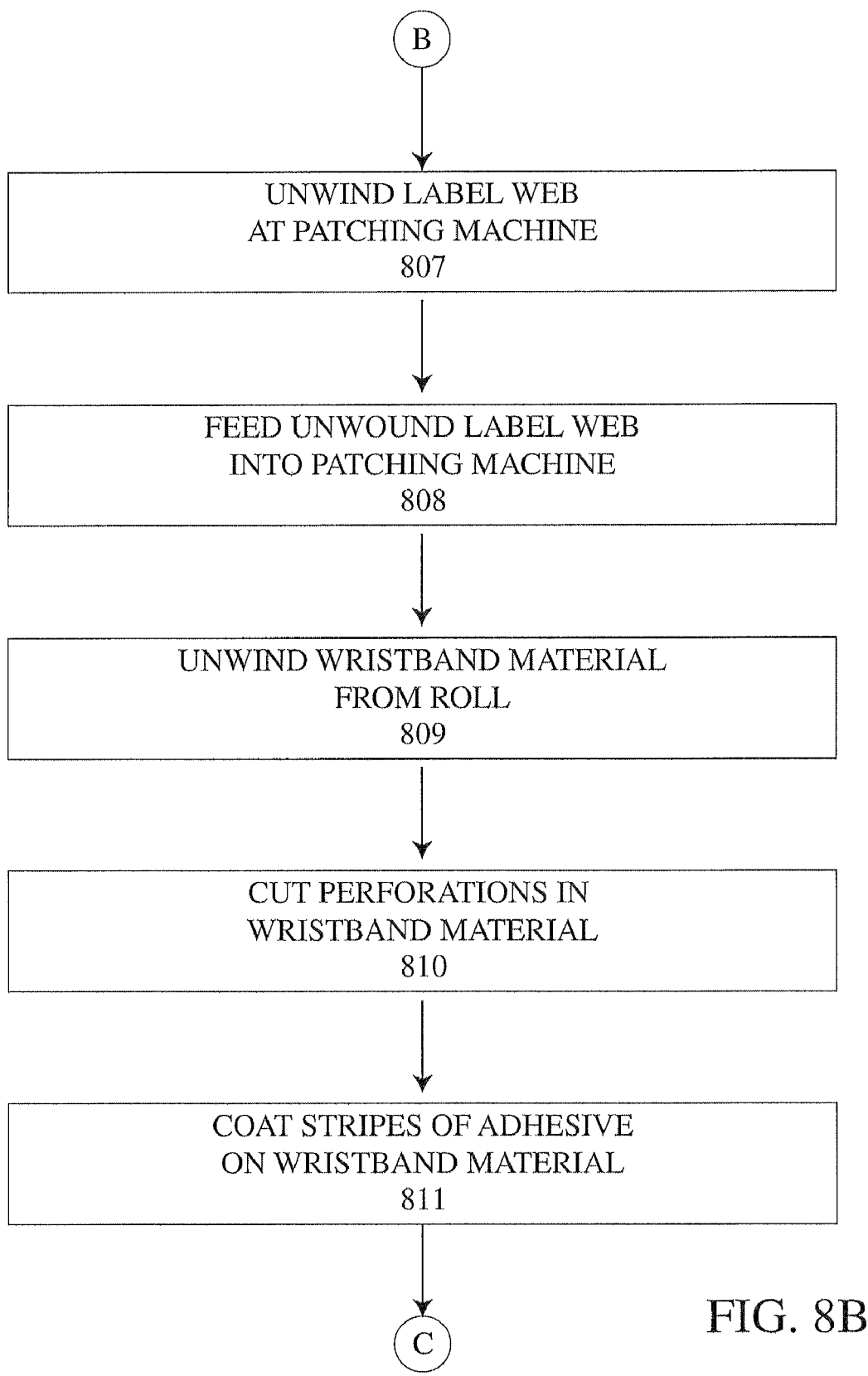
Figure 8C:
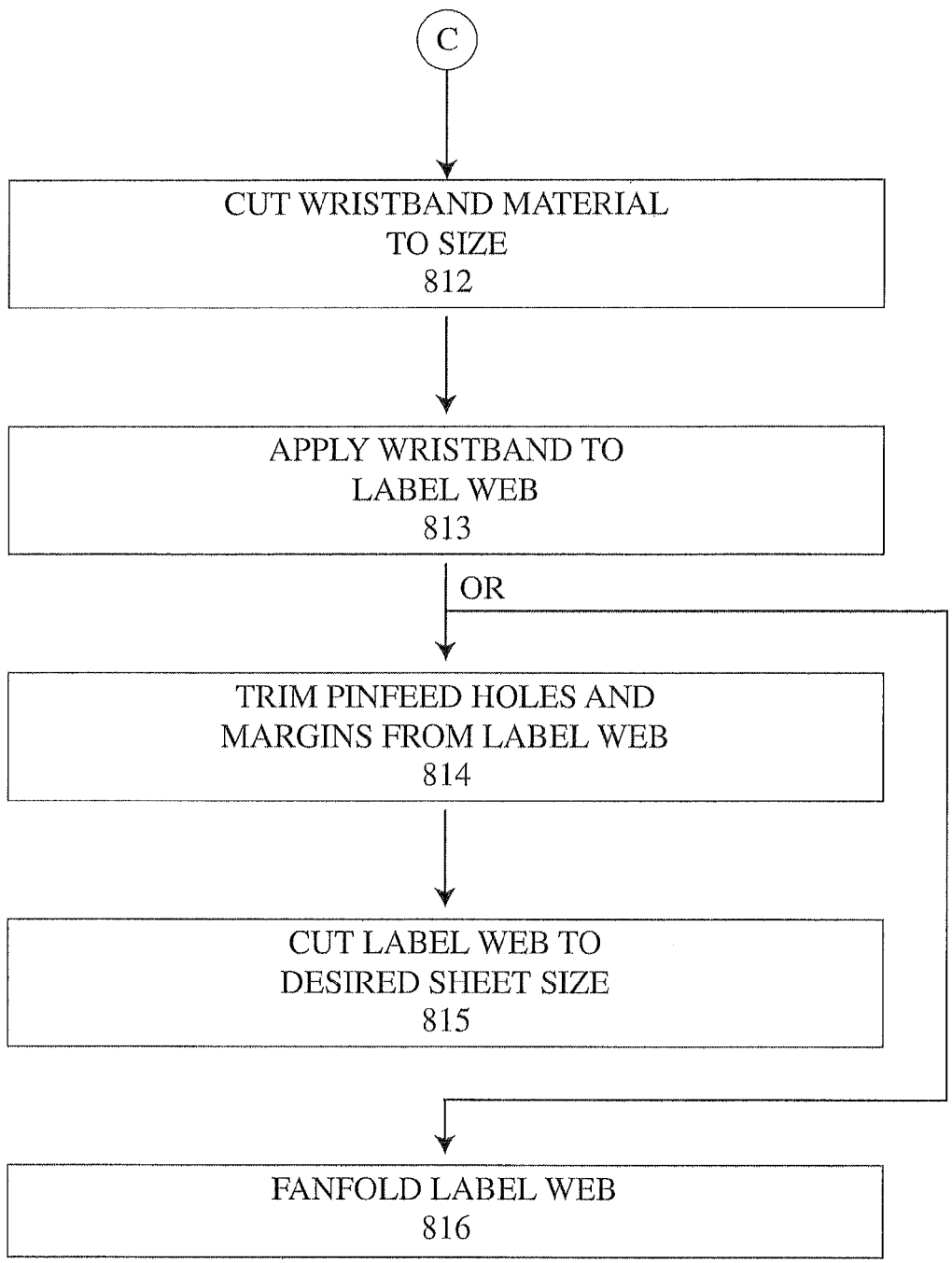

FIGS. 8A-C shows a flowchart illustrating a process for manufacturing a wristband label sheet according to at least one embodiment of the present disclosure.

In step 801 of the embodiment of the present disclosure shown in FIG. 8A, a web of label material comprising a silicone coated liner, label face material, and a pressure sensitive adhesive interposed between the silicone coated liner and label face material, is unwound from a roll and fed mechanically into one or more flexographic printing presses. According to at least on embodiment of the present disclosure, the web of label material comprises an edge margin of at least about ½" on each edge, such that the overall width of web of label material is 1" greater than the desired width of the finished product.

Alternatively, separate webs of liner material and label face material may be unwound from a roll and fed mechanically into a process by which a pressure sensitive adhesive is applied to either the liner material or label face material, and then the liner material and label face material are laminated to together with the pressure sensitive adhesive interposed between the liner material and label face material. In such an application the pressure sensitive adhesive may be coated edge to edge or it may be coated in a pattern with voids of adhesive where required.

In step 802 of the embodiment of the present disclosure shown in FIG. 8A, one or more flexographic printing presses apply one or more release patches comprising silicone or another type of release coating to the surface of the label face material. Such flexographic printing presses also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 8A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 803 of the embodiment of the present disclosure shown in FIG. 8A, after the flexographic printing step, the web of label material then travels through rotary die stations, where the web of label material can be die cut to create multiple labels, label cavities, slits, peel tabs, lines of weakness, perforations, punched holes for insertion into binders or folders, or any other specified die cutting. Such die cutting may be die cutting of the label face material only, the liner material only, or both the label face material and the liner material.

In step 804 of the embodiment of the present disclosure shown in FIG. 8A, the web of label material proceeds to a punching station where pinfeed holes are punched in ½" margins at each edge of the web of label material, to facilitate registration of the web of label material in the process during which wristbands are applied to the web of label material (discussed hereinafter).

In step 805 of the embodiment of the present disclosure shown in FIG. 8A, if required for the wristband label sheet design, portions of the label face material are removed. For example, it may be required for the wristband label sheet design that the border comprising the outer edges of the label face material be removed prior to delivery to a customer. In such a case, the border can be separated from the portion of the label face material that is desired to remain by a die cut through the label face material only, and then the waste at the border of the label face material can be peeled off at a waste removal station and then wound on a waste roll or sucked away by a vacuum removal system.

In step 806 of the embodiment of the present disclosure shown in FIG. 8A, after printing of release patches, die cutting, and punching of pinfeed holes, the web of label material is rewound onto rolls that will be furnished to the patching machine process.

In step 807 of the embodiment of the present disclosure shown in FIG. 8B, the rolled web of label material from step 807 is unwound and fed into a patching machine, wherein one or more wristbands will be applied to the web of label material.

In at least one alternative embodiment of the present disclosure, the steps shown as step 806 and step 807 of the embodiment of the present disclosure shown in FIG. 8B may be omitted. In such an embodiment, the web of label material proceeds to step 808 of the embodiment of the present disclosure shown in FIG. 8B.

In step 808 of the embodiment of the present disclosure shown in FIG. 8B, the punched pinfeed holes in the web of label material engage with a pinfeed mechanism of the patching machine. The pinfeed mechanism of the patching machine pulls the web of label material into and through the patching machine by pins that penetrate the previously punched pinfeed holes and rotate on gear driven shafts to drive the web of label material through the patching machine at a predetermined feed rate.

In step 809 of the embodiment of the present disclosure shown in FIG. 8B, a roll of wristband material (such as, for example, a roll of a polyester material) is unwound mechanically and fed into the patching machine. According to at least on embodiment of the present disclosure, the width of the wristband material on the roll of wristband material is the same as the desired width of the wristband to be applied to applied to the web of label material (discussed hereinafter).

In step 810 of the embodiment of the present disclosure shown in FIG. 8B, if required for the wristband label sheet design, lines of weakness are cut into the unrolled wristband material at a perforating station.

In step 811 of the embodiment of the present disclosure shown in FIG. 8B, the patching machine coats one or more stripes of adhesive on the underside the web of wristband material polyester at an adhesive coating station.

In step 812 of the embodiment of the present disclosure shown in FIG. 8C, the patching machine cuts each wristband to a predetermined length. For example, if the finished product required a 1" long wristband, the patching machine cuts off a 1" length of wristband material from the roll of wristband material. In an exemplary embodiment where a 1" long, 10.75" wide wristband is to be applied to an 8.5" long label sheet, the 10.75" wide web of wristband material is fed by computer controlled nip type feed rollers at a rate of 1" for every 8.5" of label material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

In step 813 of the embodiment of the present disclosure shown in FIG. 8C, after the wristband is cut to length, the vacuum cylinder carries each cut-off wristband to an impression roller that is wrapped by the web of label material. At the impression roller the wristband is transferred from the vacuum cylinder to the face of the web of label material. The wristband is applied such that one or more of the adhesive stripes on the underside of the wristband are aligned with one or more of the release patches on the label face material. The wristband is adhered to the web of label material by the adhesive stripes that were applied to the underside of the wristband. The patching machine comprises gearing that keeps the cutting cylinder and vacuum cylinder in time with the pace at which the patching machine's pinfeed mechanism moves the web of label material.

In step 814 of the embodiment of the present disclosure shown in FIG. 8C, if required for the wristband label sheet design, the ½" margins (including the pinfeed holes) are mechanically trimmed off of the web of label material at a trimming station.

In step 815 of the embodiment of the present disclosure shown in FIG. 8C, if required for the wristband label sheet design, the web of label material including the applied wristband is mechanically cut into sheets at a sheeter station, with each sheet containing one or more wristbands as required by the wristband label sheet design. The sheets are fed into a batcher/stacker, and then may be shrink-wrapped and packaged. Sheeting is an alternative to the fanfolding step discussed herein.

In step 816 of the embodiment of the present disclosure shown in FIG. 8C, if required for the wristband label sheet design, the web of label material including the applied wristband may be fanfolded in-line with a mechanical folder or by gravity in waterfall fashion, with each fanfold containing one or more wristbands as required by the wristband label sheet design. The wristband label sheet design may require the ½" margins with pinfeed holes to be left on the fanfolded web of label material. Fanfolding is an alternative to the sheeting step discussed above.

Figure 9:
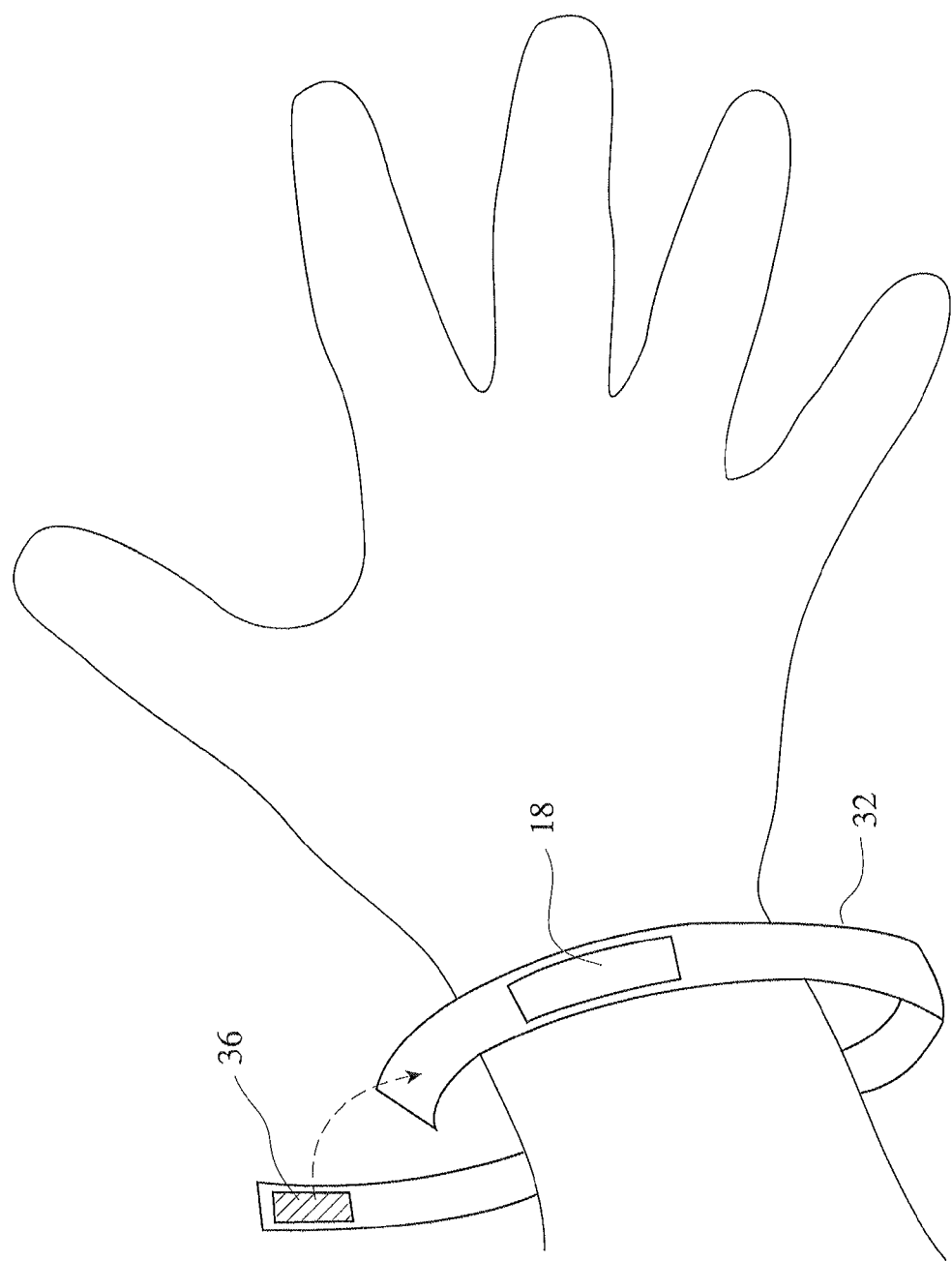
FIG. 9 shows an illustration of at least one embodiment of a wristband according to the present disclosure in use.

FIG. 9 shows at least one embodiment of a wristband according to the present disclosure in use. As shown in FIG. 9, wristband 32 is looped around the wrist of a subject. An exposed adhesive surface of adhesive stripe 38 (not shown) is brought into contact with and adhered to wristband 32 (as shown by arrow 39). After adhesive stripe 38 is adhered to wristband 32, the exposed adhesive surface of adhesive stripe 36 is brought into contact with and adhered to wristband 32

(as shown by arrow 37). The ends of wristband 32 are thereby adhered together and the wristband is secured around the wrist of the subject.

Figure 10A:
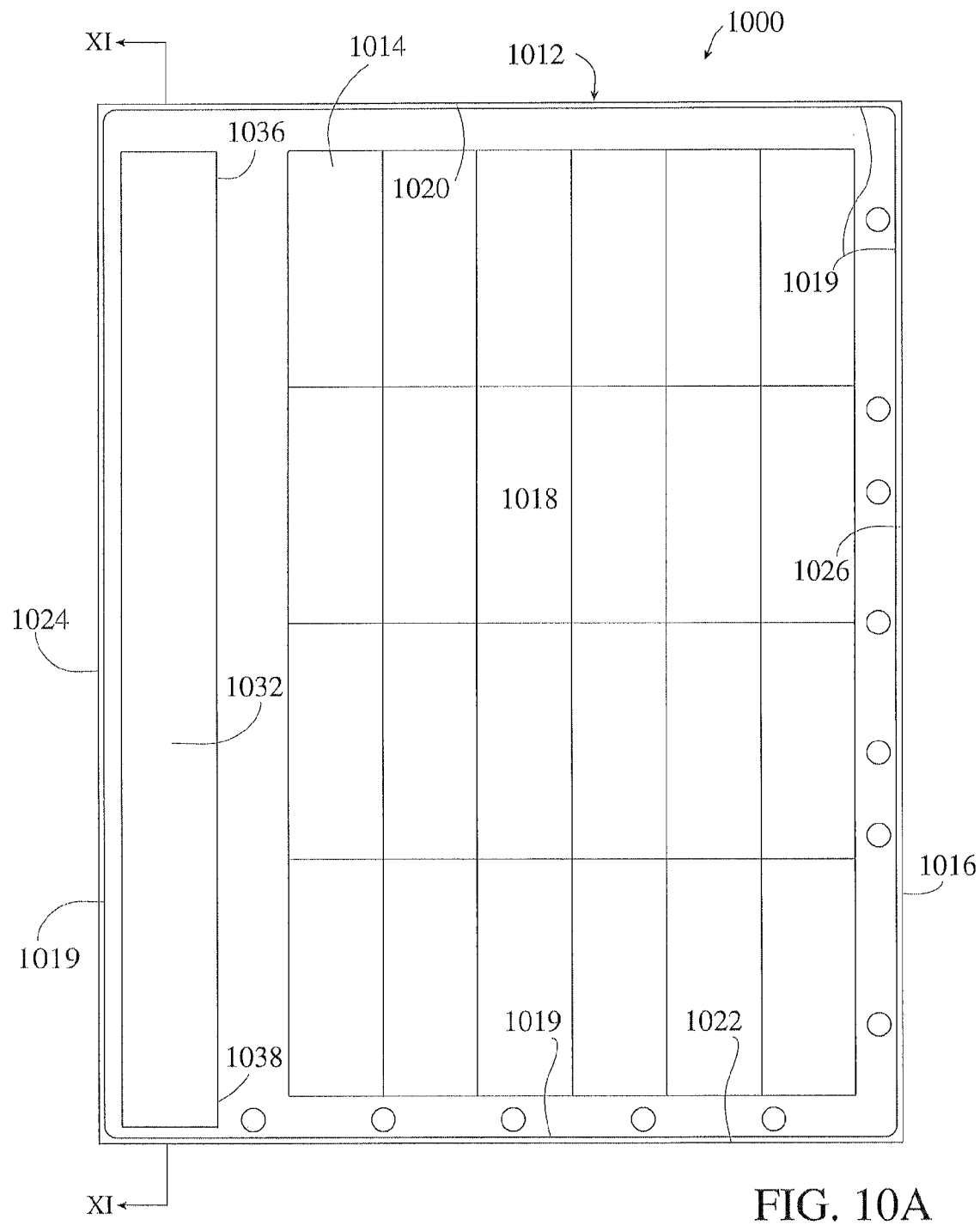
FIG. 10A shows a top view of a wristband label sheet according to at least one embodiment of the present disclosure.

FIG. 10A shows a top view of wristband label sheet 1000 according to at least one embodiment of the present disclosure. Shown in FIG. 10A are label sheet 1012, comprising label material 1014 and liner material 1016. Adhesive 1015 (not shown in FIG. 10A) is interposed between label material 1014 and liner material 1016 and removably adheres label material 1014 to liner material 1016. In at least one embodiment of the present disclosure, liner material 1016 comprises a silicone coating on the surface facing adhesive 1015. In the embodiment of wristband label sheet 1000 shown in FIG. 10A, liner material 1016 is bounded by leading edge 1020, trailing edge 1022, side edge 1024, and side edge 1026. Label sheet 1012 may be of any size. In at least one embodiment of label sheet 1012 according to the present disclosure, the outer dimensions of label sheet 1012 are selected to enable label sheet 1012 to fit in a commercially available printing device. For example, in such an embodiment, the outer dimensions of label sheet 1012 may be 8½"×11", 8½"×14", or 210 mm×297 mm.

In at least one embodiment of the present disclosure, label material 1014 comprises perimeter 1019 defining a boundary of label material 1014. In at least one embodiment of the present disclosure, at least a portion of perimeter 1019 is inboard of the boundary formed by leading edge 1020, trailing edge 1022, side edge 1024, and side edge 1026. In at least one embodiment of the present disclosure, perimeter 1019 is coextensive with the boundary formed by leading edge 1020, trailing edge 1022, side edge 1024, and side edge 1026.

In at least one embodiment of the present disclosure, label material 1014 comprises a material suitable for the printing of indicia thereon, such as, for example, paper, polyester, or another polymer material. Indicia may be marked or printed on the top side of label material 1014. For example, the top side of label material 1014 may be exposed to an ink jet printer, a laser print, or another type of printing device capable of applying indicia to the top side of label material 1014. The inks, toners, and/or other printing materials used in the application of indicia to the top side of label material 1014 are selected to be compatible with the printing device used to apply such indicia, the material used for label material 1014, and the intended use of wristband label sheet 1000.

In the embodiment of wristband label sheet 1000 shown in FIG. 10A, label material 1014 comprises a plurality of labels 1018. In at least one embodiment, labels 1018 are die cut in label material 1014. In at least one embodiment of the present disclosure, label material 1014 comprises twenty-four labels 1018, each having dimensions of about 1"×2.5". Other sizes and quantities of labels 1018 are possible.

In at least one embodiment of the present disclosure, wristband 1032 is constructed of a polyester material, although other materials suitable for the intended use of wristband 1032 may be used. In at least one embodiment of the present disclosure, wristband 1032 has dimensions of about 1"×10.75", however wristband 1032 may be of any size that fits on label sheet 1012.

Figure 10B:
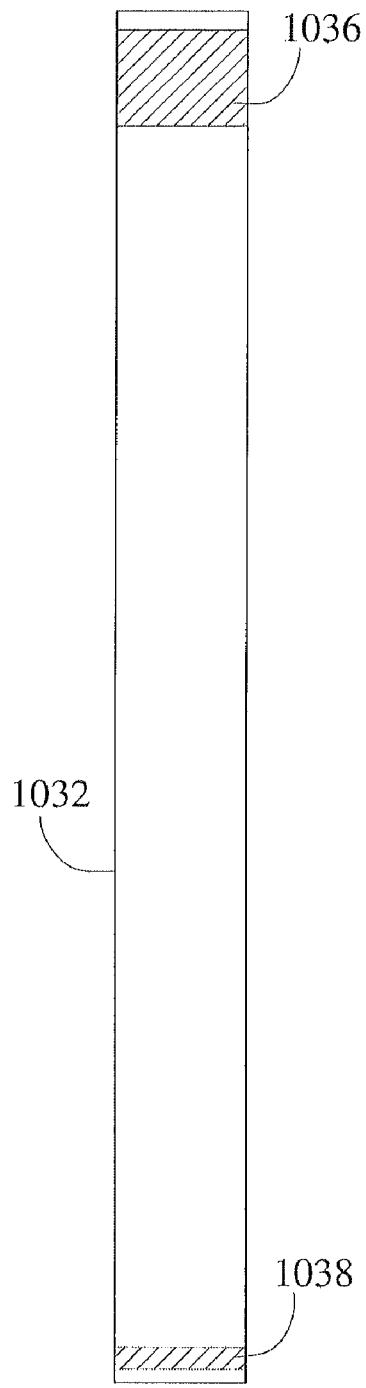
FIG. 10B shows the underside of a wristband according to at least one embodiment of the present disclosure.

FIG. 10B shows the underside of wristband 1032 before attachment to label sheet 1012, according to at least one embodiment of the present disclosure. Shown in FIG. 10B are wristband 1032 comprising adhesive stripe 1036 and adhesive stripe 1038. In at least one embodiment of the present disclosure, adhesive stripes 1036 and 1038 comprise a layer of a repositionable adhesive. In at least one embodiment of the present disclosure, adhesive stripes 1036 and 1038 comprise a layer of a removable adhesive. In at least one embodiment of the present disclosure, adhesive stripes 1036 and 1038 comprise a layer of a pressure sensitive adhesive.

Referring back to FIG. 10A, shown therein are the locations of adhesive stripes 1036, 1038 on the underside of wristband 1032. Adhesive stripe 1036 is interposed between wristband 1032 to label material 1014 and removably adheres wristband 1032 to label material 1014. Adhesive stripe 1038 is interposed between wristband 1032 to label material 1014 and removably adheres wristband 1032 to label material 1014. As discussed herein, adhesive stripes 1036, 1038 are operable to secure wristband 1032 around a subject's wrist after wristband 1032 is removed from label sheet 1012.

Indicia may be marked or printed on the top side of wristband 1032. For example, the top side of wristband 1032 may be exposed to an ink jet printer, a laser print, or another type of printing device capable of applying indicia to the top side of wristband 1032. Indicia may be printed on wristband 1032 before, after, or concurrently with the printing of indicia on label material 1014. The inks, toners, and/or other printing materials used in the application of indicia to the top side of wristband 1032 are selected to be compatible with the printing device used to apply such indicia, the material used for wristband 1032, and the intended use of wristband 1032.

Figure 11:
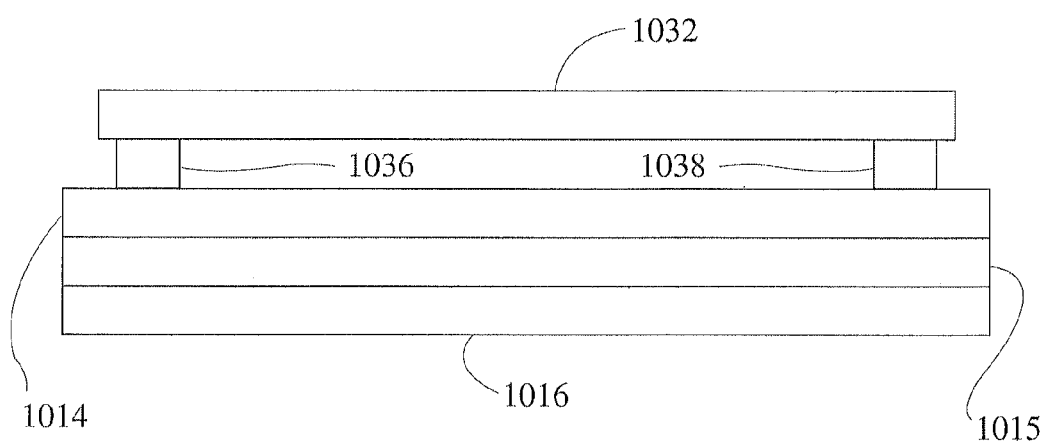
FIG. 11 shows a cross-sectional view of an embodiment of a wristband label sheet according to at least one embodiment of the present disclosure.

FIG. 11 shows a cross-sectional view of the embodiment of wristband label sheet 1000 of FIG. 10A taken on line XI-XI of FIG. 10A, with the proportions enhanced for purposes of clarity. Shown in FIG. 11 are label material 1014, adhesive layer 1015, liner material 1016, wristband 1032, adhesive stripe 1036, and adhesive stripe 1038.

Figure 12:
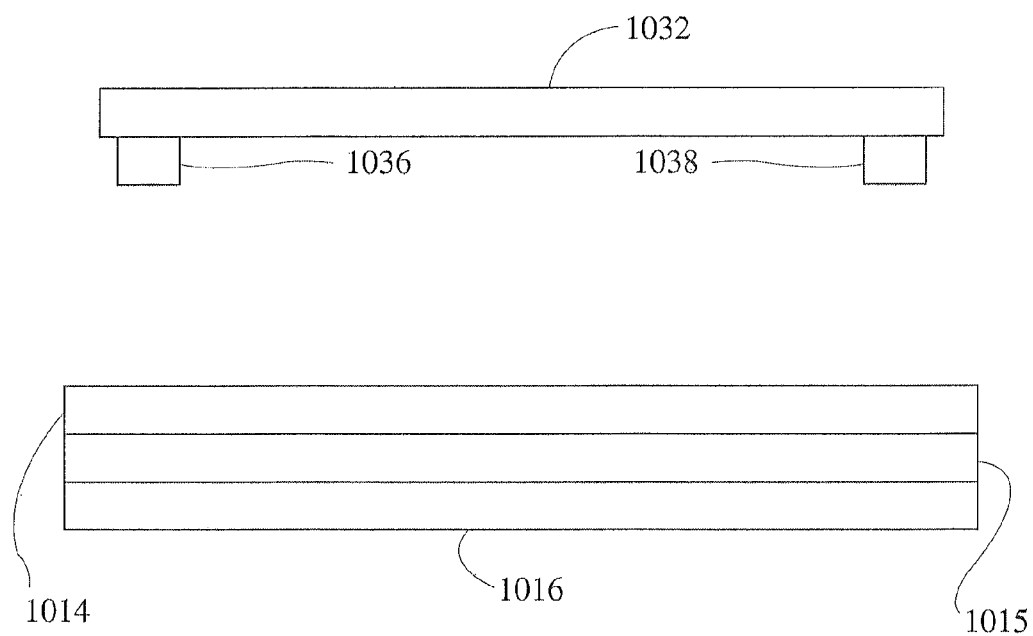
FIG. 12 shows a cross-sectional of an embodiment of a wristband label sheet according to at least one embodiment of the present disclosure.

According to at least one embodiment of the present disclosure, wristband 1032 is removable from label sheet 1012 by grasping wristband 1032 between adhesive stripe 1036 and adhesive stripe 1038 and pulling wristband 1032 away from label sheet 1012. FIG. 12 shows a cross-sectional view of an embodiment of wristband label sheet 1000 according to at least one embodiment of the present disclosure, with the proportions enhanced for purposes of clarity. As shown in FIG. 12, wristband 1032 is separated from label sheet 1012. As shown in FIG. 12, adhesive stripe 1036 and adhesive stripe 1038 have separated from label material 1014. Adhesive stripe 1036 and adhesive stripe 1038 remain adhered to the underside of wristband 1032.

Figure 13A:
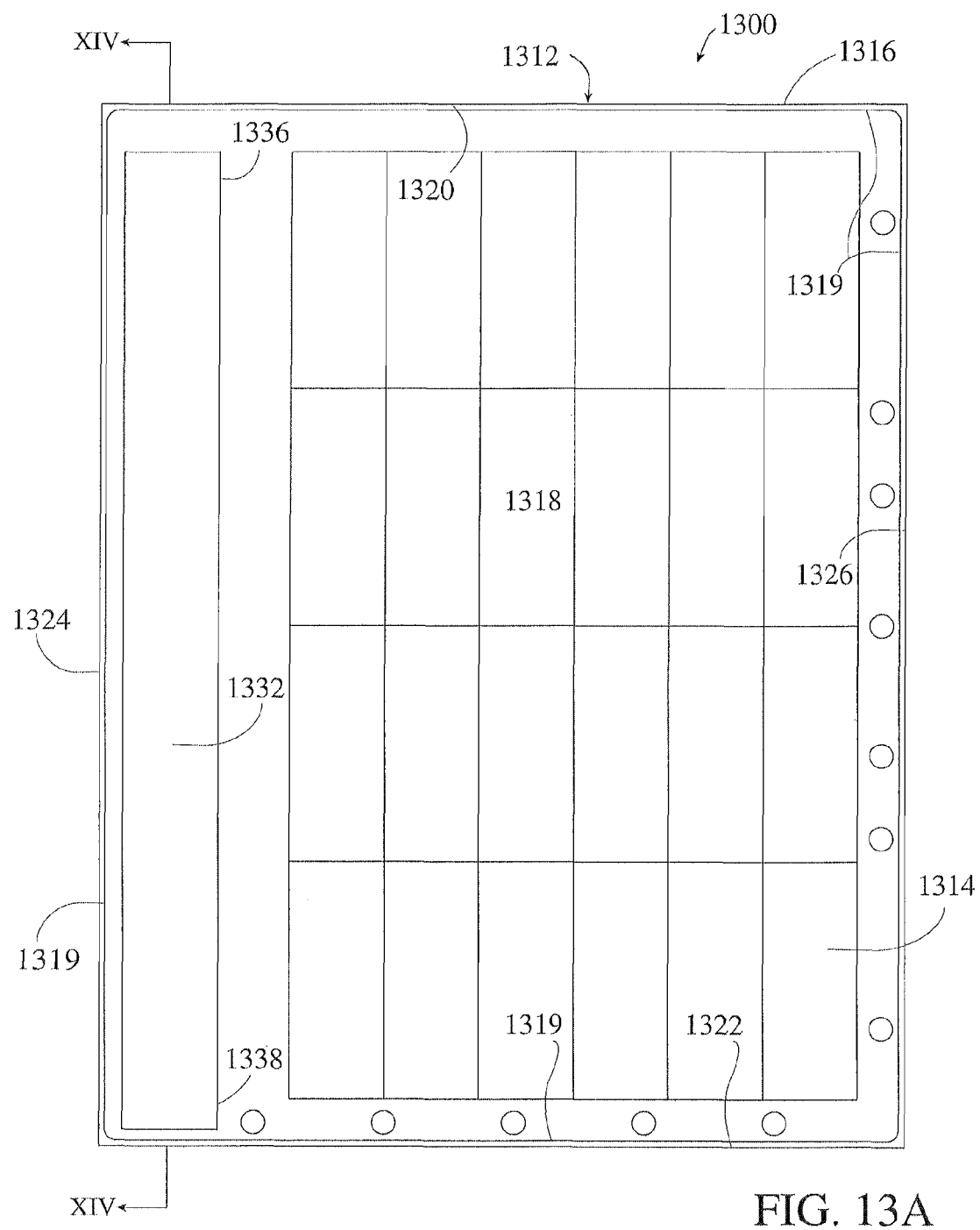
FIG. 13A shows a top view of a wristband label sheet according to at least one embodiment of the present disclosure.

FIG. 13A shows a top view of wristband label sheet 1300 according to at least one embodiment of the present disclosure. Shown in FIG. 13A are label sheet 1312, comprising label material 1314 and liner material 1316. Adhesive 1315 (not shown in FIG. 13A) is interposed between label material 1314 and liner material 1316 and removably adheres label material 1314 to liner material 1316. In at least one embodiment of the present disclosure, liner material 1316 comprises a silicone coating on the surface facing adhesive 1315. In the embodiment of wristband label sheet 1300 shown in FIG. 13A, liner material 1316 is bounded by leading edge 1320, trailing edge 1322, side edge 1324, and side edge 1326. Label sheet 1312 may be of any size. In at least one embodiment of label sheet 1312 according to the present disclosure, the outer dimensions of label sheet 1312 are selected to enable label sheet 1312 to fit in a commercially available printing device. For example, in such an embodiment, the outer dimensions of label sheet 1312 may be 8½"×11", 8½"×14", or 210 mm×297 mm.

In at least one embodiment of the present disclosure, label material 1314 comprises perimeter 1319 defining a boundary of label material 1314. In at least one embodiment of the present disclosure, at least a portion of perimeter 1319 is inboard of the boundary formed by leading edge 1320, trailing edge 1322, side edge 1324, and side edge 1326. In at least one embodiment of the present disclosure, perimeter 1319 is coextensive with the boundary formed by leading edge 1320, trailing edge 1322, side edge 1324, and side edge 1326.

In at least one embodiment of the present disclosure, label material 1314 comprises a material suitable for the printing of indicia thereon, such as, for example, paper, polyester, or another polymer material. Indicia may be marked or printed on the top side of label material 1314. For example, the top side of label material 1314 may be exposed to an ink jet printer, a laser print, or another type of printing device capable of applying indicia to the top side of label material 1314. The inks, toners, and/or other printing materials used in the application of indicia to the top side of label material 1314 are selected to be compatible with the printing device used to apply such indicia, the material used for label material 1314, and the intended use of wristband label sheet 1300.

In the embodiment of wristband label sheet 1300 shown in FIG. 13A, label material 1314 comprises a plurality of labels 1318. In at least one embodiment, labels 1318 are die cut in label material 1314. In at least one embodiment of the present disclosure, label material 1314 comprises twenty-four labels 1318, each having dimensions of about 1"×2.5". Other sizes and quantities of labels 1318 are possible.

In at least one embodiment of the present disclosure, wristband 1332 is constructed of a polyester material, although other materials suitable for the intended use of wristband 1332 may be used. In at least one embodiment of the present disclosure, wristband 1332 has dimensions of about 1"×10.75", however wristband 1332 may be of any size that fits on label sheet 1312.

Figure 13B:
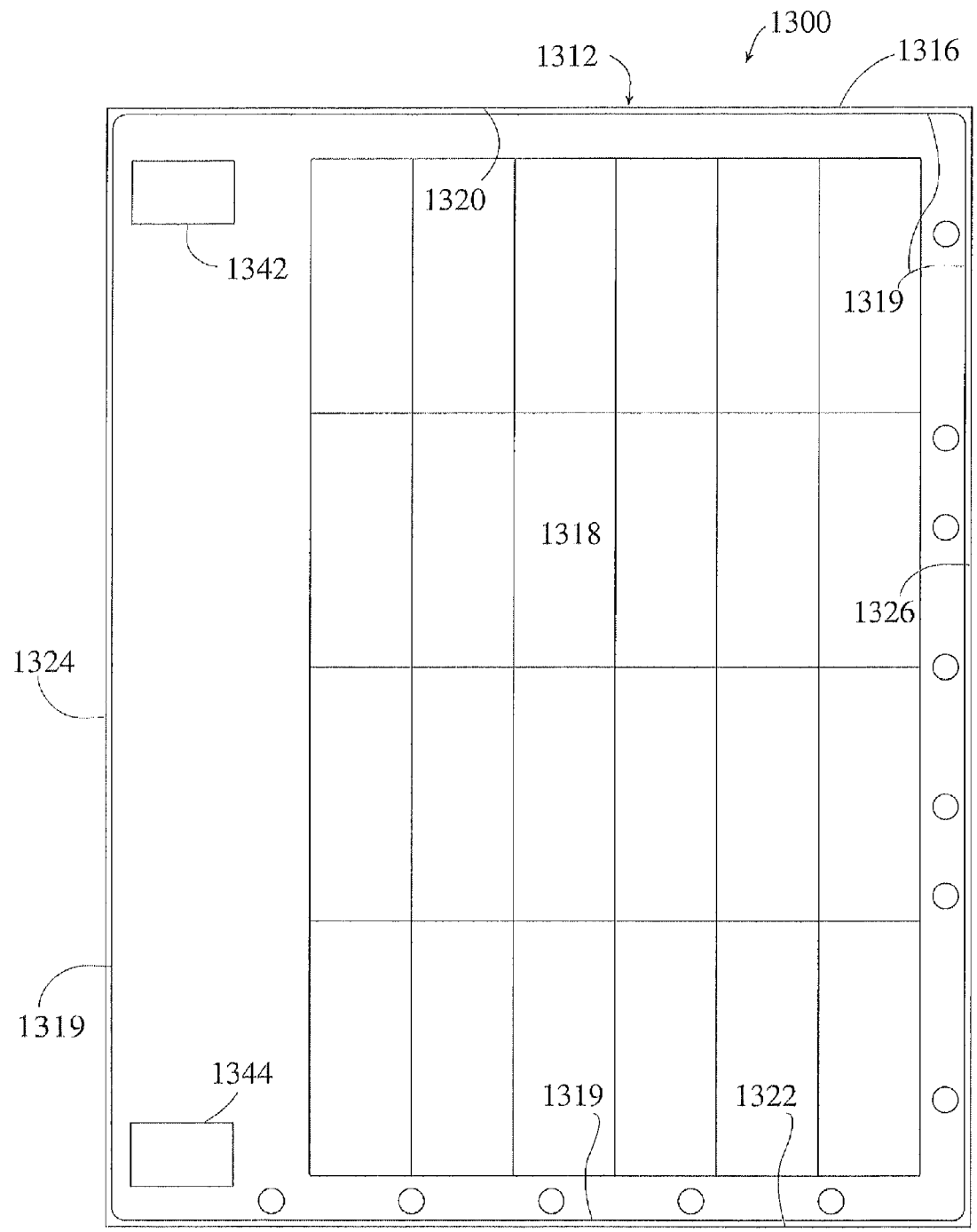
FIG. 13B shows a top view of a label sheet according to at least one embodiment of the present disclosure.

FIG. 13B shows a top view of wristband label sheet 1300 according to at least one embodiment of the present disclosure without the application of wristband 1332. Shown in FIG. 13B are patches 1342 and 1344. In at least one embodiment, patches 1342 and 1344 are die cut in label material 1314.

Referring back to FIG. 13A, shown therein are the locations of adhesive stripes 1336, 1338 on the underside of wristband 1332. Adhesive stripe 1336 is interposed between wristband 1332 and patch 1342 and adheres wristband 1332 to label material 1314. Adhesive stripe 1338 is interposed between wristband 1332 and patch 1344 and adheres wristband 1332 to label material 1314.

Indicia may be marked or printed on the top side of wristband 1332. For example, the top side of wristband 1332 may be exposed to an ink jet printer, a laser print, or another type of printing device capable of applying indicia to the top side of wristband 1332. Indicia may be printed on wristband 1332 before, after, or concurrently with the printing of indicia on label material 1314. The inks, toners, and/or other printing materials used in the application of indicia to the top side of wristband 1332 are selected to be compatible with the printing device used to apply such indicia, the material used for wristband 1332, and the intended use of wristband 1332.

Figure 14:
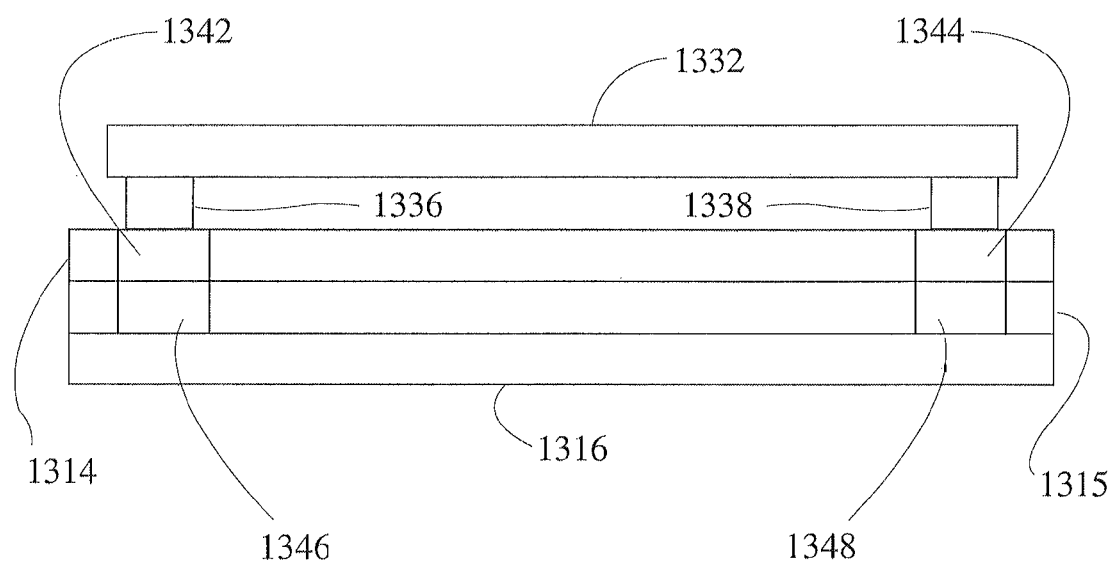
FIG. 14 shows a cross-sectional view of an embodiment of a wristband label sheet according to at least one embodiment of the present disclosure.

FIG. 14 shows a cross-sectional view of the embodiment of wristband label sheet 1300 of FIG. 13A taken on line XIV-XIV of FIG. 13A, with the proportions enhanced for purposes of clarity. Shown in FIG. 14 are label material 1314, adhesive layer 1315, liner material 1316, wristband 1332, adhesive stripe 1336, adhesive stripe 1338, patch 1342, patch 1344, adhesive deposit 1346, and adhesive deposit 1348.

Figure 15:
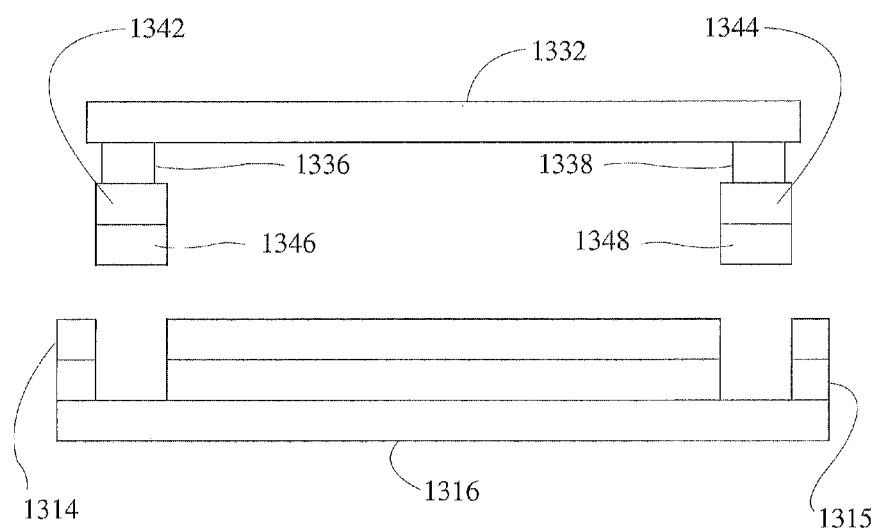
FIG. 15 shows a cross-sectional of an embodiment of a wristband label sheet according to at least one embodiment of the present disclosure.

According to at least one embodiment of the present disclosure, wristband 1332 is removable from label sheet 1312 by grasping wristband 1332 between adhesive stripe 1336 and adhesive stripe 1338 and pulling wristband 1332 away from label sheet 1312. FIG. 15 shows a cross-sectional view of an embodiment of wristband label sheet 1300 according to at least one embodiment of the present disclosure, with the proportions enhanced for purposes of clarity. As shown in FIG. 15, wristband 1332 is separated from label sheet 1312. As shown in FIG. 15, adhesive stripe 1336 and adhesive stripe 1338 remain adhered to the underside of wristband 1332. As shown in FIG. 15, patch 1342 remains adhered to adhesive stripe 1336 and patch 1344 remains adhered to adhesive stripe 1338 after wristband 1332 is separated from label sheet 1312. Adhesive layer 1315 comprises adhesive deposit 1346 and adhesive deposit 1348. As shown in FIG. 15, when wristband 1332 is separated from label sheet 1312 along with adhesive stripe 1336, adhesive stripe 1338, patch 1342, and patch 1344, adhesive deposit 1346 remains adhered to patch 1342 and adhesive deposit 1348 remains adhered to patch 1344.

Figure 16:
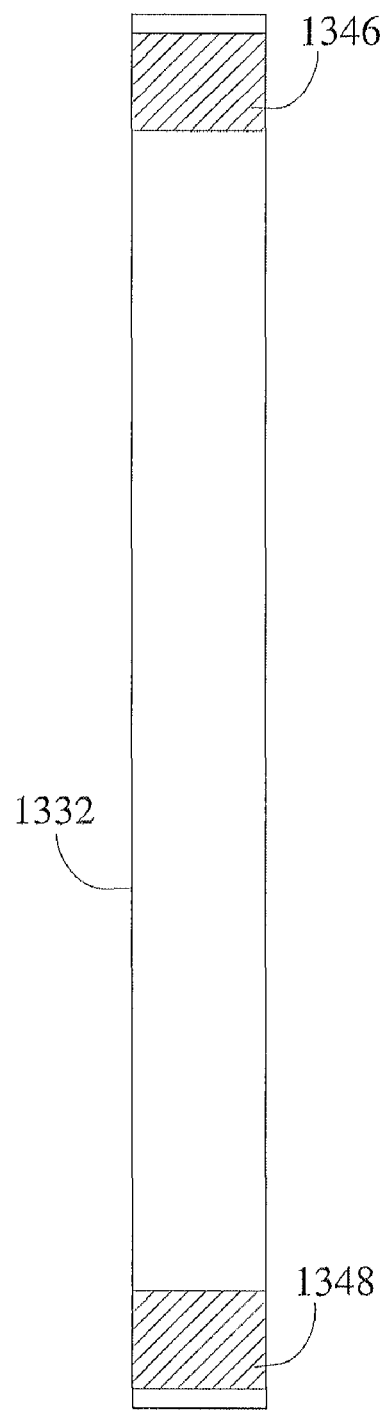
FIG. 16 shows the underside of a wristband according to at least one embodiment of the present disclosure.

FIG. 16 shows the underside of wristband 1332 after separation from label sheet 1312, according to at least one embodiment of the present disclosure. Shown in FIG. 16 are wristband 1332 comprising adhesive deposit 1346 and adhesive deposit 1348. In at least one embodiment of the present disclosure, adhesive deposit 1346 and adhesive deposit 1348 comprise a layer of a repositionable adhesive. In at least one embodiment of the present disclosure, adhesive deposit 1346 and adhesive deposit 1348 comprise a layer of a removable adhesive. In at least one embodiment of the present disclosure, adhesive deposit 1346 and adhesive deposit 1348 comprise a layer of a pressure sensitive adhesive. When wristband 1332 according to an embodiment of the present invention is looped around the wrist of a subject, and the ends of wristband 1332 are adhered together using one or more of adhesive deposits 1346, 1348.

Figure 17A:
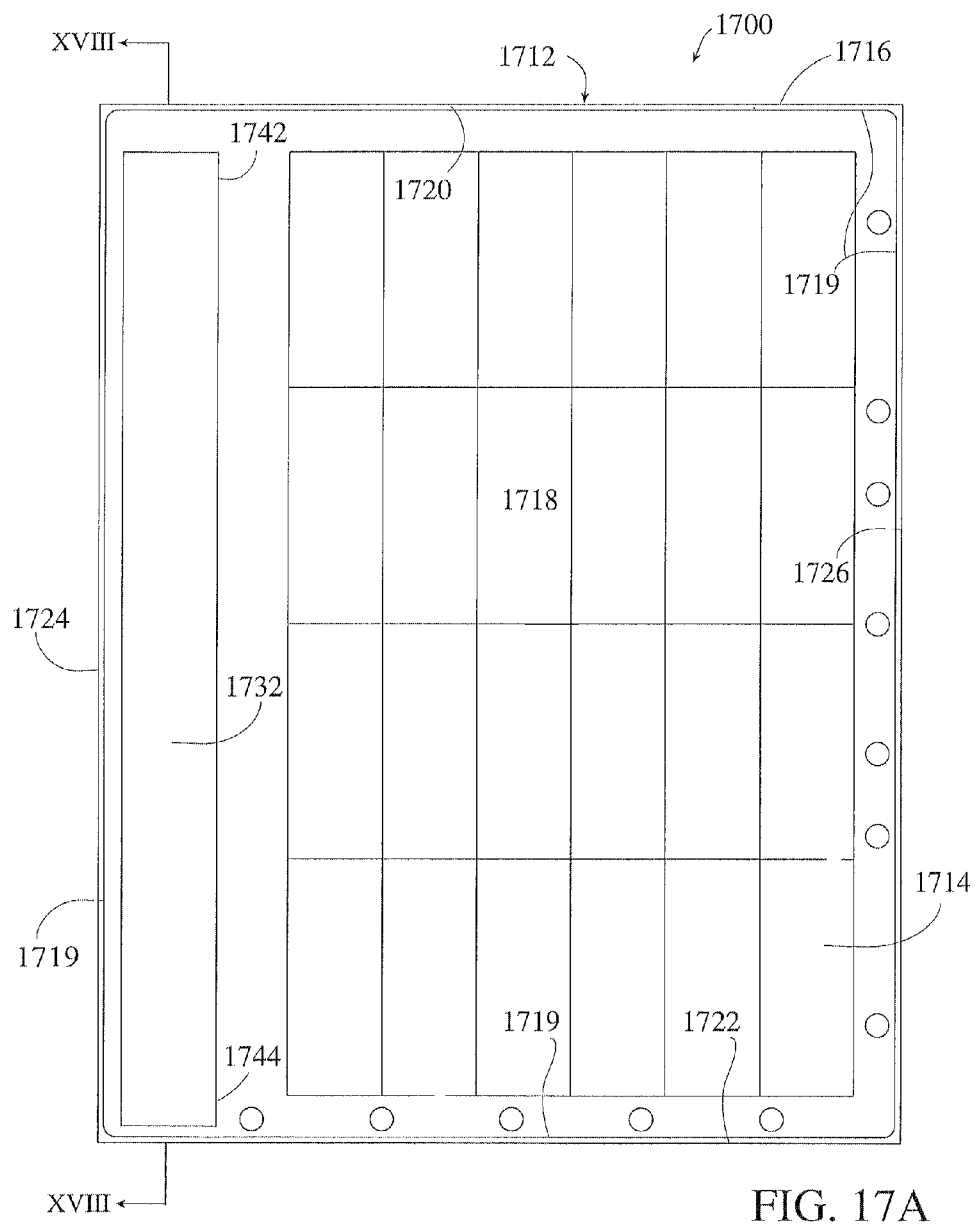
FIG. 17A shows a top view of a wristband label sheet according to at least one embodiment of the present disclosure.

FIG. 17A shows a top view of wristband label sheet 1700 according to at least one embodiment of the present disclosure. Shown in FIG. 17A are label sheet 1712, comprising label material 1714 and liner material 1716. Adhesive 1715 is interposed between label material 1714 and liner material 1716 and removably adheres label material 1714 to liner material 1716. In at least one embodiment of the present disclosure, liner material 1716 comprises a silicone coating on the surface facing adhesive 1715. In the embodiment of wristband label sheet 1700 shown in FIG. 17A, liner material 1716 is bounded by leading edge 1720, trailing edge 1722, side edge 1724, and side edge 1726. Label sheet 1712 may be of any size. In at least one embodiment of label sheet 1712 according to the present disclosure, the outer dimensions of label sheet 1712 are selected to enable label sheet 1712 to fit in a commercially available printing device. For example, in such an embodiment, the outer dimensions of label sheet 1712 may be 8½"×11", 8½"×14", or 210 mm×297 mm.

In at least one embodiment of the present disclosure, label material 1714 comprises perimeter 1719 defining a boundary of label material 1714. In at least one embodiment of the present disclosure, at least a portion of perimeter 1719 is inboard of the boundary formed by leading edge 1720, trailing edge 1722, side edge 1724, and side edge 1726. In at least one embodiment of the present disclosure, perimeter 1719 is coextensive with the boundary formed by leading edge 1720, trailing edge 1722, side edge 1724, and side edge 1726.

In at least one embodiment of the present disclosure, label material 1714 comprises a material suitable for the printing of indicia thereon, such as, for example, paper, polyester, or another polymer material. Indicia may be marked or printed on the top side of label material 1714. For example, the top side of label material 1714 may be exposed to an ink jet printer, a laser print, or another type of printing device capable of applying indicia to the top side of label material 1714. The inks, toners, and/or other printing materials used in the application of indicia to the top side of label material 1714 are selected to be compatible with the printing device used to apply such indicia, the material used for label material 1714, and the intended use of wristband label sheet 1700.

In the embodiment of wristband label sheet 1700 shown in FIG. 17A, label material 1714 comprises a plurality of labels 1718. In at least one embodiment, labels 1718 are die cut in label material 1714. In at least one embodiment of the present disclosure, label material 1714 comprises twenty-four labels 1718, each having dimensions of about 1"×2.5". Other sizes and quantities of labels 1718 are possible.

In at least one embodiment of the present disclosure, wristband 1732 is constructed of a polyester material, although other materials suitable for the intended use of wristband 1732 may be used. In at least one embodiment of the present disclosure, wristband 1732 has dimensions of about 1"×10.75", however wristband 1732 may be of any size that fits on label sheet 1712.

Figure 17B:
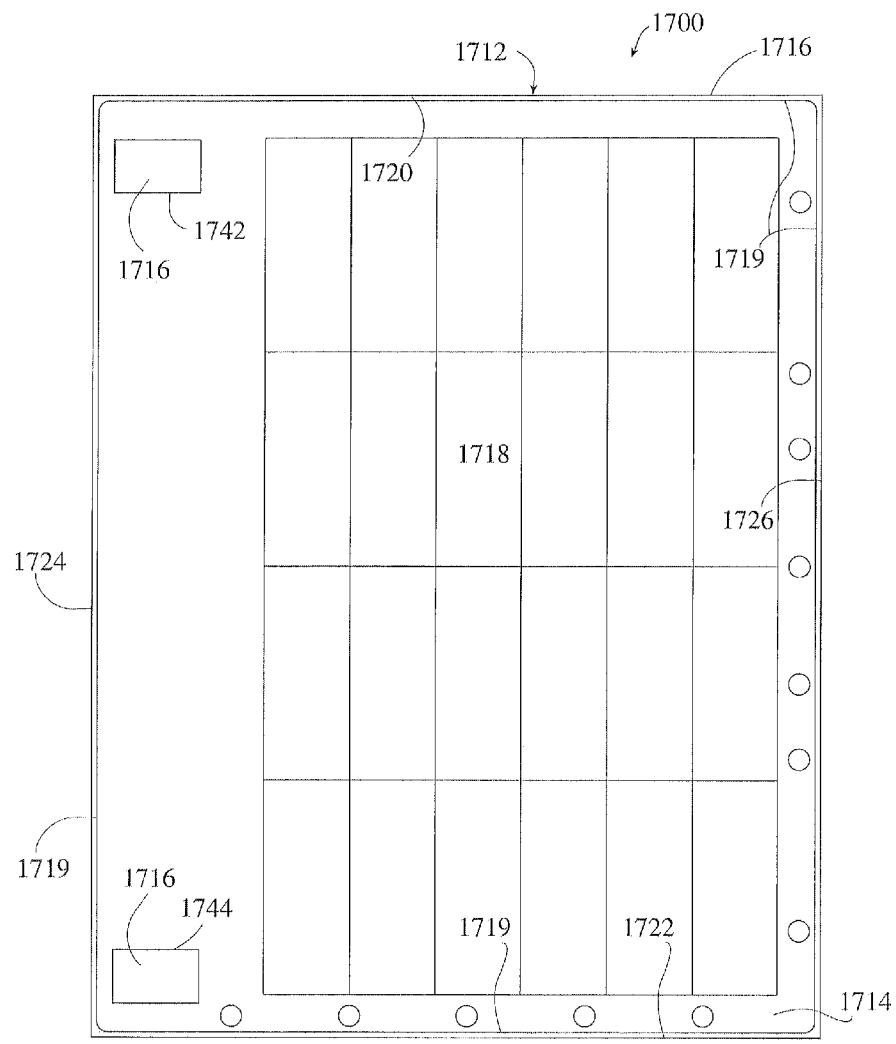
FIG. 17B shows a top view of a label sheet according to at least one embodiment of the present disclosure.

FIG. 17B shows a top view of wristband label sheet 1700 according to at least one embodiment of the present disclosure without the application of wristband 1732. Shown in FIG. 17B are voids 1742 and 1744. In at least one embodiment, voids 1742 and 1744 comprises portions of label material 1714 and adhesive 1715 that have been removed. As shown in FIG. 17B, removal of such portions of label material 1714 exposes liner 1716.

Referring back to FIG. 17A, shown therein are the locations of label material and adhesive voids 1742 and 1744 that are obscured by wristband 1732.

Indicia may be marked or printed on the top side of wristband 1732. For example, the top side of wristband 1732 may be exposed to an ink jet printer, a laser print, or another type of printing device capable of applying indicia to the top side of wristband 1732. Indicia may be printed on wristband 1732 before, after, or concurrently with the printing of indicia on label material 1714. The inks, toners, and/or other printing materials used in the application of indicia to the top side of wristband 1732 are selected to be compatible with the printing device used to apply such indicia, the material used for wristband 1732, and the intended use of wristband 1732.

Figure 18:
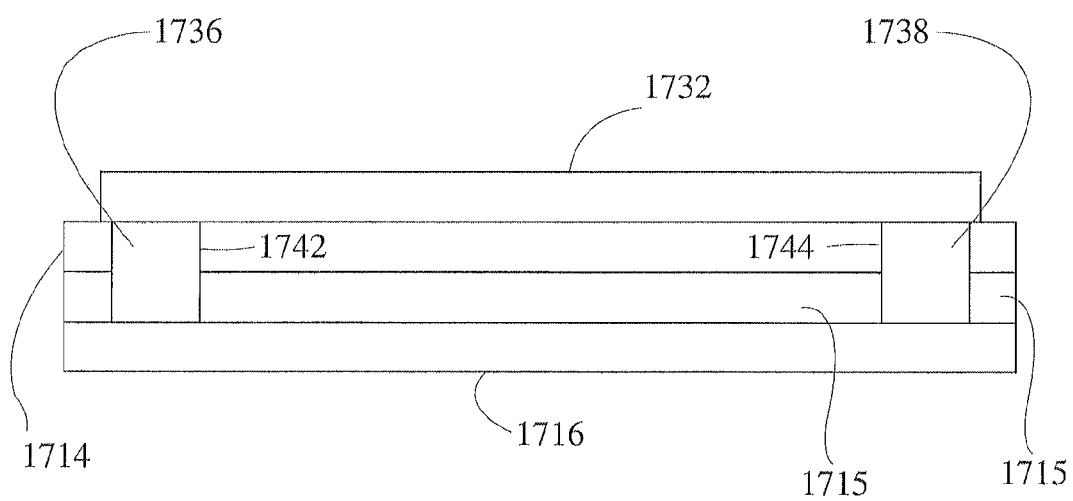
FIG. 18 shows a cross-sectional view of an embodiment of a wristband label sheet according to at least one embodiment of the present disclosure.

FIG. 18 shows a cross-sectional view of the embodiment of wristband label sheet 1700 of FIG. 17A taken on line XVIII-XVIII of FIG. 17A, with the proportions enhanced for purposes of clarity. Shown in FIG. 18 are label material 1714, adhesive layer 1715, liner material 1716, wristband 1732, adhesive stripe 1736, adhesive stripe 1738, void 1742, and void 1744.

Figure 19:
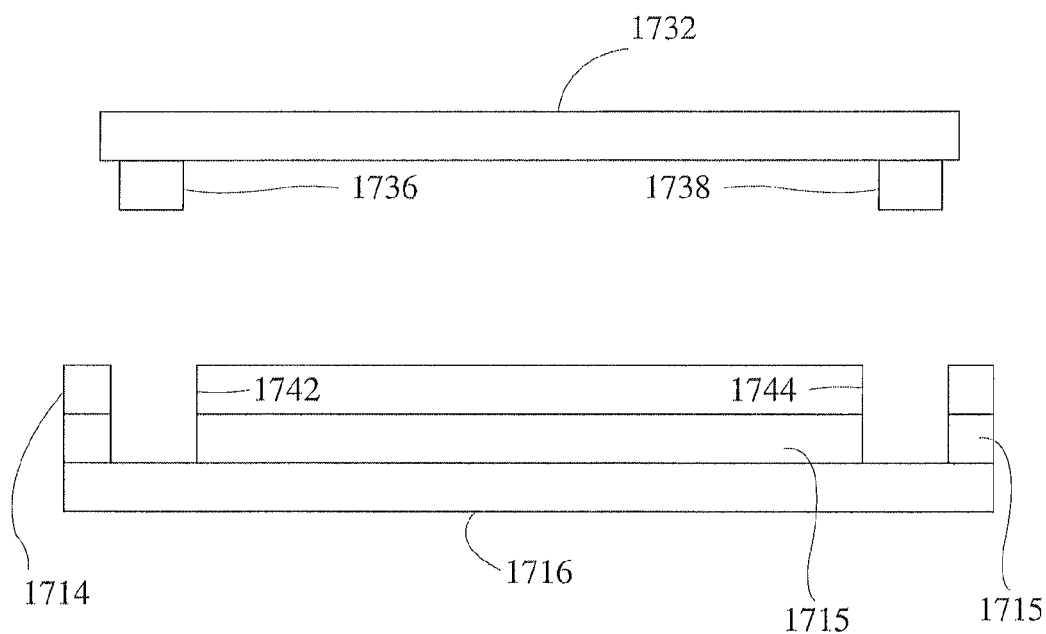
FIG. 19 shows a cross-sectional of an embodiment of a wristband label sheet according to at least one embodiment of the present disclosure.

According to at least one embodiment of the present disclosure, wristband 1732 is removable from label sheet 1712 by grasping wristband 1732 between adhesive stripe 1736 and adhesive stripe 1738 and pulling wristband 1732 away from label sheet 1712. FIG. 19 shows a cross-sectional view of an embodiment of wristband label sheet 1700 according to at least one embodiment of the present disclosure, with the proportions enhanced for purposes of clarity. As shown in FIG. 19, wristband 1732 is separated from label sheet 1712. As shown in FIG. 19, adhesive stripe 1736 and adhesive stripe 1738 remain adhered to the underside of wristband 1732 after wristband 1732 is separated from label sheet 1712.

Figure 20:
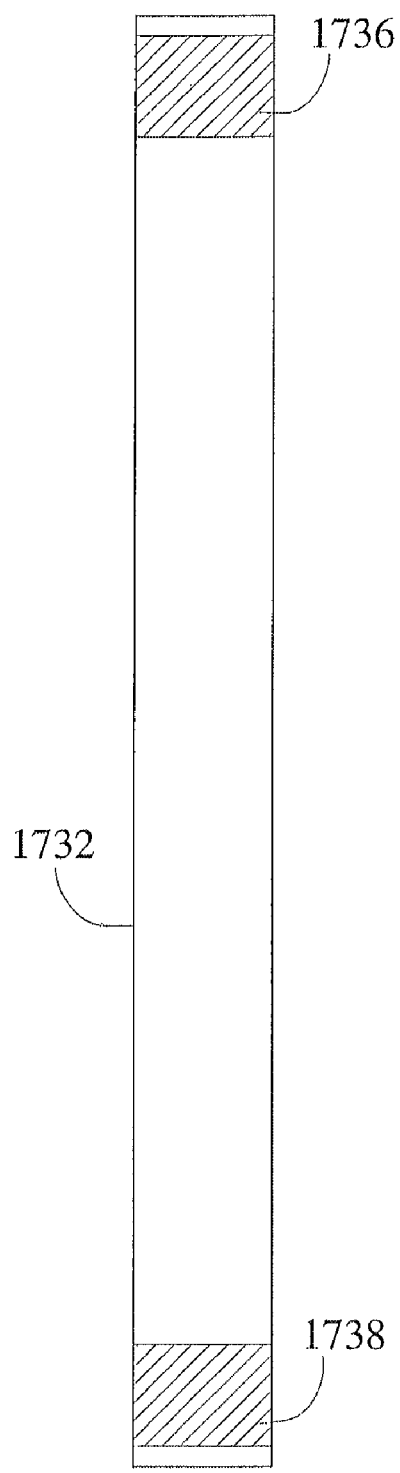
FIG. 20 shows the underside of a wristband according to at least one embodiment of the present disclosure.

FIG. 20 shows the underside of wristband 1732 after separation from label sheet 1712, according to at least one embodiment of the present disclosure. Shown in FIG. 20 are wristband 1732 comprising adhesive stripe 1736 and adhesive stripe 1738. In at least one embodiment of the present disclosure, adhesive stripe 1736 and adhesive stripe 1738 comprises a layer of a repositionable adhesive. In at least one embodiment of the present disclosure, adhesive stripe 1736 and adhesive stripe 1738 comprises a layer of a removable adhesive. In at least one embodiment of the present disclosure, adhesive stripe 1736 and adhesive stripe 1738 comprises a layer of a pressure sensitive adhesive. When wristband 1732 according to an embodiment of the present invention is looped around the wrist of a subject, and the ends of wristband 1732 are adhered together using one or more of adhesive stripe 1736 and adhesive stripe 1738 on wristband 1732.

Figure 21A:
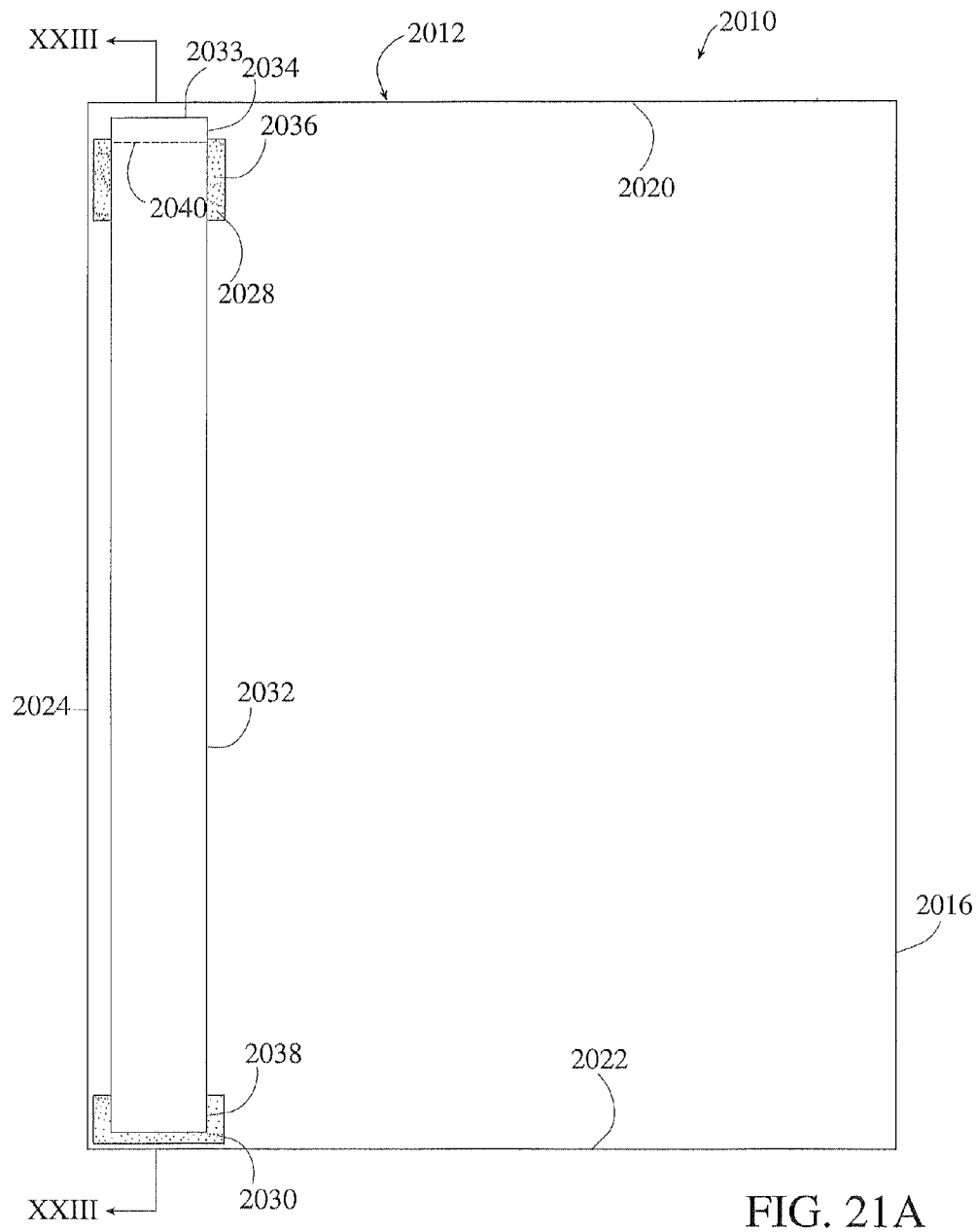
FIG. 21A shows a top view of a wristband sheet according to at least one embodiment of the present disclosure.

FIG. 21A shows a top view of wristband sheet 2010 according to at least one embodiment of the present disclosure. Shown in FIG. 21A is sheet material 2012. In the embodiment of wristband sheet 2010 shown in FIG. 21A, sheet material 2012 is bounded by leading edge 2020, trailing edge 2022, side edge 2024, and side edge 2016. Sheet material 2012 may be of any size. In at least one embodiment of sheet material 2012 according to the present disclosure, the outer dimensions of sheet material 2012 are selected to enable sheet material 2012 to fit in a commercially available printing device. For example, in such an embodiment, the outer dimensions of sheet material 2012 may be 3"×11", 8½"×11", 8½"×14", or 210 mm×297 mm.

In at least one embodiment of the present disclosure, sheet material 2012 comprises a material suitable for the printing of indicia thereon, such as, for example, paper, polyester, or another polymer material. Indicia may be marked or printed on the top side of sheet material 2012. For example, the top side of sheet material 2012 may be exposed to an ink jet printer, a laser print, or another type of printing device capable of applying indicia to the top side of sheet material 2012. The inks, toners, and/or other printing materials used in the application of indicia to the top side of sheet material 2012 are selected to be compatible with the printing device used to apply such indicia, the material used for sheet material 2012, and the intended use of wristband sheet 2010.

In the embodiment of wristband sheet 2010 shown in FIG. 21A, sheet material 2012 comprises release patch 2028 and release patch 2030. Release patches 2028, 2030 comprise areas of a release coating (such as, for example, a silicone) applied to the surface of sheet material 2012, to allow the removable adherence of wristband 2032 to sheet material 2012, as discussed herein. In at least one embodiment of the present disclosure, release patches 2028, 2030 comprise free radical ultraviolet cured silicone. In at least one embodiment of the present disclosure, release patches 2028, 2030 comprise a cationic ultraviolet cured release coating. Alternatively, any type of coating (including no-silicone coatings) that permits the removable adherence of wristband 2032 to sheet material 2012 may be used.

Also shown in the embodiment of wristband sheet 2010 shown in FIG. 21A is wristband 2032 comprising stub 2033 and line of weakness 2040. In at least one embodiment of the present disclosure, line of weakness 2040 comprises a series of perforations. In at least one embodiment of the present disclosure, wristband 2032 (including stub 2033) is constructed of a polyester material, although other materials suitable for the intended use of wristband 2032 may be used. In at least one embodiment of the present disclosure, wristband 2032 has dimensions of about 1"×10.75", however wristband 2032 may be of any size that fits on sheet material 2012.

Figure 21B:
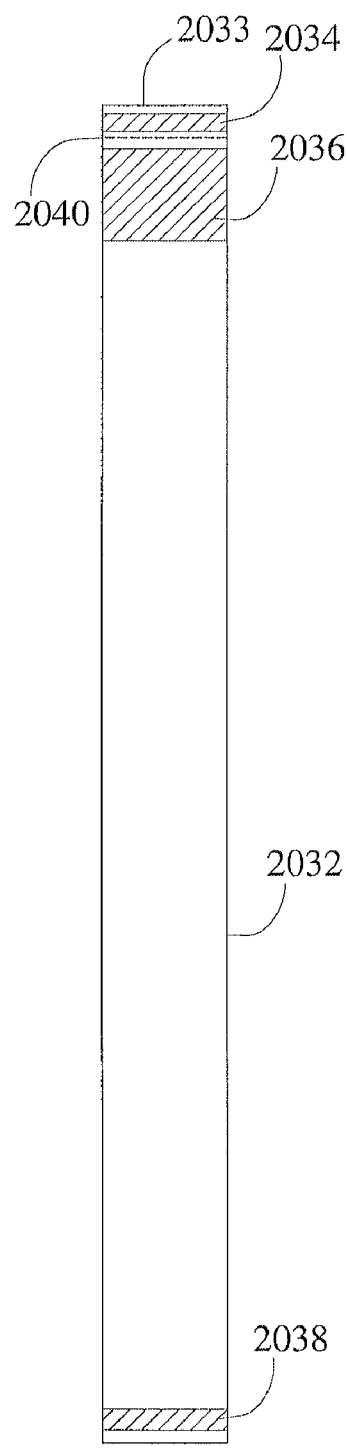
FIG. 21B shows the underside of a wristband according to at least one embodiment of the present disclosure.

FIG. 21B shows the underside of wristband 2032 before attachment to sheet material 2012, according to at least one embodiment of the present disclosure. Shown in FIG. 21B are wristband 2032 comprising stub 2033, adhesive stripe 2034, adhesive stripe 2036, adhesive stripe 2038, and line of weakness 2040. In at least one embodiment of the present disclosure, adhesive stripes 2034, 2036, 2038 comprise a layer of a hot melt adhesive.

Referring back to FIG. 21A, shown therein are the locations of adhesive stripes 2034, 2036, 2038 on the underside of wristband 2032. Adhesive stripe 2034 is interposed between sheet material 2012 and stub 2033, and adheres sheet material 2012 to stub 2033. In at least one embodiment of the present disclosure, adhesive stripe 2034 is oriented toward leading edge 20 of sheet material 2012. Adhesive stripe 2036 is interposed between wristband 2032 and release patch 2028 and removably adheres wristband 2032 to release patch 2028. Adhesive stripe 2038 is interposed between wristband 2032 and release patch 2030 and removably adheres wristband 2032 to release patch 2030. As discussed herein, adhesive stripes 2036, 2038 are operable to secure wristband 2032 around a subject's wrist after wristband 2032 is removed from sheet material 2012.

In at least one alternative embodiment of the present disclosure, release patch 2028 and adhesive stripe 2036 may be omitted from wristband sheet 2010. In such an embodiment adhesive stripe 2034 remains and is interposed between sheet material 2012 and stub 2033 to adhere sheet material 2012 to stub 2033. In such an embodiment adhesive stripe 2038 remains and is interposed between wristband 2032 and release patch 2030 to removably adhere wristband 2032 to release patch 2030.

In at least one alternative embodiment of the present disclosure, adhesive stripes 2036, 2038 comprise a repositionable adhesive. In such an embodiment release patches 2028, 2030 may be omitted from wristband sheet 2010. In at least one other alternative embodiment of the present disclosure, a wristband sheet comprises a stub at each end of the wristband.

Indicia may be marked or printed on the top side of wristband 2032. For example, the top side of wristband 2032 may be exposed to an ink jet printer, a laser print, or another type of printing device capable of applying indicia to the top side of wristband 2032. Indicia may be printed on wristband 2032 before, after, or concurrently with the printing of indicia on sheet material 2012. The inks, toners, and/or other printing materials used in the application of indicia to the top side of wristband 2032 are selected to be compatible with the printing device used to apply such indicia, the material used for wristband 2032, and the intended use of wristband 2032.

Figure 22A:
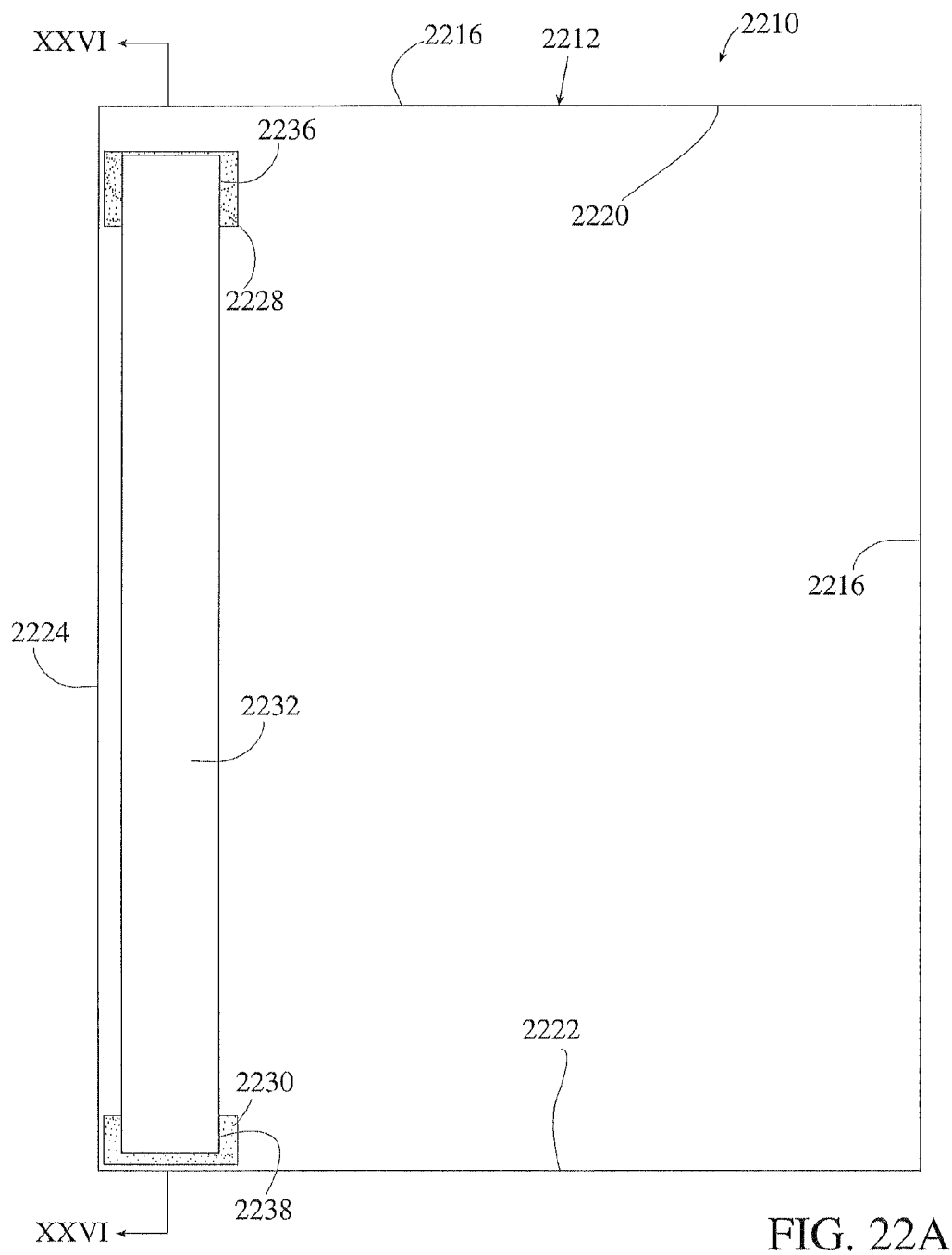
FIG. 22A shows a top view of a wristband sheet according to at least one embodiment of the present disclosure.

FIG. 22A shows a top view of wristband sheet 2210 according to at least one embodiment of the present disclosure. Shown in FIG. 22A is sheet material 2212. In the embodiment of wristband sheet 2210 shown in FIG. 22A, sheet material 2212 is bounded by leading edge 2220, trailing edge 2222, side edge 2224, and side edge 2226. Sheet material 2212 may be of any size. In at least one embodiment of sheet material 2212 according to the present disclosure, the outer dimensions of sheet material 2212 are selected to enable sheet material 2212 to fit in a commercially available printing device. For example, in such an embodiment, the outer dimensions of sheet material 2212 may be 3"×11", 8½"×11", 8½"×14", or 210 mm×297 mm.

In at least one embodiment of the present disclosure, sheet material 2212 comprises a material suitable for the printing of indicia thereon, such as, for example, paper, polyester, or another polymer material. Indicia may be marked or printed on the top side of sheet material 2212. For example, the top side of sheet material 2212 may be exposed to an ink jet printer, a laser print, or another type of printing device capable of applying indicia to the top side of sheet material 2212. The inks, toners, and/or other printing materials used in the application of indicia to the top side of sheet material 2212 are selected to be compatible with the printing device used to apply such indicia, the material used for sheet material 2212, and the intended use of wristband sheet 2210.

In the embodiment of wristband sheet 2210 shown in FIG. 22A, sheet material 2212 comprises release patch 2228 and release patch 2230. Release patches 2228, 2230 comprise areas of a release coating (such as, for example, a silicone) applied to the surface of sheet material 2212, to allow the removable adherence of wristband 2232 to sheet material 2212, as discussed herein. In at least one embodiment of the present disclosure, release patches 2228, 2230 comprise free radical ultraviolet cured silicone. In at least one embodiment of the present disclosure, release patches 2228, 2230 comprise a cationic ultraviolet cured release coating. Alternatively, any type of coating (including no-silicone coatings) that permits the removable adherence of wristband 2232 to sheet material 2212 may be used.

Also shown in the embodiment of wristband sheet 2210 shown in FIG. 22A is wristband 2232. In at least one embodiment of the present disclosure, wristband 2232 is constructed of a polyester material, although other materials suitable for the intended use of wristband 2232 may be used. In at least one embodiment of the present disclosure, wristband 2232 has dimensions of about 1"×10.75", however wristband 2232 may be of any size that fits on sheet material 2212.

Figure 22B:
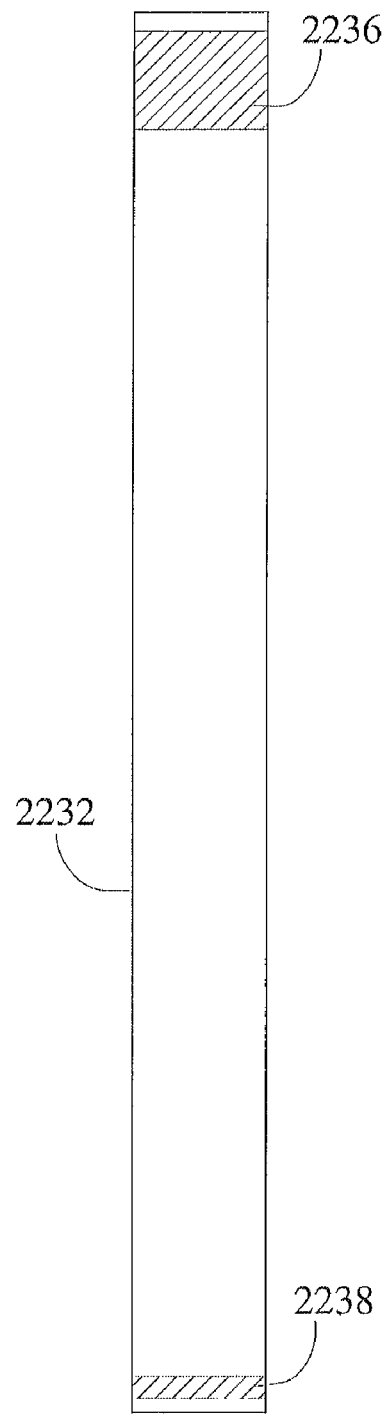
FIG. 22B shows the underside of a wristband according to at least one embodiment of the present disclosure.

FIG. 22B shows the underside of wristband 2232 before attachment to sheet material 2212, according to at least one embodiment of the present disclosure. Shown in FIG. 22B are wristband 2232 comprising adhesive stripe 2236 and adhesive stripe 2238. In at least one embodiment of the present disclosure, adhesive stripes 2236, 2238 comprise a layer of a hot melt adhesive.

Referring back to FIG. 22A, shown therein are the locations of adhesive stripes 2236, 2238 on the underside of wristband 2232. Adhesive stripe 2236 is interposed between wristband 2232 and release patch 2228 and removably adheres wristband 2232 to release patch 2228. Adhesive stripe 2238 is interposed between wristband 2232 and release patch 2230 and removably adheres wristband 2232 to release patch 2230. As discussed herein, adhesive stripes 2236, 2238 are operable to secure wristband 2232 around a subject's wrist after wristband 2232 is removed from sheet material 2212.

In at least one alternative embodiment of the present disclosure, adhesive stripes 2236, 2238 comprise a repositionable adhesive. In such an embodiment release patches 2228, 2230 may be omitted from wristband sheet 2210.

Indicia may be marked or printed on the top side of wristband 2232. For example, the top side of wristband 2232 may be exposed to an ink jet printer, a laser print, or another type of printing device capable of applying indicia to the top side of wristband 2232. Indicia may be printed on wristband 2232 before, after, or concurrently with the printing of indicia on sheet material 2212. The inks, toners, and/or other printing materials used in the application of indicia to the top side of wristband 2232 are selected to be compatible with the printing device used to apply such indicia, the material used for wristband 2232, and the intended use of wristband 2232.

Figure 23:
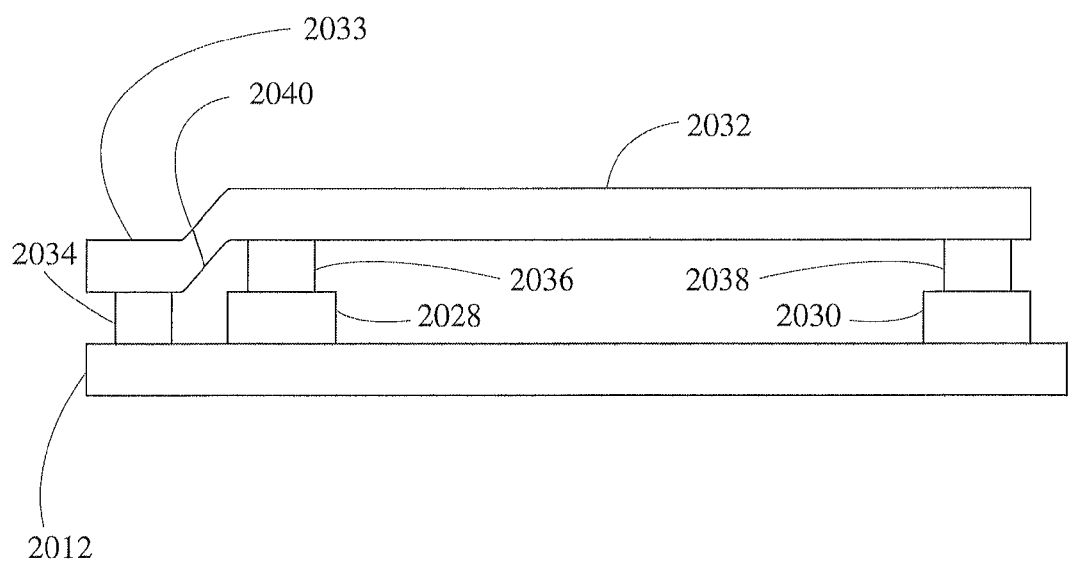
FIG. 23 shows a cross-sectional view of an embodiment of a wristband sheet according to at least one embodiment of the present disclosure.

FIG. 23 shows a cross-sectional view of the embodiment of wristband sheet 2010 of FIG. 21A taken on line XXIII-XXIII of FIG. 21A, with the proportions enhanced for purposes of clarity. Shown in FIG. 23 are sheet material 2012, release patch 2028, release patch 2030, wristband 2032, stub 2033, adhesive stripe 2034, adhesive stripe 2036, adhesive stripe 2038, and line of weakness 2040.

Figure 24:
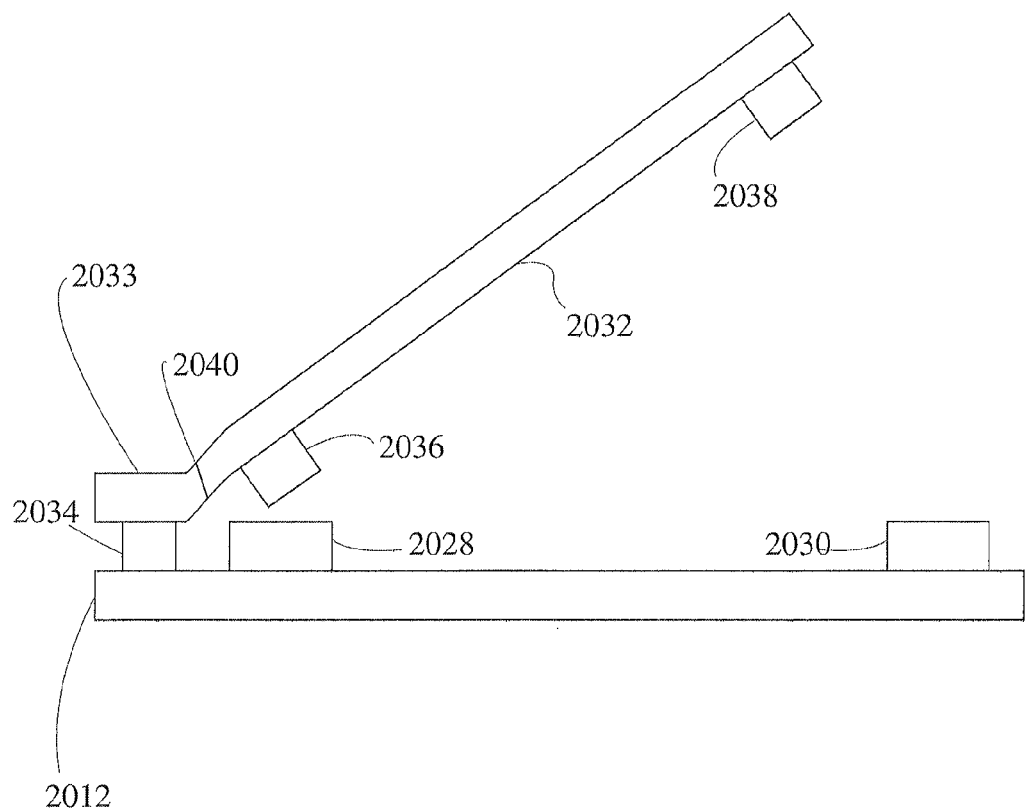
FIG. 24 shows a cross-sectional view of an embodiment of a wristband sheet according to at least one embodiment of the present disclosure.

According to at least one embodiment of the present disclosure, wristband 2032 is removable from sheet material 2012 by grasping wristband 2032 between adhesive stripe 2036 and adhesive stripe 2038 and pulling wristband 2032 away from sheet material 2012. FIG. 24 shows a cross-sectional view of an embodiment of wristband sheet 2010 according to at least one embodiment of the present disclosure, with the proportions enhanced for purposes of clarity. As shown in FIG. 24, wristband 2032 is partially separated from sheet material 2012. As shown in FIG. 24, adhesive stripe 2036 and adhesive stripe 2038 have separated from release patch 28 and release patch 2030, respectively. Release patch 2028 and release patch 2030 remain on the top surface of sheet material 2012. Adhesive stripe 2036 and adhesive stripe 2038 remain adhered to the underside of wristband 2032. Stub 2033 remains adhered to the top surface of sheet material 2012 by adhesive stripe 2034. Wristband 2032 remains attach to stub 2033 at line of weakness 2040.

Figure 25A:
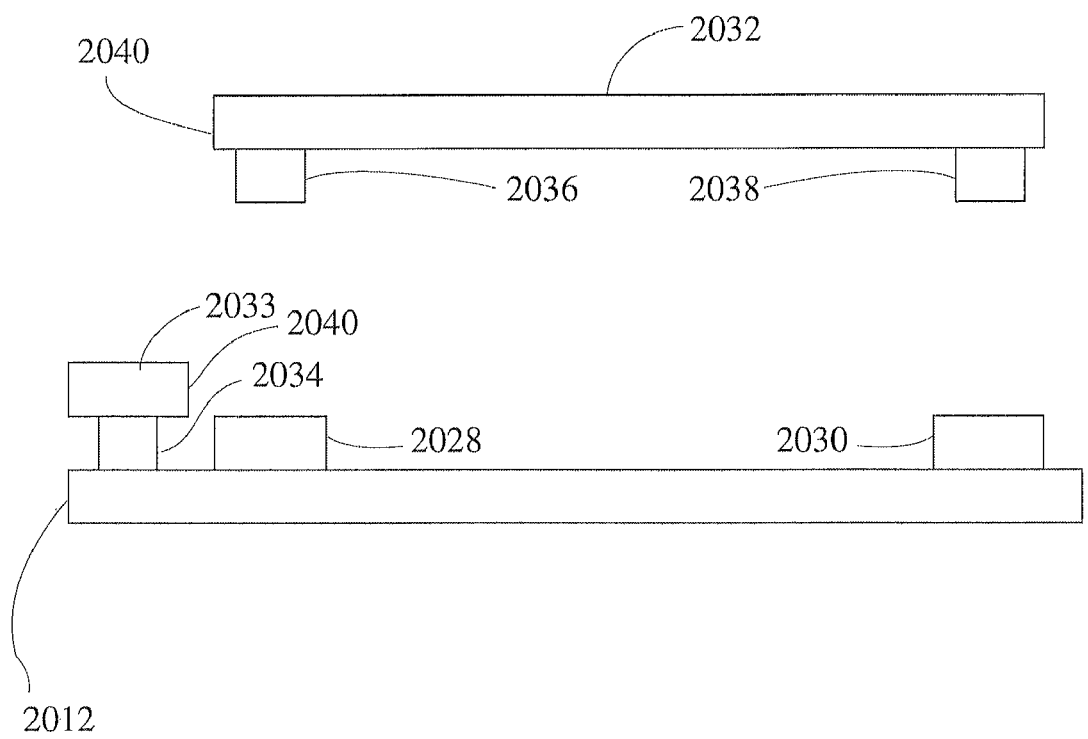
FIG. 25A shows a cross-sectional view of an embodiment of a wristband sheet according to at least one embodiment of the present disclosure.

FIG. 25A shows a cross-sectional view of an embodiment of wristband sheet 2010 according to at least one embodiment of the present disclosure, with the proportions enhanced for purposes of clarity. As shown in FIG. 25A, wristband 2032 is fully separated from sheet material 2012, and wristband 2032 is separated from stub 2033 at line of weakness 2040. Stub 2033 remains adhered to the top surface of sheet material 2012 by adhesive stripe 2034. As shown in FIG. 25A, adhesive stripes 2036, 2038 remain adhered to the underside of wristband 2032, and release patch 2028 and release patch 2030 remain adhered to sheet material 2012.

Figure 25B:
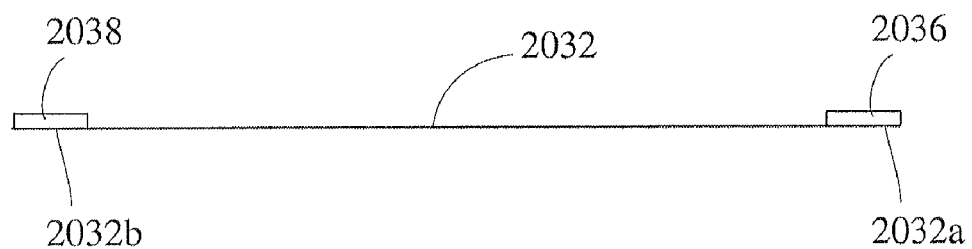
FIGS. 25B-C show side views of a wristband according to at least one embodiment of the present disclosure.
Figure 25C:
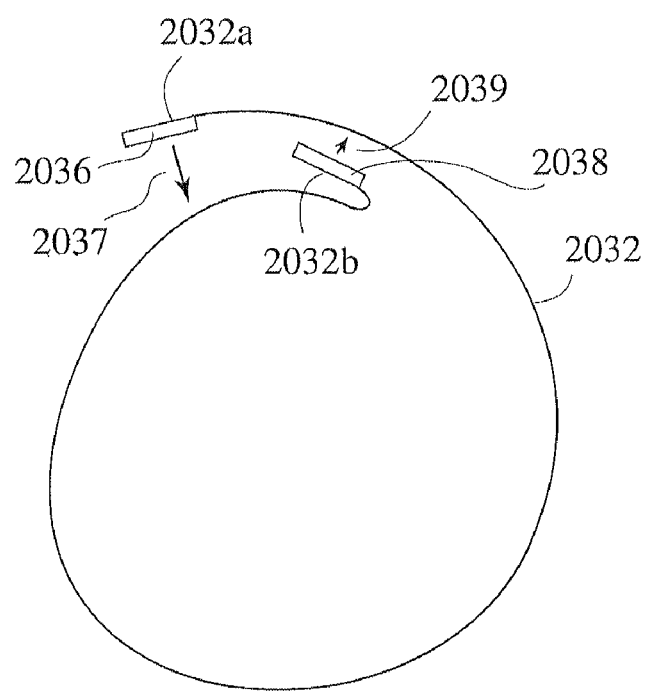

FIGS. 25B-C show side views of wristband 2032 after removal from sheet material 2012, as it is put into use. FIG. 25B shows a side view of wristband 2032 after removal from sheet material 2012, according to at least one embodiment of the present disclosure. Shown in FIG. 25B are wristband 2032 comprising first end 2032a, second end 2032b, adhesive stripe 2036, and adhesive stripe 2038.

As shown in FIG. 25C, wristband 2032 is formed into a loop. The exposed adhesive surface of adhesive stripe 2038 is brought into contact with and adhered to wristband 2032 (as shown by arrow 2039). After adhesive stripe 2038 is adhered to wristband 2032, the exposed adhesive surface of adhesive stripe 2036 is brought into contact with and adhered to wristband 2032 (as shown by arrow 2037). First end 2032a and second end 2032b thereby are adhered together. In normal use, wristband 2032 is looped around the wrist of a subject in the manner shown in FIG. 9.

Figure 26:
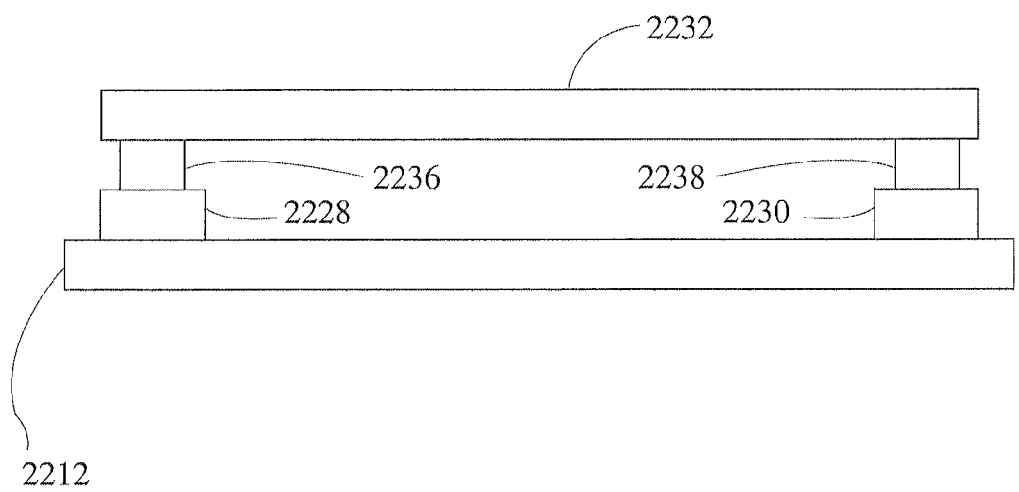
FIG. 26 shows a cross-sectional view of an embodiment of a wristband sheet according to at least one embodiment of the present disclosure.

FIG. 26 shows a cross-sectional view of the embodiment of wristband sheet 2210 of FIG. 22A taken on line XXVI-XXVI of FIG. 22A, with the proportions enhanced for purposes of clarity. Shown in FIG. 26 are sheet material 2212, release patch 2228, release patch 2230, wristband 2232, adhesive stripe 2236, and adhesive stripe 2238.

Figure 27:
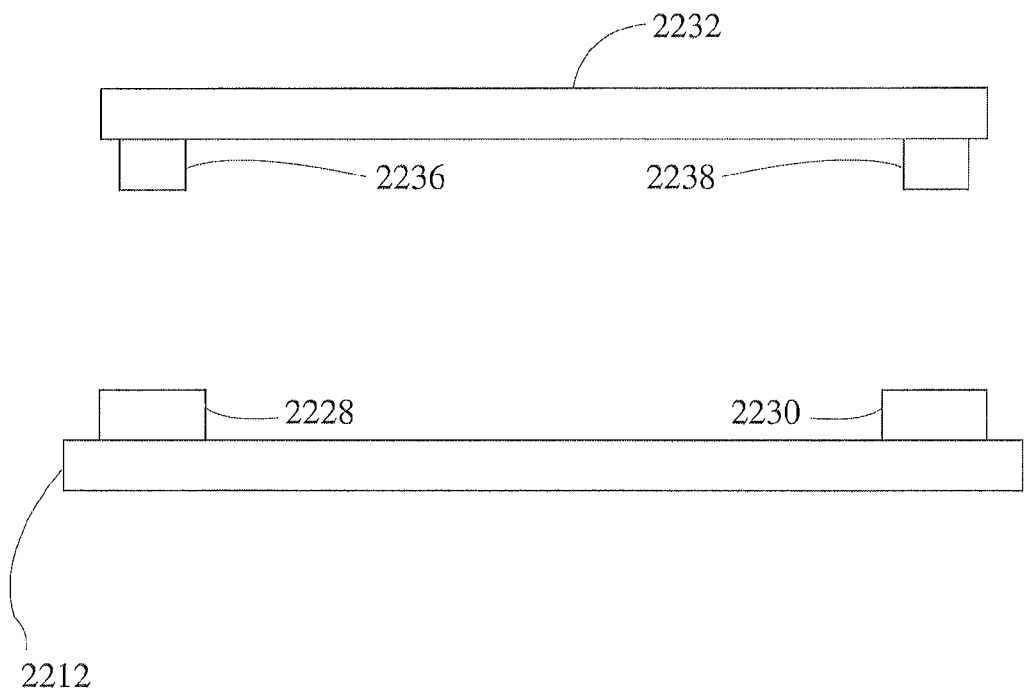
FIG. 27 shows a cross-sectional of an embodiment of a wristband sheet according to at least one embodiment of the present disclosure.

According to at least one embodiment of the present disclosure, wristband 2232 is removable from sheet material 2212 by grasping wristband 2232 between adhesive stripe 2236 and adhesive stripe 2238 and pulling wristband 2232 away from sheet material 2212. FIG. 27 shows a cross-sectional view of an embodiment of wristband sheet 2210 according to at least one embodiment of the present disclosure, with the proportions enhanced for purposes of clarity. As shown in FIG. 27, wristband 2232 is separated from sheet material 2212. As shown in FIG. 27, adhesive stripe 2236 and adhesive stripe 2238 have separated from release patch 2228 and release patch 2230, respectively. Release patch 2228 and release patch 2230 remain on the top surface of sheet material 2212. Adhesive stripe 2236 and adhesive stripe 2238 remain adhered to the underside of wristband 2232.

Figure 28A:
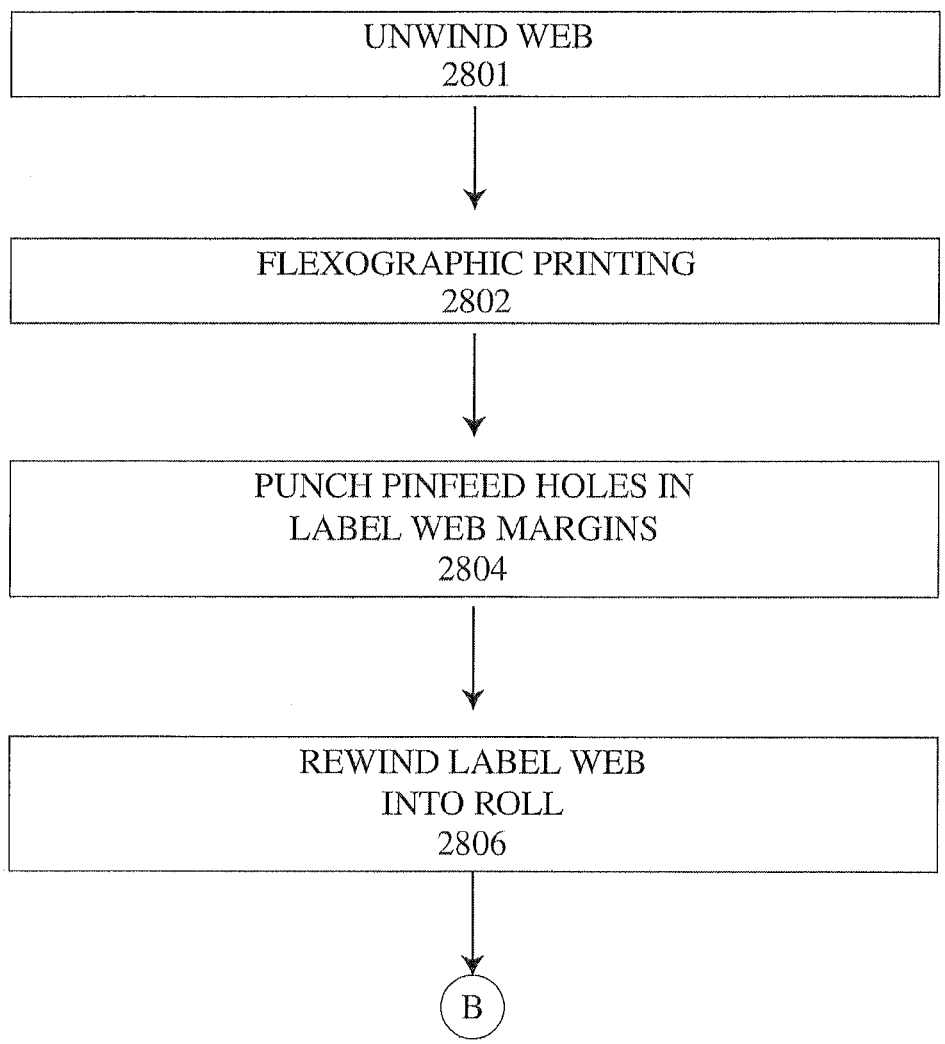
FIGS. 28A-C shows a flowchart for a process for manufacturing a wristband sheet according to at least one embodiment of the present disclosure.
Figure 28B:
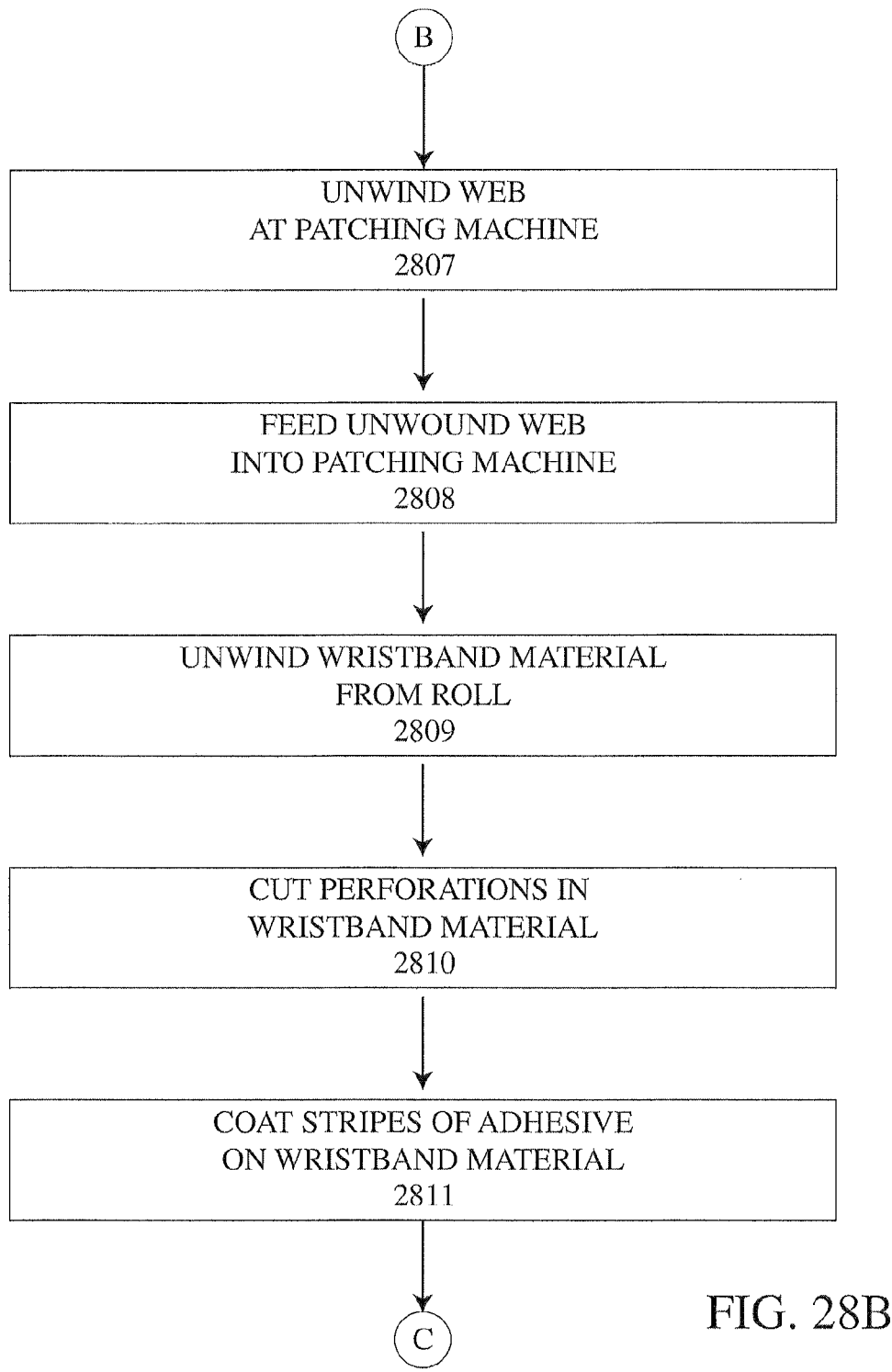
Figure 28C:
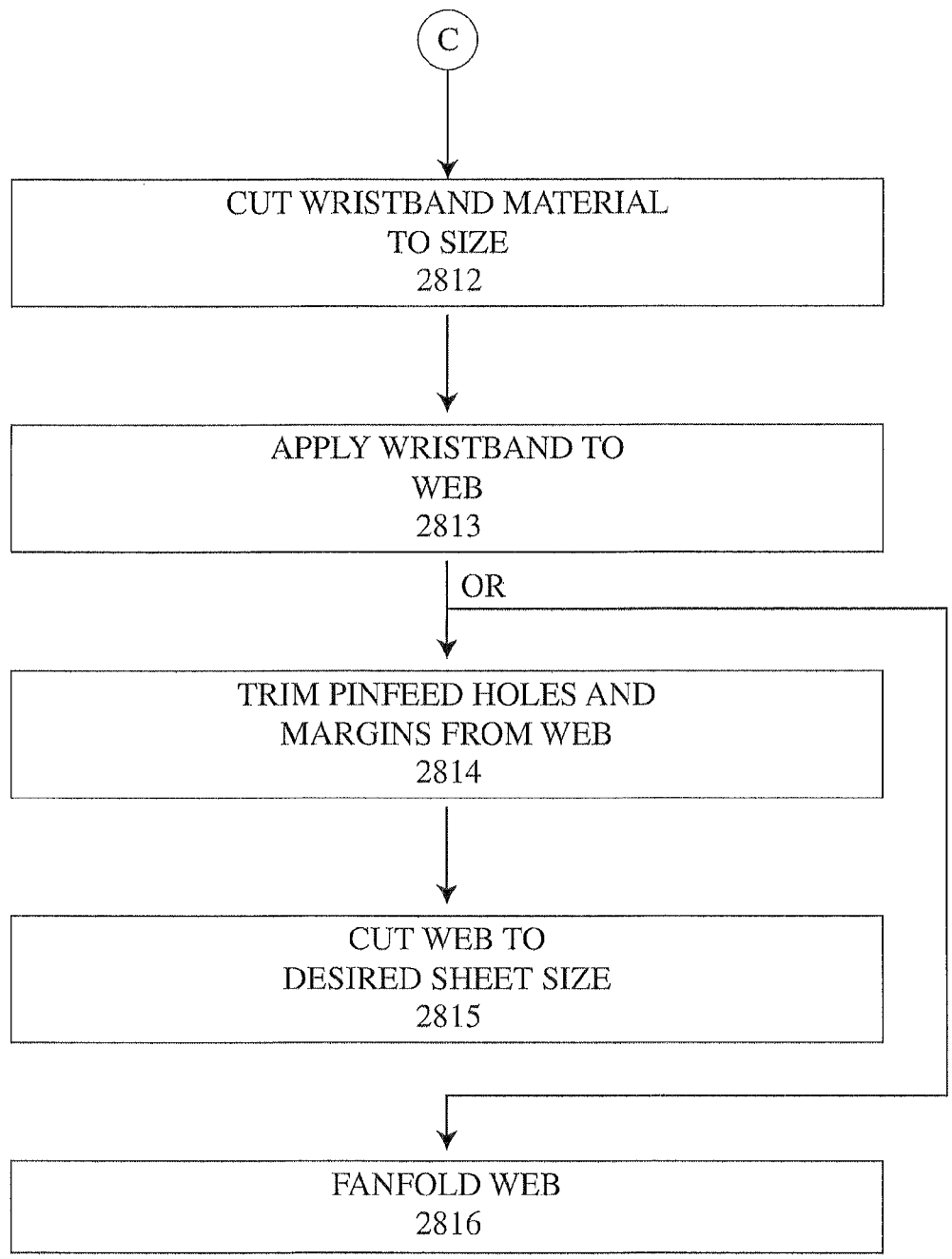

FIGS. 28A-C shows a flowchart illustrating a process for manufacturing a wristband sheet according to at least one embodiment of the present disclosure.

In step 2801 of the embodiment of the present disclosure shown in FIG. 28A, a web of sheet material is unwound from a roll and fed mechanically into one or more flexographic printing presses. According to at least on embodiment of the present disclosure, the web of sheet material comprises an edge margin of at least about ½" on each edge, such that the overall width of web of sheet material is 1" greater than the desired width of the finished product.

In step 2802 of the embodiment of the present disclosure shown in FIG. 28A, one or more flexographic printing presses apply one or more release patches comprising silicone or another type of release coating to the surface of the sheet material. Such flexographic printing presses also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 28A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 2804 of the embodiment of the present disclosure shown in FIG. 28A, the web of sheet material proceeds to a punching station where pinfeed holes are punched in ½" margins at each edge of the web of sheet material, to facilitate registration of the web of sheet material in the process during which wristbands are applied to the web of sheet material (discussed hereinafter).

In step 2806 of the embodiment of the present disclosure shown in FIG. 28A, after printing of release patches, die cutting, and punching of pinfeed holes, the web of sheet material is rewound onto rolls that will be furnished to the patching machine process.

In step 2807 of the embodiment of the present disclosure shown in FIG. 28B, the rolled web of sheet material from step 2807 is unwound and fed into a patching machine, wherein one or more wristbands will be applied to the web of sheet material.

In at least one alternative embodiment of the present disclosure, the steps shown as step 2806 and step 2807 of the embodiment of the present disclosure shown in FIG. 28B may be omitted. In such an embodiment, the web of sheet material proceeds to step 2808 of the embodiment of the present disclosure shown in FIG. 28B.

In step 2808 of the embodiment of the present disclosure shown in FIG. 28B, the punched pinfeed holes in the web of sheet material engage with a pinfeed mechanism of the patching machine. The pinfeed mechanism of the patching machine pulls the web of sheet material into and through the patching machine by pins that penetrate the previously punched pinfeed holes and rotate on gear driven shafts to drive the web of sheet material through the patching machine at a predetermined feed rate.

In step 2809 of the embodiment of the present disclosure shown in FIG. 28B, a roll of wristband material (such as, for example, a roll of a polyester material) is unwound mechanically and fed into the patching machine. According to at least on embodiment of the present disclosure, the width of the wristband material on the roll of wristband material is the same as the desired width of the wristband to be applied to applied to the web of sheet material (discussed hereinafter).

In step 2810 of the embodiment of the present disclosure shown in FIG. 28B, if required for the wristband sheet design, lines of weakness are cut into the unrolled wristband material at a perforating station.

In step 2811 of the embodiment of the present disclosure shown in FIG. 28B, the patching machine coats one or more stripes of adhesive on the underside the web of wristband material polyester at an adhesive coating station.

In step 2812 of the embodiment of the present disclosure shown in FIG. 28C, the patching machine cuts each wristband to a predetermined length. For example, if the finished product required a 1" long wristband, the patching machine cuts off a 1" length of wristband material from the roll of wristband material. In an exemplary embodiment where a 1" long, 10.75" wide wristband is to be applied to an 8.5" long sheet, the 10.75" wide web of wristband material is fed by computer controlled nip type feed rollers at a rate of 1" for every 8.5" of sheet material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder.

In step 2813 of the embodiment of the present disclosure shown in FIG. 28C, after the wristband is cut to length, the vacuum cylinder carries each cut-off wristband to an impression roller that is wrapped by the web of sheet material. At the impression roller the wristband is transferred from the vacuum cylinder to the face of the web of sheet material. The wristband is applied such that one or more of the adhesive stripes on the underside of the wristband are aligned with one or more of the release patches on the sheet material. The wristband is adhered to the web of sheet material by the adhesive stripes that were applied to the underside of the wristband. The patching machine comprises gearing that keeps the cutting cylinder and vacuum cylinder in time with the pace at which the patching machine's pinfeed mechanism moves the web of sheet material.

In step 2814 of the embodiment of the present disclosure shown in FIG. 28C, if required for the wristband sheet design, the ½" margins (including the pinfeed holes) are mechanically trimmed off of the web of sheet material at a trimming station.

In step 2815 of the embodiment of the present disclosure shown in FIG. 28C, if required for the wristband sheet design, the web of sheet material including the applied wristband is mechanically cut into sheets at a sheeter station, with each sheet containing one or more wristbands as required by the wristband sheet design. The sheets are fed into a hatcher/stacker, and then may be shrink-wrapped and packaged. Sheeting is an alternative to the fanfolding step discussed herein.

In step 2816 of the embodiment of the present disclosure shown in FIG. 28C, if required for the wristband sheet design, the web of sheet material including the applied wristband may be fanfolded in-line with a mechanical folder or by gravity in waterfall fashion, with each fanfold containing one or more wristbands as required by the wristband sheet design. The wristband sheet design may require the ½" margins with pinfeed holes to be left on the fanfolded web of sheet material. Fanfolding is an alternative to the sheeting step discussed above.

Figure 29:
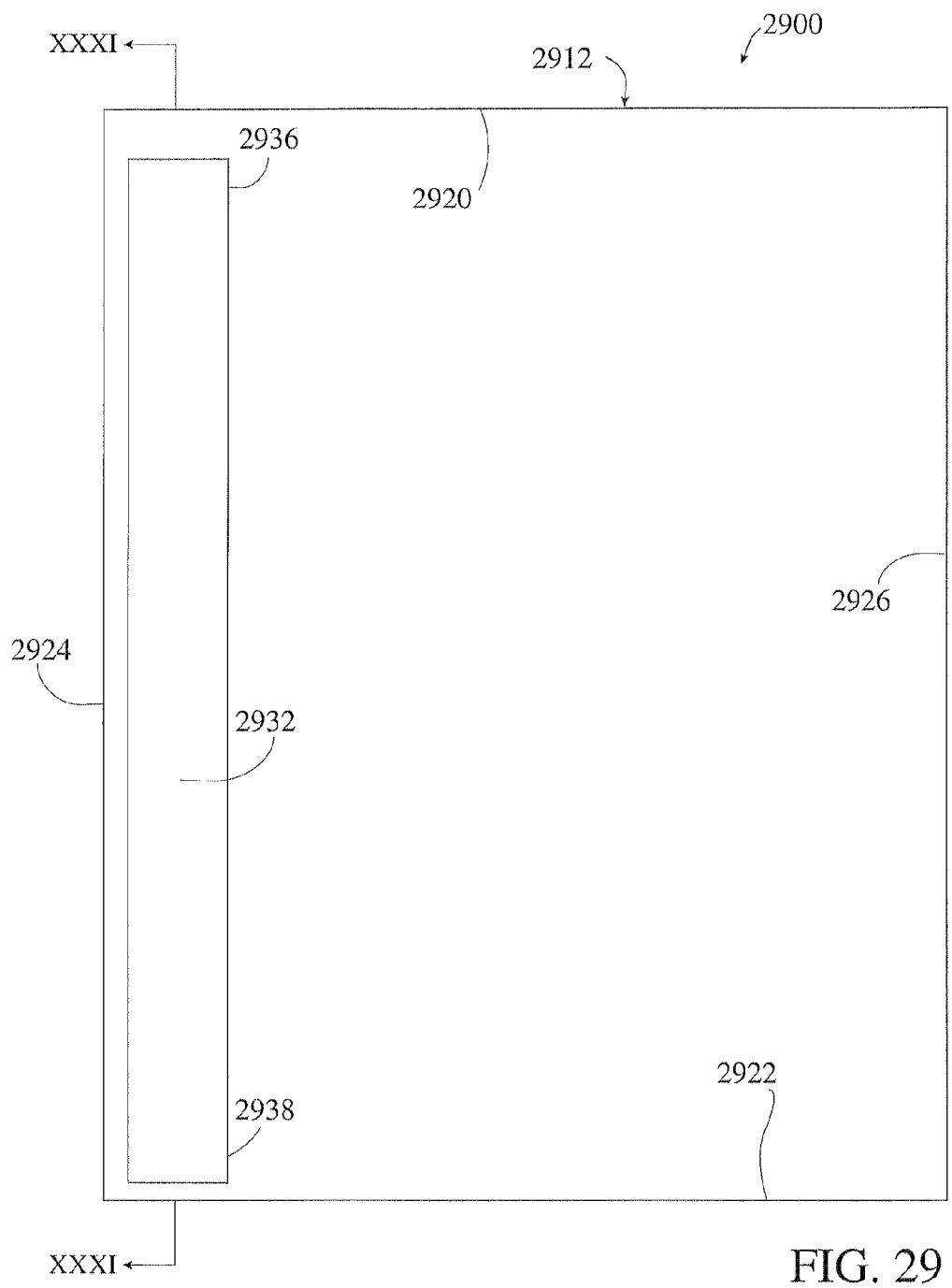
FIG. 29 shows a top view of a wristband sheet according to at least one embodiment of the present disclosure.

FIG. 29 shows a top view of wristband sheet 2900 according to at least one embodiment of the present disclosure. Shown in FIG. 29 is sheet material 2912. In the embodiment of wristband sheet 2900 shown in FIG. 29, sheet material 2912 is bounded by leading edge 2920, trailing edge 2922, side edge 2924, and side edge 2926. Sheet material 2912 may be of any size. In at least one embodiment of sheet material 2912 according to the present disclosure, the outer dimensions of sheet material 2912 are selected to enable sheet material 2912 to fit in a commercially available printing device. For example, in such an embodiment, the outer dimensions of sheet material 2912 may be 3"×11", 8½"×11", 8½"×14", or 210 mm×297 mm.

In at least one embodiment of the present disclosure, sheet material 2912 comprises a material suitable for the printing of indicia thereon, such as, for example, paper, polyester, or another polymer material. Indicia may be marked or printed on the top side of sheet material 2912. For example, the top side of sheet material 2912 may be exposed to an ink jet printer, a laser print, or another type of printing device capable of applying indicia to the top side of sheet material 2912. The inks, toners, and/or other printing materials used in the application of indicia to the top side of sheet material 2912 are selected to be compatible with the printing device used to apply such indicia, the material used for sheet material 2912, and the intended use of wristband sheet 2900.

In at least one embodiment of the present disclosure, wristband 2932 is constructed of a polyester material, although other materials suitable for the intended use of wristband 2932 may be used. In at least one embodiment of the present disclosure, wristband 2932 has dimensions of about 1"×10.75", however wristband 2932 may be of any size that fits on sheet material 2912.

Figure 30:
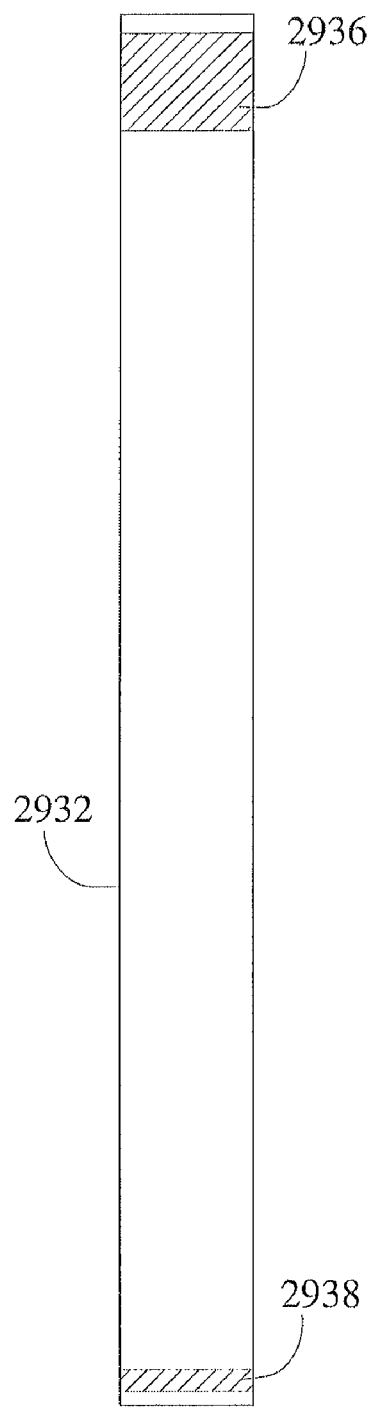
FIG. 30 shows the underside of a wristband according to at least one embodiment of the present disclosure.

FIG. 30 shows the underside of wristband 2932 before attachment to sheet material 2912, according to at least one embodiment of the present disclosure. Shown in FIG. 30 are wristband 2932 comprising adhesive stripe 2936 and adhesive stripe 2938. In at least one embodiment of the present disclosure, adhesive stripes 2936 and 2938 comprise a layer of a repositionable adhesive. In at least one embodiment of the present disclosure, adhesive stripes 2936 and 2938 comprise a layer of a removable adhesive. In at least one embodiment of the present disclosure, adhesive stripes 2936 and 2938 comprise a layer of a pressure sensitive adhesive.

Referring back to FIG. 29, shown therein are the locations of adhesive stripes 2936, 2938 on the underside of wristband 2932. Adhesive stripe 2936 is interposed between wristband 2932 to sheet material 2912 and removably adheres wristband 2932 to sheet material 2912. Adhesive stripe 2938 is interposed between wristband 2932 to sheet material 2912 and removably adheres wristband 2932 to sheet material 2912. As discussed herein, adhesive stripes 2936, 2938 are operable to secure wristband 2932 around a subject's wrist after wristband 2932 is removed from sheet material 2912.

Indicia may be marked or printed on the top side of wristband 2932. For example, the top side of wristband 2932 may be exposed to an ink jet printer, a laser print, or another type of printing device capable of applying indicia to the top side of wristband 2932. Indicia may be printed on wristband 2932 before, after, or concurrently with the printing of indicia on sheet material 2912. The inks, toners, and/or other printing materials used in the application of indicia to the top side of wristband 2932 are selected to be compatible with the printing device used to apply such indicia, the material used for wristband 2932, and the intended use of wristband 2932.

Figure 31:
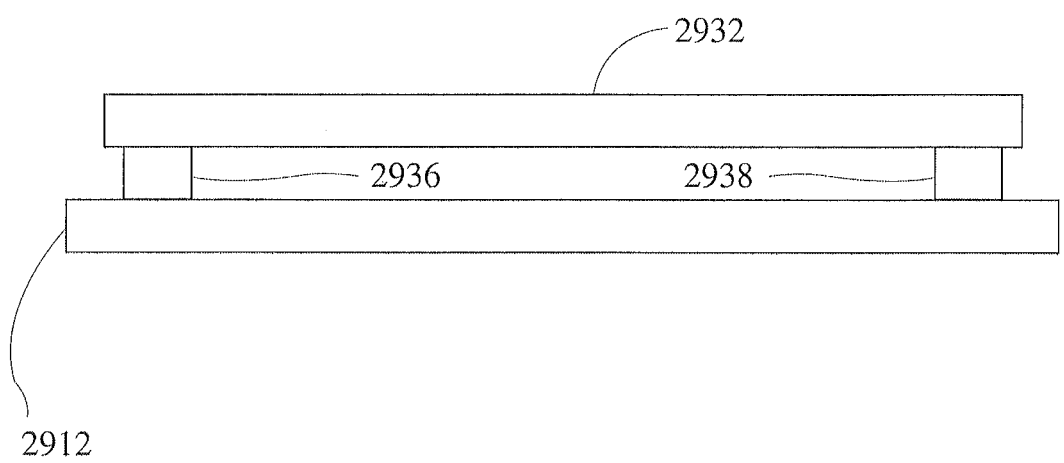
FIG. 31 shows a cross-sectional view of an embodiment of a wristband sheet according to at least one embodiment of the present disclosure.

FIG. 31 shows a cross-sectional view of the embodiment of wristband sheet 2900 of FIG. 29 taken on line XXXI-XXXI of FIG. 29, with the proportions enhanced for purposes of clarity. Shown in FIG. 31 are sheet material 2912, wristband 2932, adhesive stripe 2936, and adhesive stripe 2938.

Figure 32:
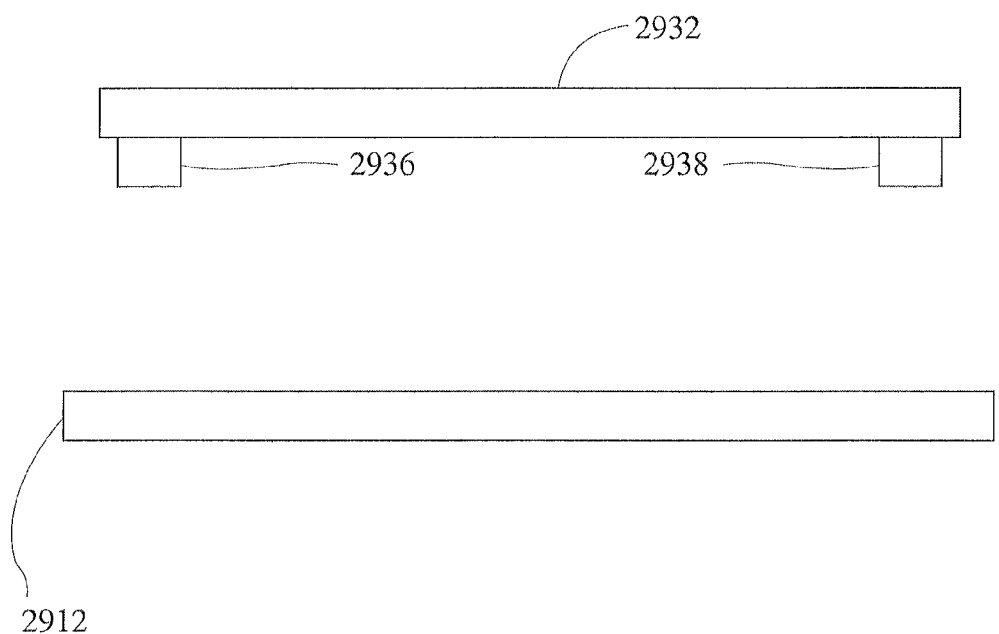
FIG. 32 shows a cross-sectional of an embodiment of a wristband sheet according to at least one embodiment of the present disclosure.

According to at least one embodiment of the present disclosure, wristband 2932 is removable from sheet material 2912 by grasping wristband 2932 between adhesive stripe 2936 and adhesive stripe 2938 and pulling wristband 2932 away from sheet material 2912. FIG. 32 shows a cross-sectional view of an embodiment of wristband sheet 2900 according to at least one embodiment of the present disclosure, with the proportions enhanced for purposes of clarity. As shown in FIG. 32, wristband 2932 is separated from sheet material 2912. As shown in FIG. 32, adhesive stripe 2936 and adhesive stripe 2938 have separated from sheet material 2912. Adhesive stripe 2936 and adhesive stripe 2938 remain adhered to the underside of wristband 2932.

Figure 33:
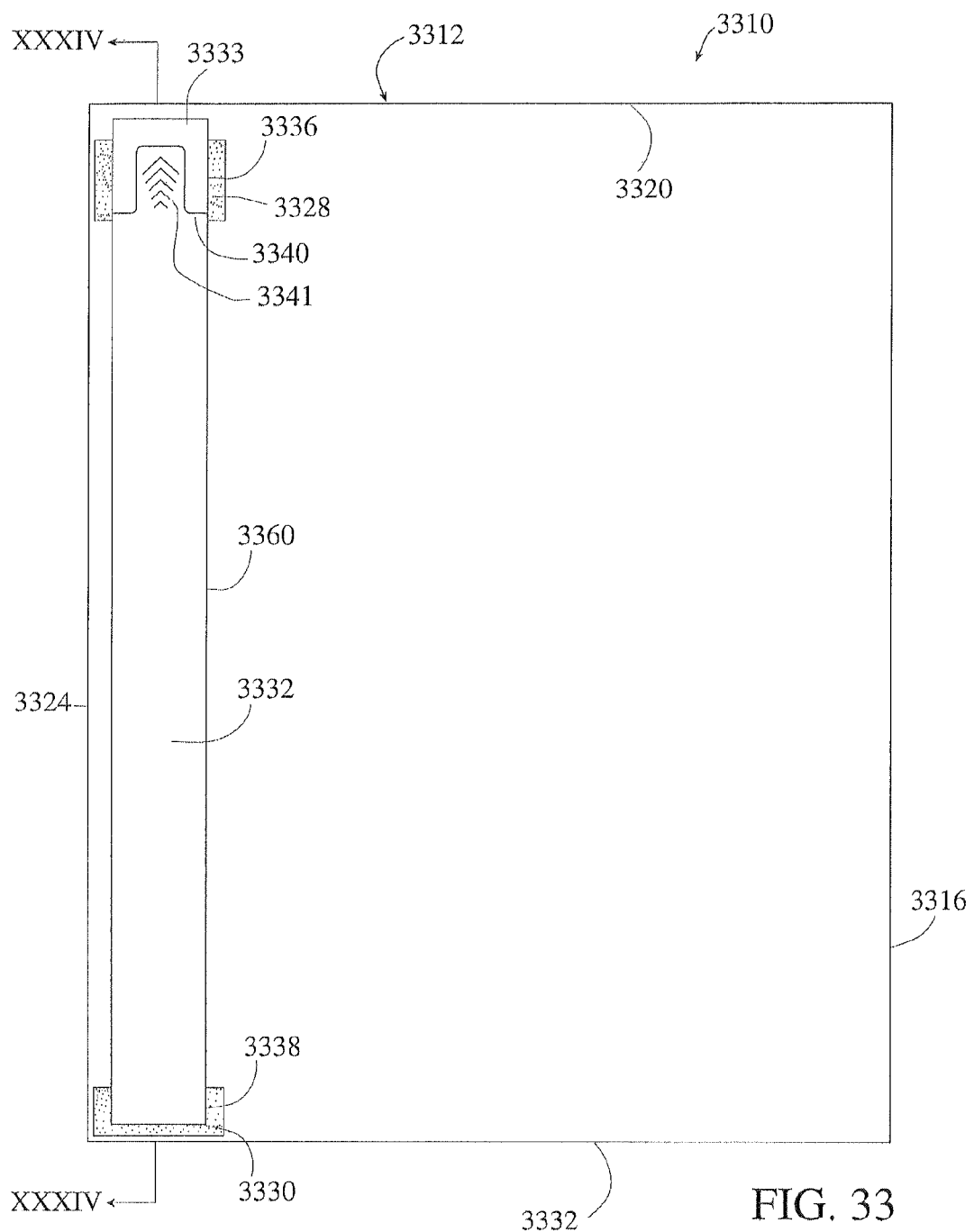
FIG. 33 shows a top view of a wristband sheet according to at least one embodiment of the present disclosure.

FIG. 33 shows a top view of wristband sheet 3310 according to at least one embodiment of the present disclosure. Shown in FIG. 33 is sheet material 3312. In the embodiment of wristband sheet 3310 shown in FIG. 33, sheet material 3312 is bounded by leading edge 3320, trailing edge 3322, side edge 3324, and side edge 3326. Sheet material 3312 may be of any size. In at least one embodiment of sheet material 3312 according to the present disclosure, the outer dimensions of sheet material 3312 are selected to enable sheet material 3312 to fit in a commercially available printing device. For example, in such an embodiment, the outer dimensions of sheet material 3312 may be 3"×11", 8½"×11", 8½"×14", or 210 mm×297 mm.

In at least one embodiment of the present disclosure, sheet material 3312 comprises a material suitable for the printing of indicia thereon, such as, for example, paper, polyester, or another polymer material. Indicia may be marked or printed on the top side of sheet material 3312. For example, the top side of sheet material 3312 may be exposed to an ink jet printer, a laser print, or another type of printing device capable of applying indicia to the top side of sheet material 3312. The inks, toners, and/or other printing materials used in the application of indicia to the top side of sheet material 3312 are selected to be compatible with the printing device used to apply such indicia, the material used for sheet material 3312, and the intended use of wristband sheet 3310.

In the embodiment of wristband sheet 3310 shown in FIG. 33, sheet material 3312 comprises release patch 3328 and release patch 3330. Release patches 3328, 3330 comprise areas of a release coating (such as, for example, a silicone) applied to the surface of sheet material 3312, to allow the removable adherence of wristband 3332 to sheet material 3312, as discussed herein. In at least one embodiment of the present disclosure, release patches 3328, 3330 comprise free radical ultraviolet cured silicone. In at least one embodiment of the present disclosure, release patches 3328, 3330 comprise a cationic ultraviolet cured release coating. Alternatively, any type of coating (including no-silicone coatings) that permits the removable adherence of wristband 3332 to sheet material 3312 may be used.

Also shown in the embodiment of wristband sheet 3310 of FIG. 33 is wristband 3332 comprising stub 3333 and lines of weakness 3340, 3341. In at least one embodiment of the present disclosure, lines of weakness 3340 and/or 3341 comprise a series of perforations cut into wristband 3332, such as by diecutting. In at least one embodiment of the present disclosure, lines of weakness 3340 and/or 3341 comprise a continuous line of weakness cut into wristband 3332, such as by diecutting. In at least one embodiment of the present disclosure, wristband 3332 (including stub 3333) is constructed of a polyester material, although other materials suitable for the intended use of wristband 3332 may be used. In at least one embodiment of the present disclosure, wristband 3332 has dimensions of about 1"×10.75", however wristband 3332 may be of any size that fits on sheet material 3312.

Shown in FIG. 33 are the locations of adhesive stripes 3336, 3338 on the underside of wristband 3332. A portion of adhesive stripe 3336 is interposed between sheet material 3312 and stub 3333, and adheres sheet material 3312 to stub 3333. A portion of adhesive stripe 3336 is interposed between wristband 3332 and release patch 3328 and removably adheres wristband 3332 to release patch 3328. Adhesive stripe 3338 is interposed between wristband 3332 and release patch 3330 and removably adheres wristband 3332 to release patch 3330. As discussed herein, adhesive stripes 3336, 3338 are operable to secure wristband 3332 around a subject's wrist after wristband 3332 is removed from sheet material 3312.

Shown in FIG. 33 is the location of dry lift adhesive material 3360 on the underside of wristband 3332. Dry lift adhesive material 3360 comprises a material capable of removably adhering the underside of wristband 3332 to the top surface of sheet material 3312. The properties of dry lift adhesive material 3360 are such that when wristband 3332 is removed from sheet material 3312, neither the underside of wristband 3332 nor the top surface of sheet material 3312 will have perceptible tackiness or stickiness in the area where dry lift adhesive material 3360 is used. In at least one embodiment of the present disclosure, dry lift adhesive material 3360 comprises a dry lift multi carrier laminate material such as, for example, Diamond Cote Coupon Based Transfer Tape sold by Accucote, Inc.

Figure 34:
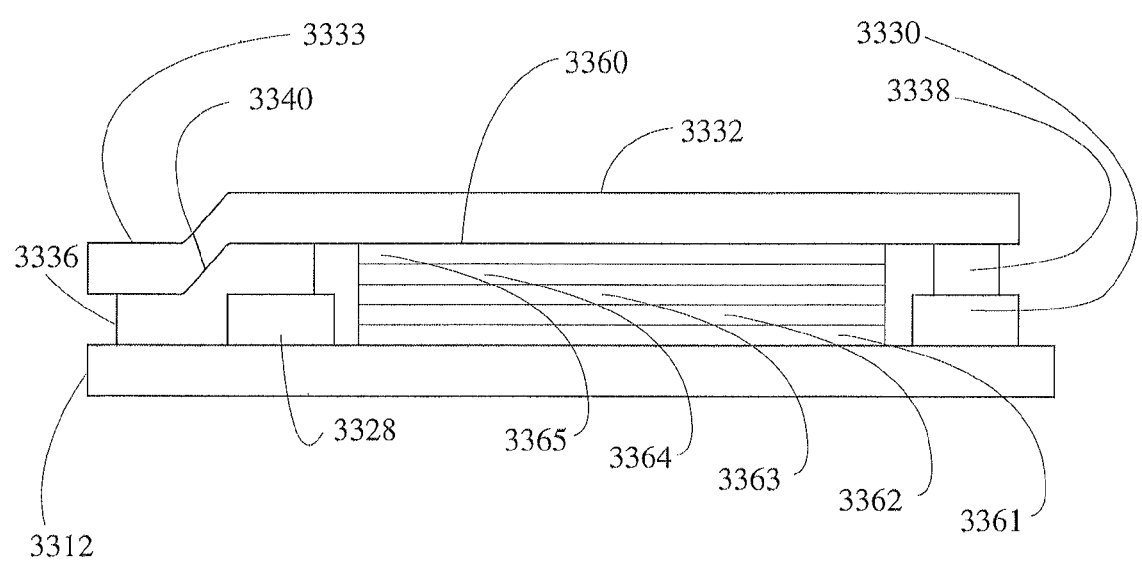
FIG. 34 shows a cross-sectional view of an embodiment of a wristband sheet according to at least one embodiment of the present disclosure.

FIG. 34 shows a cross-sectional view of the embodiment of wristband sheet 3310 of FIG. 33 taken on line XXXIV-XXXIV of FIG. 33, with the proportions enhanced for purposes of clarity. Shown in FIG. 34 are sheet material 3312, release patch 3328, release patch 3330, wristband 3332, stub 3333, adhesive stripe 3336, adhesive stripe 3338, line of weakness 3340, and dry lift adhesive material 3360. As shown in FIG. 34, a portion of adhesive stripe 3336 is interposed between sheet material 3312 and stub 3333, and a portion of adhesive stripe 3336 is interposed between wristband 3332 and release patch 3328.

As shown in FIG. 34, dry lift adhesive material 3360 is interposed between sheet material 3312 and wristband 3332. As shown in FIG. 34, dry lift adhesive material 3360 comprises first adhesive layer 3361, first carrier material 3362, dry lift adhesive layer 3363, second carrier material 3364, and second adhesive layer 3365. First adhesive layer 3361 is interposed between first carrier material 3362 and sheet material 3312 and permanently adheres first carrier material 3362 to sheet material 3312. Second adhesive layer 3365 is interposed between second carrier material 3364 and wristband 3332 and permanently adheres second carrier material 3364 to wristband 3332. Dry lift adhesive layer 3363 is interposed between first carrier material 3362 and second carrier material 3364, and removably adheres first carrier material 3362 to second carrier material 3364.

According to at least one embodiment of the present disclosure, wristband 3332 is removable from sheet material 3312 by pulling wristband 3332 away from sheet material 3312 from the end of wristband 3332 that is opposite stub

Figure 35:
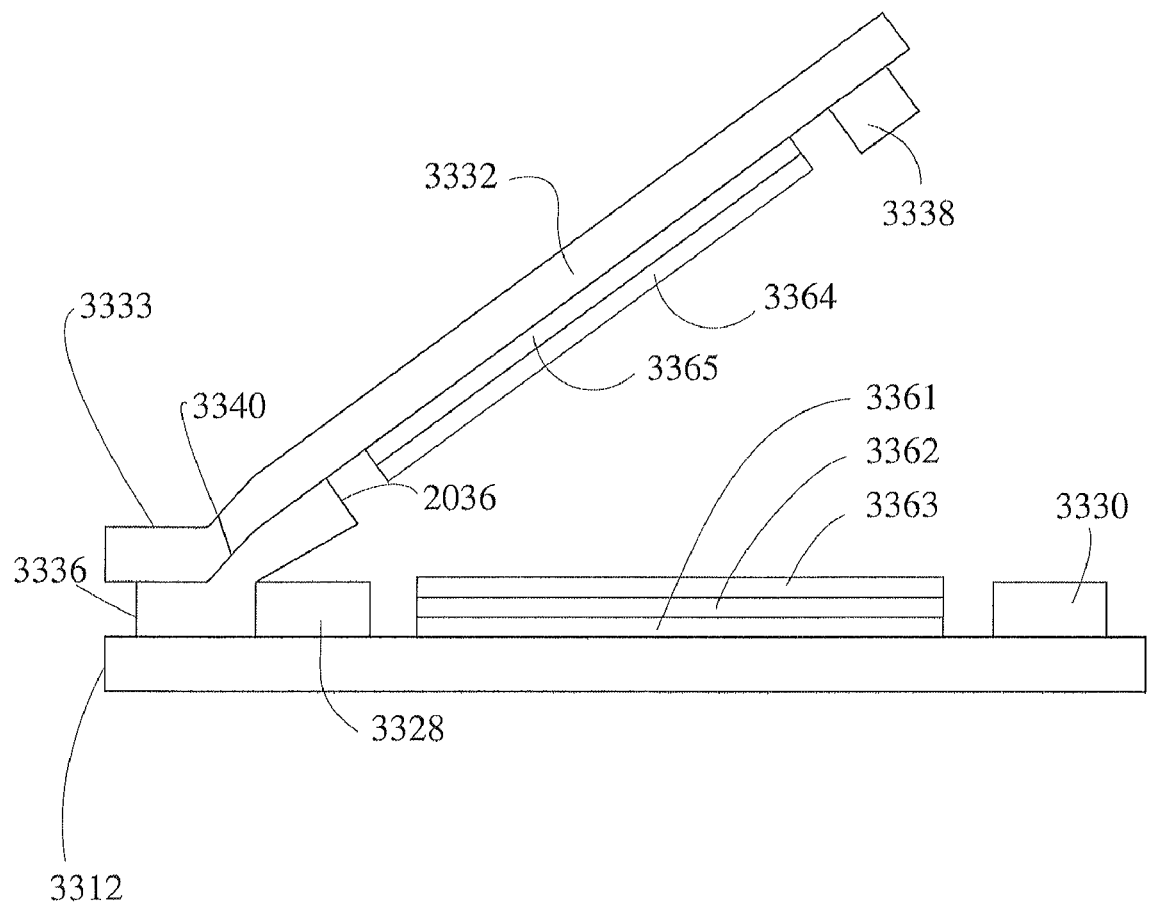
FIG. 35 shows a cross-sectional view of ari embodiment of a wristband sheet according to at least one embodiment of the present disclosure.

3333. FIG. 35 shows a cross-sectional view of an embodiment of wristband sheet 3310 according to at least one embodiment of the present disclosure, with the proportions enhanced for purposes of clarity. As shown in FIG. 35, wristband 3332 is partially separated from sheet material 3312. As shown in FIG. 35, adhesive stripe 3338 and the portion of adhesive stripe 3336 interposed between wristband 3332 and release patch 3328 have separated from release patch 3330 and release patch 3328, respectively. Release patch 3328 and release patch 3330 remain on the top surface of sheet material 3312. Adhesive stripe 3338 and a portion of adhesive stripe 3336 remain adhered to the underside of wristband 3332. Stub 3333 remains adhered to the top surface of sheet material 3312 by a portion of adhesive stripe 3336. Wristband 3332 remains attach to stub 3333 at line of weakness 3340. Dry lift adhesive material 3360 has separated, with first adhesive layer 3361, first carrier material 3362, and dry lift adhesive layer 3363 remaining adhered to sheet material 3312, and second adhesive layer 3365 and second carrier material 3364 remaining adhered to wristband 3332.

Figure 36:
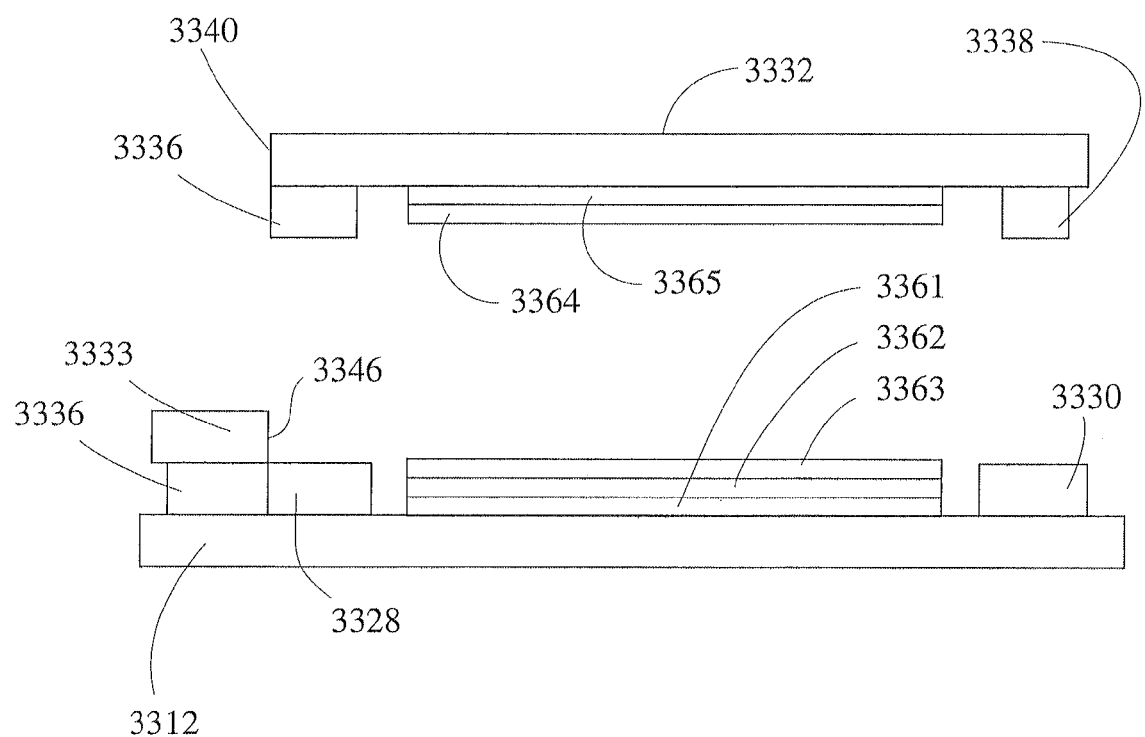
FIG. 36 shows a cross-sectional view of an embodiment of a wristband sheet according to at least one embodiment of the present disclosure.

FIG. 36 shows a cross-sectional view of an embodiment of wristband sheet 3310 according to at least one embodiment of the present disclosure, with the proportions enhanced for purposes of clarity. As shown in FIG. 36, wristband 3332 is fully separated from sheet material 3312, and wristband 3332 is separated from stub 3333 at line of weakness 3340. Stub 3333 remains adhered to the top surface of sheet material 3312 by a portion of adhesive stripe 3336. As shown in FIG. 36, adhesive stripe 3338 and a portion of adhesive stripe 3336 remain adhered to the underside of wristband 3332, and release patch 3328 and release patch 3330 remain adhered to sheet material 3312. Wristband 3332 comprises lines of weakness 3341 (not shown in FIG. 36). First adhesive layer 3361, first carrier material 3362, and dry lift adhesive layer 3363 remain adhered to sheet material 3312, and second adhesive layer 3365 and second carrier material 3364 remain adhered to wristband 3332. A surface of dry lift adhesive layer 3363 is exposed, however the properties of dry lift adhesive layer 3363 are such that there is no perceptible tackiness or stickiness on the exposed surface of dry lift adhesive layer 3363.

In the embodiment of the present disclosure shown in FIGS. 35-36, dry lift adhesive material 3360 is shown cleanly separating at the boundary between second carrier material 3364 and dry lift adhesive layer 3363. However, in other embodiments dry lift adhesive material 3360 may separate at the boundary between first carrier material 3362 and dry lift adhesive layer 3363. In still other embodiments, there may not be a clean separation between dry lift adhesive layer 3363 and the adjacent layers of carrier material. Instead, for example, a portion of dry lift adhesive layer 3363 may remain adhered to first carrier material 3362 and a portion of dry lift adhesive layer 3363 may remain adhered to second carrier material 3364. Nevertheless, each exposed surface of dry lift adhesive layer 3363 will have no perceptible tackiness or stickiness.

Figure 37A:
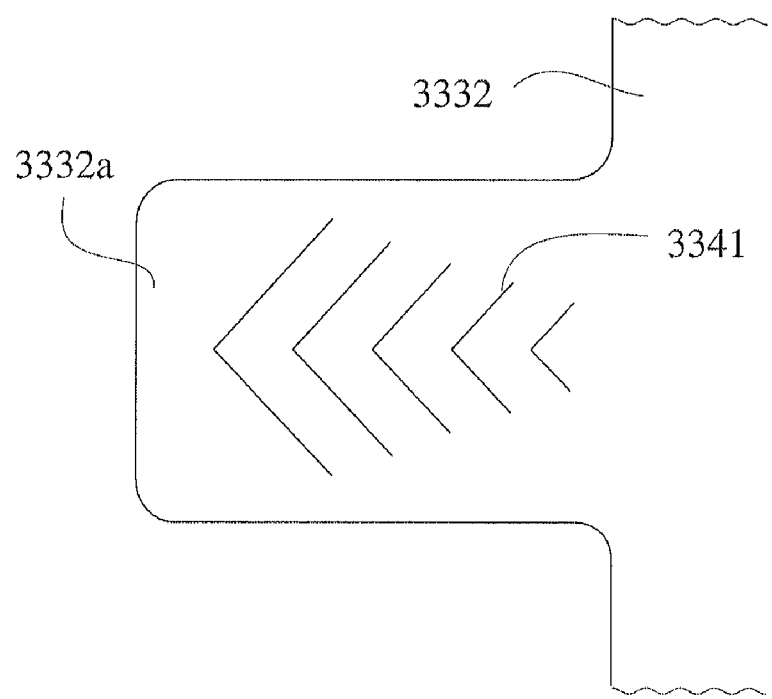
FIG. 37A shows a detailed top view of one end of a wristband according to at least one embodiment of the present disclosure.
Figure 37B:
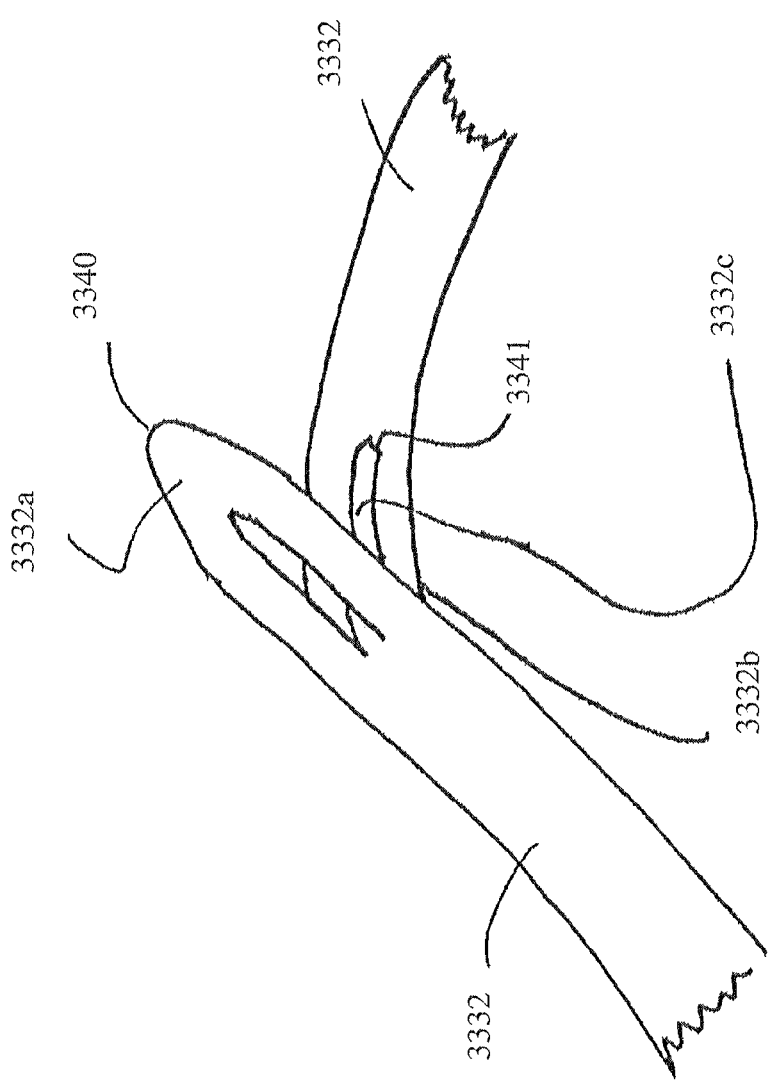
FIG. 37B shows a perspective view of the tamper resistant features of a wristband according to at least one embodiment of the present disclosure.

FIG. 37A shows a detailed top view of one end of wristband 3332 following removal from sheet material 3312. Shown in FIG. 37 are wristband 3332 and lines of weakness 3341. Lines of weakness 3341 are operable to provide a tamper-detection feature for wristband 3332. Wristband 3332 is looped around the wrist of a subject in the manner substantially the same as that shown in FIG. 9 and/or FIGS. 25B-C. If an attempt is made to remove wristband 3332 from the subject's wrist, wristband 3332 will tear at lines of weakness 3341 in a manner substantially the same as that shown in FIG. 37B, thereby revealing that an attempt was made to remove wristband 3332.

FIGS. 38A-D shows a flowchart illustrating a process for manufacturing a wristband sheet according to at least one embodiment of the present disclosure.

Figure 38A:
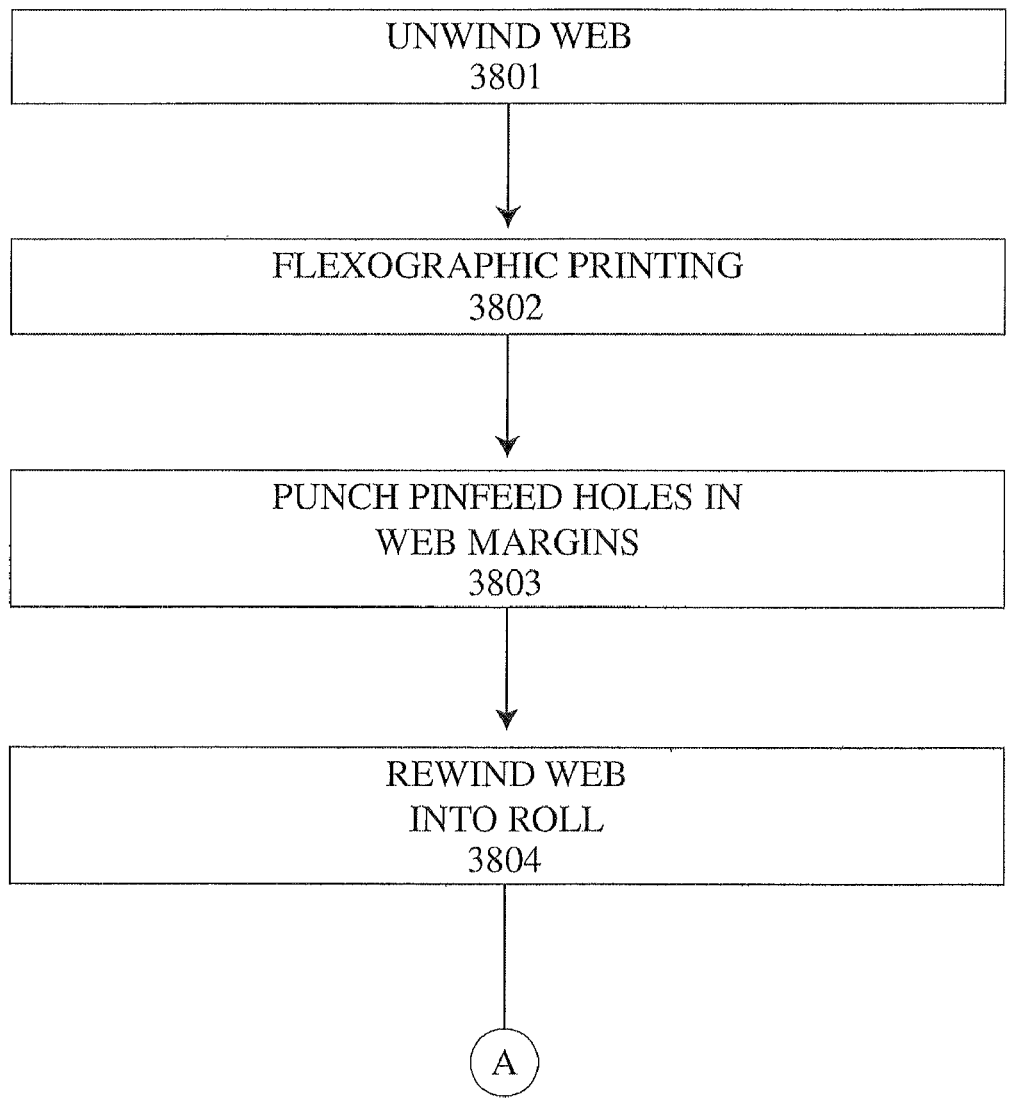
FIGS. 38A-D shows a flowchart for a process for manufacturing a wristband sheet according to at least one embodiment of the present disclosure.

In step 3801 of the embodiment of the present disclosure shown in FIG. 38A, a web of sheet material is unwound from a roll and fed mechanically into one or more flexographic printheads. According to at least one embodiment of the present disclosure, the web of sheet material comprises an edge margin of at least about ½" on each edge, such that the overall width of web of sheet material is 1" greater than the desired width of the finished product.

In step 3802 of the embodiment of the present disclosure shown in FIG. 38A, one or more flexographic printheads apply one or more release patches comprising silicone or another type of release coating to the surface of the sheet material. Such flexographic printheads also may apply colored inks. If advantageous to improve the performance of the silicone or other type of release patch material, a primer may be printed prior to printing the silicone or other release coating. In at least one embodiment of the present disclosure, the silicone that is used is free radical ultraviolet curable silicone, in which the silicone is printed with conventional flexoprinting technology and then is cured in a ultraviolet curing system that exposes the uncured silicone to ultraviolet light. In such cases, the flexographic printing step shown on FIG. 38A includes a ultraviolet curing step. In at least one embodiment of the present disclosure, such an ultraviolet curing system comprises nitrogen to promote the cure. Other embodiments of the present disclosure may use ultraviolet curable silicones that do not require nitrogen to cure, but such silicones may be less reliable for consistent release values. Still other embodiments of the present disclosure use release coatings that do not contain silicone and may or may not require ultraviolet light to cure or dry.

In step 3803 of the embodiment of the present disclosure shown in FIG. 38A, the web of sheet material proceeds to a punching station where pinfeed holes are punched in ½" margins at each edge of the web of sheet material, to facilitate registration of the web of sheet material in the process during which wristbands are applied to the web of sheet material (discussed hereinafter).

In step 3804 of the embodiment of the present disclosure shown in FIG. 38A, after printing of release patches and punching of pinfeed holes, the web of sheet material is rewound onto rolls that will be furnished to the patching machine process.

Figure 38B:
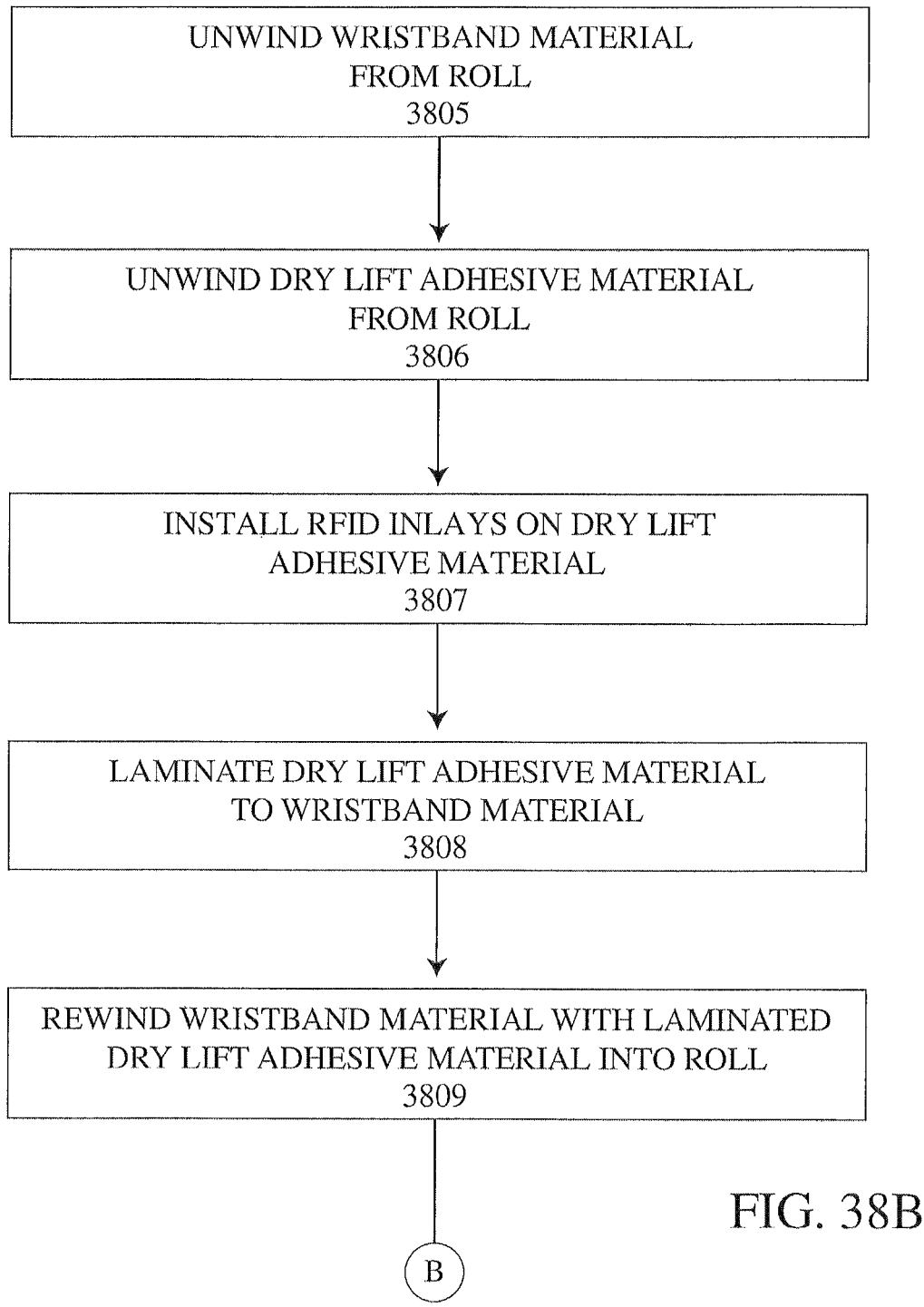

In step 3805 of the embodiment of the present disclosure shown in FIG. 38B, a roll of wristband material (such as, for example, a roll of a polyester material) is unwound mechanically. According to at least one embodiment of the present disclosure, the width of the wristband material on the roll of wristband material is the same as the desired width of the wristband to be applied to the web of sheet material (discussed hereinafter).

In step 3806 of the embodiment of the present disclosure shown in FIG. 38B, a roll of dry lift adhesive material (such as, for example, a roll of Diamond Cote Coupon Based Transfer Tape sold by Accucote, Inc.) is unwound mechanically. According to at least on embodiment of the present disclosure, the width of the dry lift adhesive material on the roll is the same as the desired width of the dry lift adhesive material to be applied the roll of wristband material (discussed hereinafter).

In step 3807 of the embodiment of the present disclosure shown in FIG. 38B, one or more RFID inlays optionally can be installed on the dry lift adhesive material in a manner that will result in the RFID inlay(s) being inserted between the dry lift adhesive material and the underside of the wristband material. The installation of RFID inlays in controlled so that the desired number of RFID inlays (normally one) will be present in each wristband. If RFID inlays are not installed on the dry lift adhesive material, then the process proceeds from step 3806 to step 3808.

In step 3808 of the embodiment of the present disclosure shown in FIG. 38B, the dry lift adhesive material is laminated to the underside of the wristband material. In at least one embodiment, the dry lift adhesive material comprises a permanent adhesive which is used to laminate the wristband material to the dry lift adhesive material. In at least one embodiment, the dry lift adhesive material is laminated to the underside of the wristband material so as to leave portions of the underside of the wristband material exposed at each edge of the wristband material.

In step 3809 of the embodiment of the present disclosure shown in FIG. 38B, after the wristband material is laminated to the dry lift adhesive material, the web of laminated wristband material and dry lift adhesive material is rewound onto rolls that will be furnished to the patching machine process. If RFID inlays are used, the RFID inlays will be contained within the roll as well.

Figure 38C:
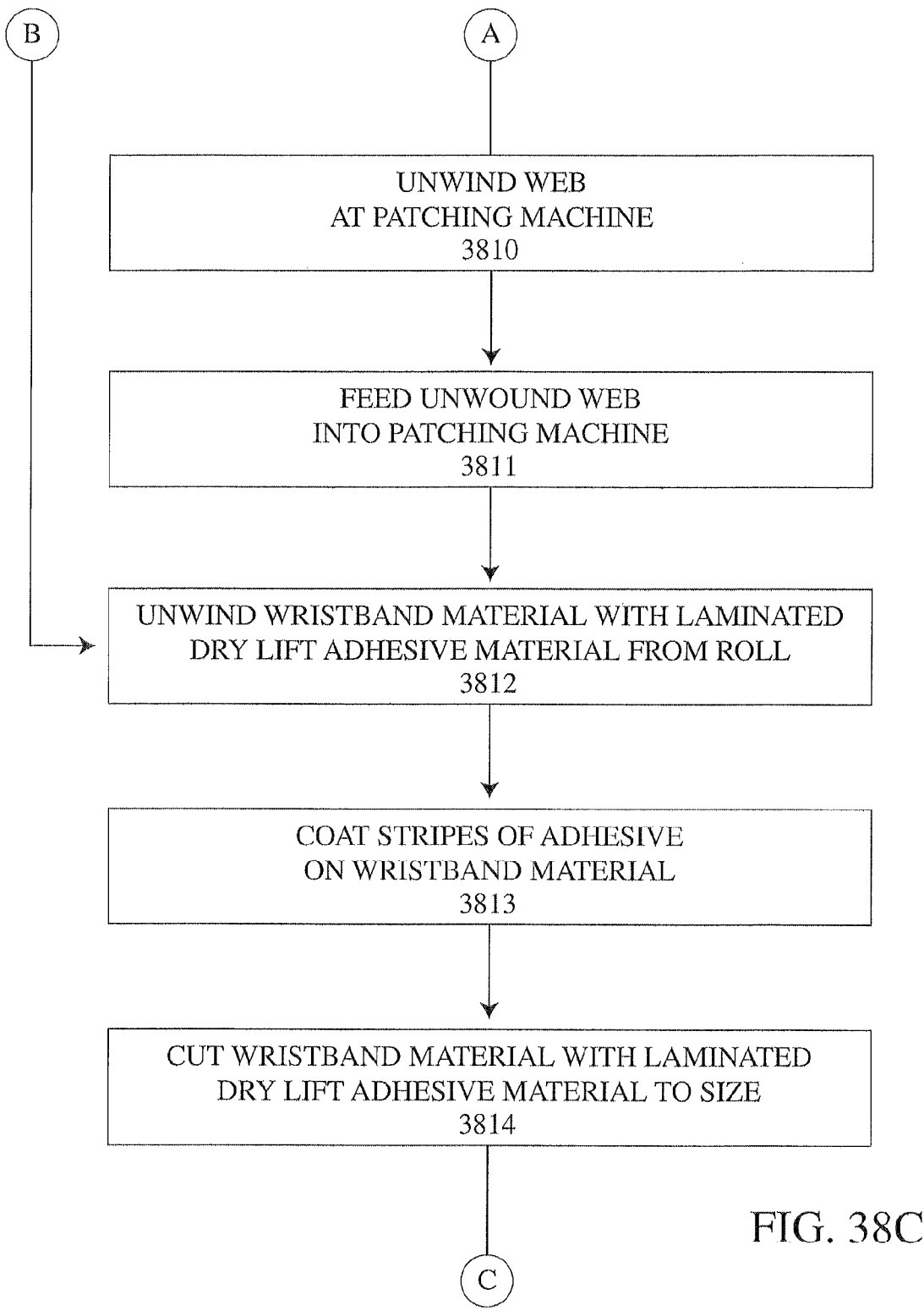

In step 3810 of the embodiment of the present disclosure shown in FIG. 38C, the rolled web of sheet material from step 3804 is unwound and fed into a patching machine, wherein one or more wristbands will be applied to the web of sheet material.

In at least one alternative embodiment of the present disclosure, the steps shown as step 3804 and step 3810 may be omitted. In such an embodiment, the web of sheet material proceeds from step 3803 to step 3811.

In step 3811 of the embodiment of the present disclosure shown in FIG. 38C, the punched pinfeed holes in the web of sheet material engage with a pinfeed mechanism of the patching machine. The pinfeed mechanism of the patching machine pulls the web of sheet material into and through the patching machine by pins that penetrate the previously punched pinfeed holes and rotate on gear driven shafts to drive the web of sheet material through the patching machine at a predetermined feed rate.

In step 3812 of the embodiment of the present disclosure shown in FIG. 38C, the roll of laminated wristband material and dry lift adhesive material is unwound mechanically and fed into the patching machine. If RFID inlays are used, the RFID inlays will be contained within the roll as well.

In step 3813 of the embodiment of the present disclosure shown in FIG. 38C, at an adhesive coating station the patching machine coats one or more stripes of adhesive on the portions of the underside the web of wristband material that were not covered by the laminated dry lift adhesive material.

In step 3814 of the embodiment of the present disclosure shown in FIG. 38B, the patching machine cuts each wristband (including laminated dry lift adhesive material) to a predetermined length. For example, if the finished product required a 1" long wristband, the patching machine cuts off a 1" length of wristband material from the roll of wristband material. In an exemplary embodiment where a 1" long, 10.75" wide wristband is to be applied to a 8.5" long sheet material, the 10.75" wide web of wristband material is fed by computer controlled nip type feed rollers at a rate of 1" for every 8.5" of sheet material is that is fed through the patching machine. Although a 1" long wristband is used this example, the wristband can be any length. The length of the wristband can be controlled by entering a desired length in the computerized controller for the nip type feed rollers. The adhesive striped, optionally perforated, web of wristband material is fed at the chosen rate to a vacuum cylinder. The vacuum cylinder holds the web of wristband material in place while a cutting cylinder cuts a wristband of the predetermined length from the web. The vacuum cylinder serves as a cutting anvil for the knife of a cutting cylinder. In certain embodiments of the present disclosure, a liquid silicone application contacts the knives of the cutting cylinder to prevent the exposed adhesive that is on the web of wristband material from sticking to the knives of the cutting cylinder. If RFID inlays are used, the patching machine may possess a sensor to read the position of the RFID inlays and cut the wristband material between the RFID inlays.

Figure 38D:
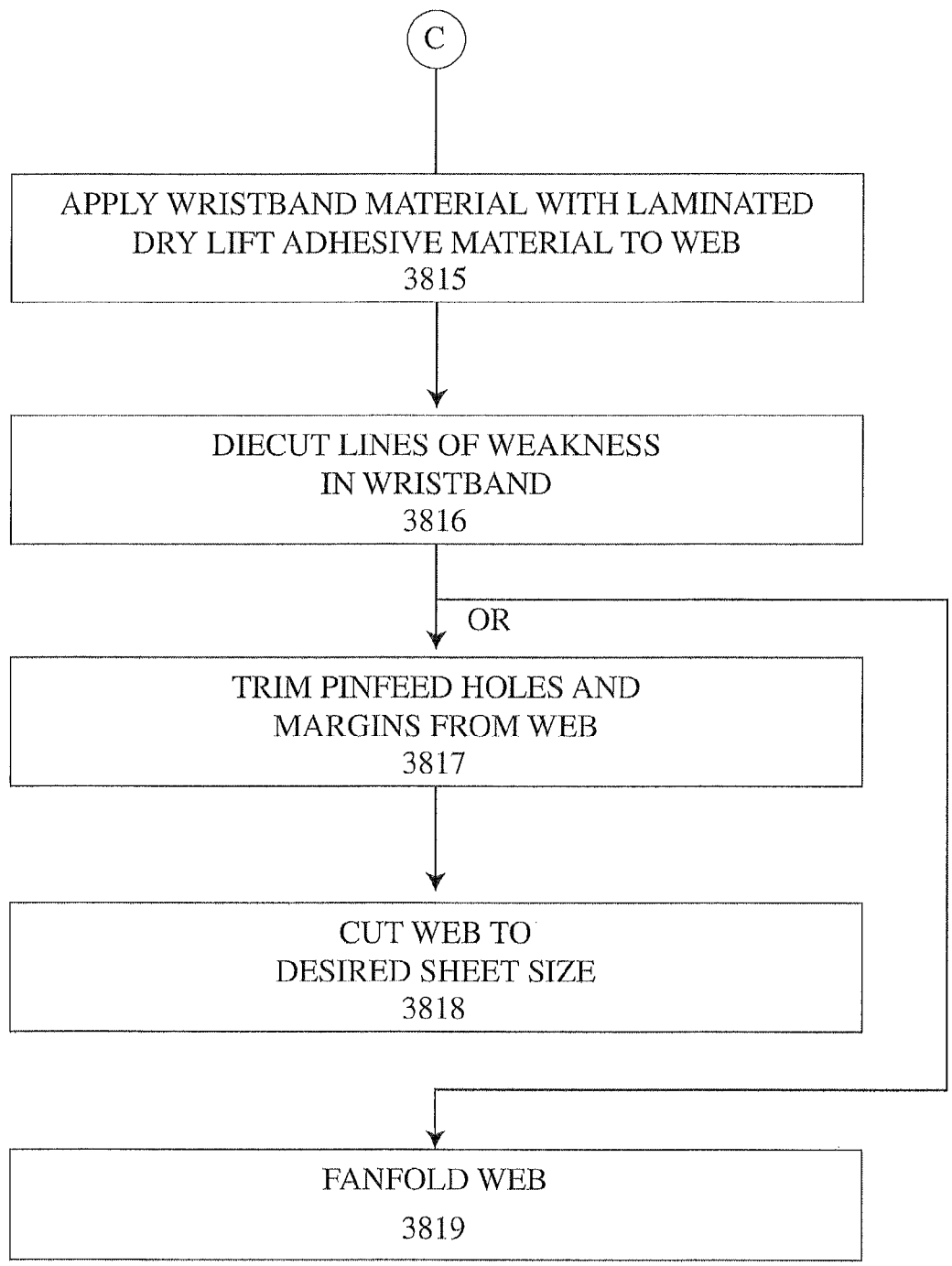

In step 3815 of the embodiment of the present disclosure shown in FIG. 38D, after the wristband is cut to length, the vacuum cylinder carries each cut-off wristband to an impression roller that is wrapped by the web of sheet material. At the impression roller the wristband is transferred from the vacuum cylinder to the face of the web of sheet material. The wristband is applied such that one or more of the adhesive stripes on the underside of the wristband are aligned with one or more of the release patches on the sheet material. The wristband is adhered to the web of sheet material by the adhesive stripes that were applied to the underside of the wristband, and also by the dry lift adhesive material. The dry lift adhesive material comprises a permanent adhesive which is used to laminate the dry lift adhesive material to the sheet material. The patching machine comprises gearing that keeps the cutting cylinder and vacuum cylinder in time with the pace at which the patching machine's pinfeed mechanism moves the web of sheet material.

In step 3816 of the embodiment of the present disclosure shown in FIG. 38C, if required for the wristband sheet design, lines of weakness are diecut into the wristband at a diecutting station. This diecutting is done after the wristband is applied to the sheet material.

In step 3817 of the embodiment of the present disclosure shown in FIG. 38C, if required for the wristband sheet design, the ½" margins (including the pinfeed holes) are mechanically trimmed off of the web of sheet material at a trimming station.

In step 3818 of the embodiment of the present disclosure shown in FIG. 38C, if required for the wristband sheet design, the web of sheet material including the applied wristband is mechanically cut into sheets at a sheeter station, with each sheet containing one or more wristbands as required by the wristband sheet design. The sheets are fed into a batcher/stacker, and then may be shrink-wrapped and packaged. Sheeting is an alternative to the fanfolding step discussed hereinafter.

In step 3819 of the embodiment of the present disclosure shown in FIG. 38C, if required for the wristband sheet design, the web of sheet material including the applied wristband may be fanfolded in-line with a mechanical folder or by gravity in waterfall fashion, with each fanfold containing one or more wristbands as required by the wristband sheet design. The wristband sheet design may require the ½" margins with pinfeed holes to be left on the fanfolded web of sheet material. Fanfolding is an alternative to the sheeting step discussed above.

Figure 39:
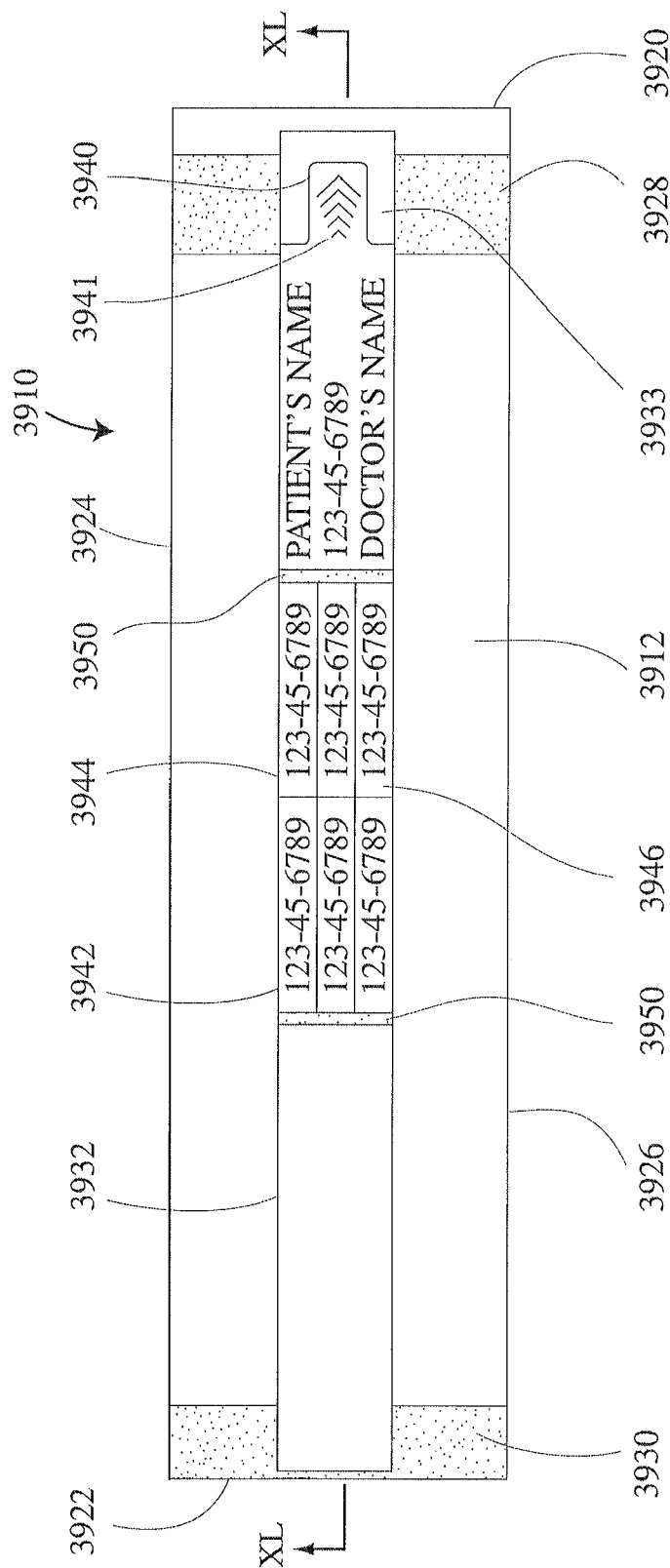
FIG. 39 shows a top view of a wristband sheet according to at least one embodiment of the present disclosure.

FIG. 39 shows a top view of wristband sheet 3910 according to at least one embodiment of the present disclosure. Shown in FIG. 39 is sheet material 3912. In the embodiment of wristband sheet 3910 shown in FIG. 39, sheet material 3912 is bounded by leading edge 3920, trailing edge 3922, side edge 3924, and side edge 3926. Sheet material 3912 may be of any size. In at least one embodiment of sheet material 3912 according to the present disclosure, the outer dimensions of sheet material 3912 are selected to enable sheet material 3912 to fit in a commercially available printing device. For example, in such an embodiment, the outer dimensions of sheet material 3912 may be 3"×11", 8½"×11", 8½"×14", or 210 mm×297 mm.

In at least one embodiment of the present disclosure, sheet material 3912 comprises a material suitable for the printing of indicia thereon, such as, for example, paper, polyester, or another polymer material. Indicia may be marked or printed on the top side of sheet material 3912. For example, the top side of sheet material 3912 may be exposed to an ink jet printer, a laser print, or another type of printing device capable of applying indicia to the top side of sheet material 3912. The inks, toners, and/or other printing materials used in the application of indicia to the top side of sheet material 3912 are selected to be compatible with the printing device used to apply such indicia, the material used for sheet material 3912, and the intended use of wristband sheet 3910.

In the embodiment of wristband sheet 3910 shown in FIG. 39, sheet material 3912 comprises release patch 3928 and release patch 3930. Release patches 3928, 3930 comprise areas of a release coating (such as, for example, a silicone) applied to the surface of sheet material 3912, to allow the removable adherence of wristband 3932 to sheet material 3912, as discussed herein. In at least one embodiment of the present disclosure, release patches 3928, 3930 comprise free radical ultraviolet cured silicone. In at least one embodiment of the present disclosure, release patches 3928, 3930 comprise a cationic ultraviolet cured release coating. Alternatively, any type of coating (including no-silicone coatings) that permits the removable adherence of wristband 3932 to sheet material 3912 may be used.

Also shown in the embodiment of wristband sheet 3910 shown in FIG. 39 is wristband 3932 comprising stub 3933, lines of weakness 3940, 3941, and label material 3944 comprising one or more labels 3946. In at least one embodiment of the present disclosure, adhesive 3942 (not shown in FIG. 39) is interposed between label material 3944 and wristband 3932 and removably adheres label material 3944 to wristband 3932. In at least one embodiment of the present disclosure, wristband 3932 comprises silicone coating 3950 on at least a portion of the surface of wristband 3932 facing the underside of label(s) 3946. In such an embodiment, adhesive 3942 (not shown in FIG. 39) is interposed between label material 3944 and silicone coating 3950 and removably adheres label material 3944 to silicone coating 3950.

In at least one embodiment of the present disclosure, adhesive 3942 is a pressure sensitive adhesive. In at least one embodiment of the present disclosure, lines of weakness 3940 and/or 3941 comprise a series of perforations cut into wristband 3932, such as by diecutting. In at least one embodiment of the present disclosure, lines of weakness 3940 and/or 3941 comprise a continuous line of weakness cut into wristband 3932, such as by diecutting. In at least one embodiment of the present disclosure, wristband 3932 (including stub 3933) is constructed of a polyester material, although other materials suitable for the intended use of wristband 3932 may be used. In at least one embodiment of the present disclosure, wristband 3932 has dimensions of about 1"×10.75", however wristband 3932 may be of any size that fits on sheet material 3912.

Figure 40:
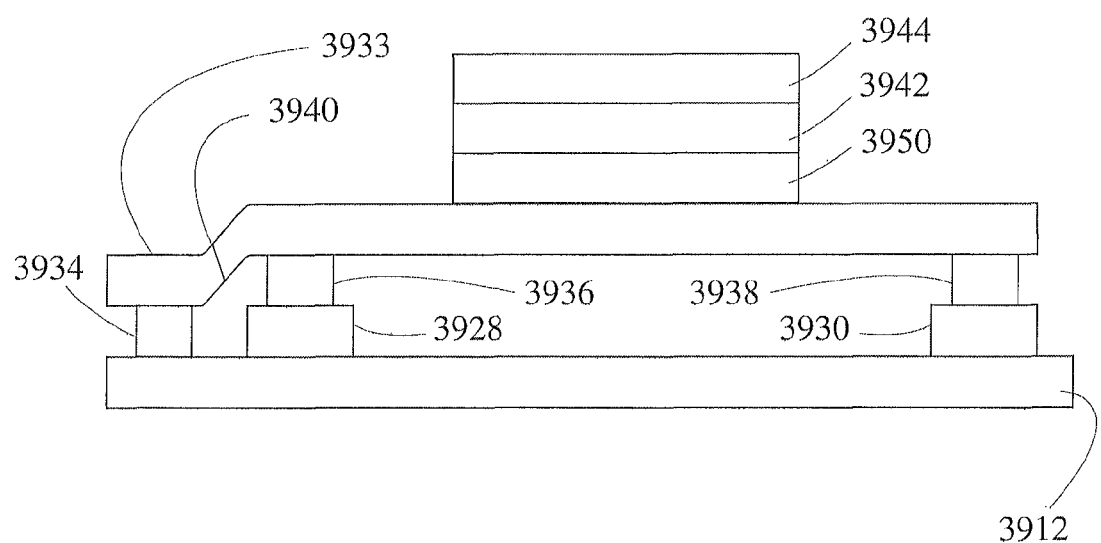
FIG. 40 shows a cross-sectional view of an embodiment of a wristband sheet according to at least one embodiment of the present disclosure.

FIG. 40 shows a cross-sectional view of the embodiment of wristband sheet 3910 of FIG. 39 taken on line XL-XL of FIG. 39, with the proportions enhanced for purposes of clarity. Shown in FIG. 40 are sheet material 3912, release patch 3928, release patch 3930, wristband 3932, stub 3933, adhesive stripe 3934, adhesive stripe 3936, adhesive stripe 3938, line of weakness 3940, adhesive 3942, label material 3944, and silicone coating 3950.

Figure 41:
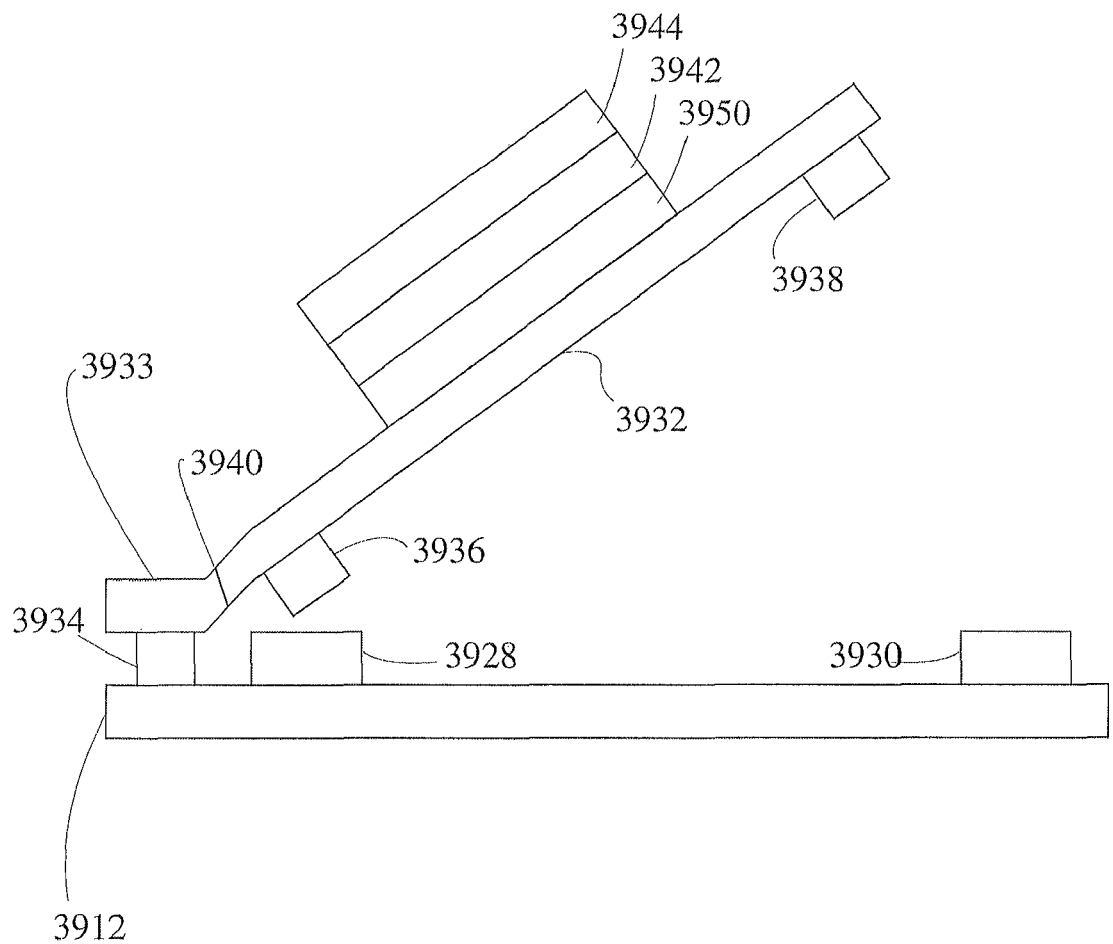
FIG. 41 shows a cross-sectional view of an embodiment of a wristband sheet according to at least one embodiment of the present disclosure.

According to at least one embodiment of the present disclosure, wristband 3932 is removable from sheet material 3912 by grasping wristband 3932 between adhesive stripe 3936 and adhesive stripe 3938 and pulling wristband 3932 away from sheet material 3912. FIG. 41 shows a cross-sectional view of an embodiment of wristband sheet 3910 according to at least one embodiment of the present disclosure, with the proportions enhanced for purposes of clarity. As shown in FIG. 41, wristband 3932 is partially separated from sheet material 3912. As shown in FIG. 41, adhesive stripe 3936 and adhesive stripe 3938 have separated from release patch 3928 and release patch 3930, respectively. Release patch 3928 and release patch 3930 remain on the top surface of sheet material 3912. Adhesive stripe 3936 and adhesive stripe 3938 remain adhered to the underside of wristband 3932. Stub 3933 remains adhered to the top surface of sheet material 3912 by adhesive stripe 3934. Wristband 3932 remains attach to stub 3933 at line of weakness 3940.

Figure 42:
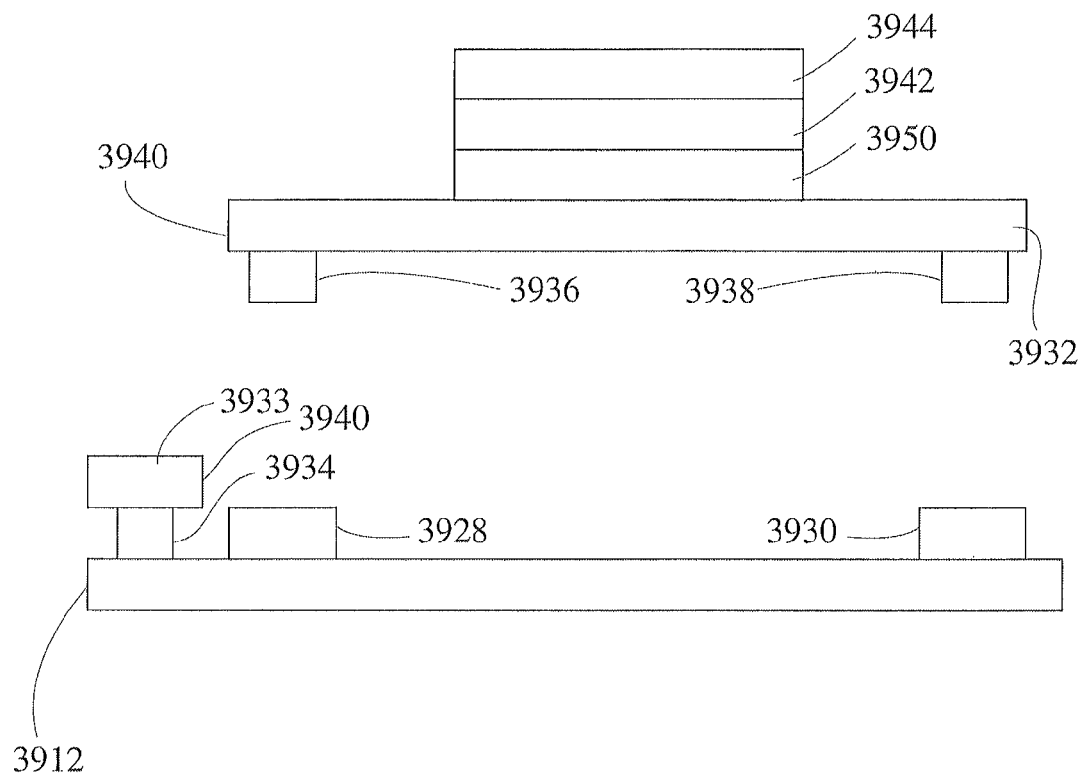
FIG. 42 shows a cross-sectional view of an embodiment of a wristband sheet according to at least one embodiment of the present disclosure.

FIG. 42 shows a cross-sectional view of an embodiment of wristband sheet 10 according to at least one embodiment of the present disclosure, with the proportions enhanced for purposes of clarity. As shown in FIG. 42, wristband 3932 is fully separated from sheet material 3912, and wristband 3932 is separated from stub 3933 at line of weakness 3940. Stub 3933 remains adhered to the top surface of sheet material 3912 by adhesive stripe 3934. As shown in FIG. 42, adhesive stripes 3936, 3938 remain adhered to the underside of wristband 3932, and release patch 3928 and release patch 3930 remain adhered to sheet material 3912. As shown in FIG. 42, label material 3944 and adhesive 3942 remain adhered to the top side of wristband 3932.

Figure 43:
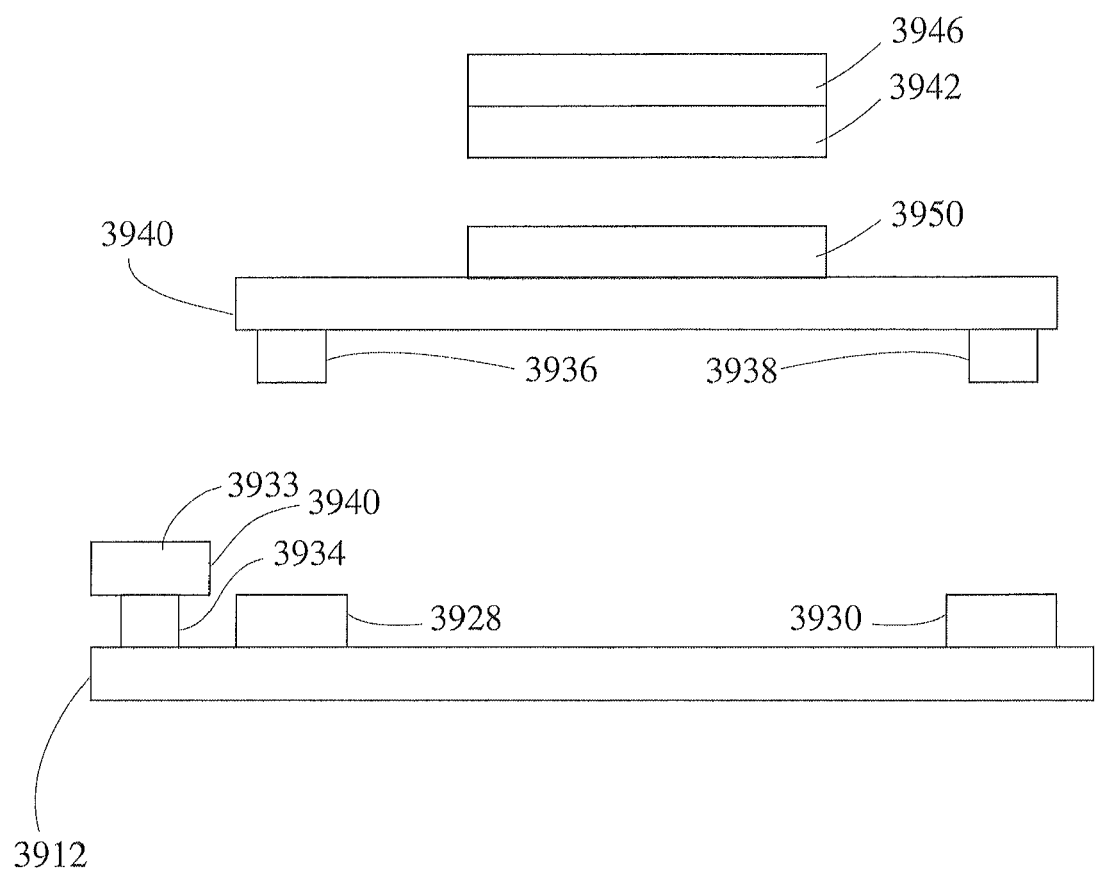
FIG. 43 shows a cross-sectional view of an embodiment of a wristband sheet according to at least one embodiment of the present disclosure.

FIG. 43 shows a cross-sectional view of an embodiment of wristband sheet 3910 according to at least one embodiment of the present disclosure, with the proportions enhanced for purposes of clarity. As shown in FIG. 43, wristband 3932 is fully separated from sheet material 3912, and wristband 3932 is separated from stub 3933 at line of weakness 3940. Stub 3933 remains adhered to the top surface of sheet material 3912 by adhesive stripe 3934. As shown in FIG. 43, adhesive stripes 3936, 3938 remain adhered to the underside of wristband 3932, and release patch 3928 and release patch 3930 remain adhered to sheet material 3912. As shown in FIG. 43, at least one label 3946 is separated from adhesive 3942, and silicone coating 3950 remains adhered to the top side of wristband 3932.

While this disclosure has been described as having preferred designs, the apparatus and methods according to the present disclosure can be further modified within the scope and spirit of this disclosure. This application is therefore intended to cover any variations, uses, or adaptations of the disclosure using its general principles. For example, the sizes, quantities, and locations of the wristband(s), adhesive stripes, lines of weakness, and/or printed release patches can be varied.

In yet another example, although the embodiments disclosed herein are disclosed in terms of one wristband to a sheet, embodiments comprising the application of more than one wristband to a sheet are within the scope of the present disclosure.

In yet another example, any embodiment of a wristband sheet according to the present disclosure may comprise an RFID inlay on the top side or underside of the wristband.

As a further example, any methods disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains.

The invention claimed is:

1. A printable form comprising:
   a sheet material, said sheet material comprising a first surface and a second surface opposite said first surface, said first surface bounded by a leading edge, a trailing edge, and first and second side edges;
   a wristband piece adhered to said first surface but not formed from said sheet material, said wristband piece comprising an elongate strip of a flexible material suitable for wrapping around a human limb, said wristband piece comprising a leading margin, a trailing margin, first and second side margins, a top side, an opposing underside, a stub portion, a removeable wristband portion, and a line of weakness extending across said wristband piece between said first side margin and said second side margins, said stub portion being separable from said removeable wristband portion at said line of weakness, said underside comprising an underside surface bounded by said leading margin, said trailing margin, and said first and second side margins; and
   at least one adhesive stripe interposed between said first surface and said underside surface such that said removeable wristband portion is removably attached to said first surface, said at least one adhesive stripe covering a minority of said underside surface, said stub portion is directly adhered to said first surface, and at least a portion of said underside surface is substantially free of said adhesive, wherein when said removeable wristband portion is removed from said first surface said stub portion remains adhered to said first surface and said removable portion separates from said stub portion at said line of weakness.

2. The printable form of claim 1, wherein said wristband piece comprises an upper ply and a lower ply, and a boundary of at least one detachable label is defined in said upper ply.

3. The printable form of claim 1, wherein said removeable wristband portion further comprises a tamper resistant feature, said tamper resistant feature being within an area of said removeable wristband portion to which at least one said adhesive stripe is adhered.

4. The printable form of claim 3, wherein said tamper resistant feature comprises at least one deformation in said removeable wristband portion, said at least one deformation being inboard of said leading margin, said trailing margin, and said first and second side margins.

5. The printable form of claim 4, wherein said at least one deformation is closer to said leading margin than to said trailing margin.

6. The printable form of claim 1, wherein said at least one adhesive stripe comprises a first adhesive stripe between said stub portion and said first surface, a second adhesive stripe between said removeable wristband portion and said first surface, and a third adhesive stripe between said removeable wristband portion and said first surface, and wherein said second adhesive stripe is positioned closer to said leading margin than to said trailing margin, and said third adhesive stripe is positioned closer to said trailing margin than to said leading margin.

7. The printable form of claim 6, wherein following removal of said removeable wristband portion from said first surface said second adhesive stripe and said third adhesive stripe remain adhered to said underside surface.

8. The printable form of claim 1, wherein said at least one adhesive stripe comprises a first adhesive stripe between said stub portion and said first surface and a second adhesive stripe between said removeable wristband portion and said first surface, wherein said second adhesive stripe is positioned closer to said trailing margin than to said leading margin.

9. The printable form of claim 8, wherein following removal of said removeable wristband portion from said first surface said second adhesive stripe remains adhered to said underside surface.

10. A printable form comprising:
    a substrate material, said substrate material bounded by a leading edge, a trailing edge, and first and second side edges, said substrate material comprising a face ply and a liner ply, said face ply comprising a face ply surface and a second surface opposite said face ply surface, said liner ply removably adhered to said second surface of said face ply;
    a wristband piece adhered to said face ply but not formed from said substrate material, said wristband piece comprising an elongate strip of a flexible material suitable for wrapping around a human limb, said wristband piece comprising a leading margin, a trailing margin, first and second side margins, a top side, an opposing underside, a stub portion, a removeable wristband portion, and a line of weakness extending across said wristband piece between said first side margin and said second side margins, said stub portion being separable from said removeable wristband portion at said line of weakness, said underside comprising an underside surface bounded by said leading margin, said trailing margin, and said first and second side margins; and
    at least one adhesive stripe interposed between said face ply surface and said underside surface such that said removeable wristband portion is removably attached to said face ply surface, said stub portion is directly adhered to said face ply surface, and at least a portion of said underside surface is substantially free of said adhesive, wherein when said removeable wristband portion is removed from said face ply surface said stub portion remains adhered to said face ply surface and said removable portion separates from said stub portion at said line of weakness.

11. The printable form of claim 10, wherein said wristband piece further comprises a tamper resistant feature formed in said removeable wristband portion, said tamper resistant feature being formed in said removeable wristband portion within an area of said removeable wristband portion to which said first adhesive stripe is adhered.

12. The printable form of claim 11, wherein said tamper resistant feature comprises at least one line of weakness formed in said removeable wristband portion, said at least one line of weakness being inboard of said leading margin, said trailing margin, and said first and second side margins.

13. The printable form of claim 10, wherein said wristband piece comprises an upper ply and a lower ply, and a boundary of at least one detachable label is defined in said upper ply.

14. The printable form of claim 10, wherein said at least one adhesive stripe comprises a first adhesive stripe between said stub portion and said face ply surface and a second adhesive stripe between said removeable wristband portion and said face ply surface, wherein said second adhesive stripe is positioned closer to said trailing margin than to said leading margin.

15. The printable form of claim 14, wherein following removal of said removeable wristband portion from said face ply surface said second adhesive stripe remains adhered to said underside surface.

16. The printable form of claim 10, wherein said at least one adhesive stripe comprises a first adhesive stripe between said stub portion and said face ply surface, a second adhesive stripe between said removeable wristband portion and said face ply surface, and a third adhesive stripe between said removeable wristband portion and said face ply surface, and wherein said second adhesive stripe is positioned closer to said leading margin than to said trailing margin, and said third adhesive stripe is positioned closer to said trailing margin than to said leading margin.

17. The printable form of claim 16, wherein following removal of said removeable wristband portion from said face ply surface said second adhesive stripe and said third adhesive stripe remain adhered to said underside surface.

\* \* \* \* \*